United States Patent
Defossa et al.

(10) Patent No.: US 6,395,737 B1
(45) Date of Patent: May 28, 2002

(54) MALONIC ACID DERIVATIVES, PROCESSES FOR THEIR PREPARATION, FOR THEIR USE AND PHARMACEUTICAL COMPOSITIONS CONTAINING THEM

(75) Inventors: Elisabeth Defossa, Idstein; Uwe Heinelt, Wiesbaden; Otmar Klingler, Rodgau; Gerhard Zoller, Schöneck; Hans Matter, Langenselbold, all of (DE); Fahad A. Al-Obeidi; Armin Walser, both of Tucson, AZ (US); Peter Wildgoose, Oberursel (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/473,053

(22) Filed: Dec. 28, 1999

(30) Foreign Application Priority Data

Jan. 2, 1999 (EP) .............................................. 99100002
Oct. 1, 1999 (EP) .............................................. 99119537

(51) Int. Cl.$^7$ .................... A61K 31/165; A61K 31/216; C07C 237/00
(52) U.S. Cl. ............................ 514/252.12; 514/255.01; 514/329; 514/331; 514/423; 514/522; 514/539; 514/563; 514/604; 514/616; 544/383; 544/389; 544/391; 544/400; 546/224; 546/331; 548/540; 558/414; 560/35; 560/41; 562/440; 562/450; 564/91; 564/153
(58) Field of Search .................. 514/237.5, 254.11, 514/255.01, 318, 329, 330, 331, 332, 357, 423, 456, 542, 563, 604, 616, 252.12, 522, 539; 544/383, 389, 168, 362, 391, 400; 546/194, 231, 335, 224; 548/540; 549/407; 560/37, 42, 35, 41; 562/440, 450; 564/91, 147, 153; 558/414

(56) References Cited

U.S. PATENT DOCUMENTS

| | | | | |
|---|---|---|---|---|
| 5,518,735 A | | 5/1996 | Stürzebecher et al. ....... | 424/449 |
| 5,607,937 A | | 3/1997 | Stuerzebecher et al. .... | 514/255 |
| 5,977,074 A | * | 11/1999 | Cordell et al. ................ | 514/19 |
| 6,096,885 A | * | 8/2000 | Dezube et al. ............... | 540/527 |

FOREIGN PATENT DOCUMENTS

| | | |
|---|---|---|
| DE | 235 866 | 5/1986 |
| DE | 242 404 | 1/1987 |
| EP | 0 075 896 | 4/1983 |
| EP | 1 016 663 | 7/2000 |
| WO | WO 92/08709 | 5/1992 |
| WO | WO 93/21208 | 10/1993 |
| WO | WO 94/18185 | 8/1994 |
| WO | WO 95/29189 | 11/1995 |
| WO | WO 96/05189 | 2/1996 |
| WO | WO 97/22712 | 6/1997 |
| WO | WO 98/50420 | 11/1998 |
| WO | WO 99/33800 | 7/1999 |

OTHER PUBLICATIONS

Patel et al. Retro–inverso tripeptide renin inhibitors. Bioorg. Med. Chem. Bioorg. Med. Chem. Lett. 2(9), pp. 1089–1092, 1992.*

Dezube et al., Chemical Abstracts, vol. 125:115153, 1996.*

Cordell et al., Chemical Abstracts, vol. 123:257414, 1995.*

Patel et al., Chemical Abstracts, vol. 119:160776, 1993.*

Chaturvedi et al., Chemical Abstracts, vol. 95:43627, 1981.*

D. Michael Jones et al., Thrombin Inhibitors Based on Ketone Derivatives of Arginine and Lysine, J. Enzyme Inhibition, vol. 9, pp. 43–60, 1995.

Stephen F. Brady et al., Amide and α–Keto Carbonyl Inhibitors of Thrombin Based on Arginine and Lysine: Synthesis, Stability and Biological Characterization, Bioorganic & Medicinal Chemistry, vol. 3, pp. 1063–1078, 1995.

Yoshino et al., "Synthesis and Structure–Activity Relationships of Dynorphin A–(1–8) Amide Analogues," J. Med. Chem., vol. 33, pp. 206–212 (1990).

Wiley et al., "D–Phe–Pro–p–Amidinobenzylamine: A Potent and Highly Selective Thrombin Inhibitor," Medicinal Chemistry Letters, vol. 6, pp. 2387–2392 (1996).

(List continued on next page.)

Primary Examiner—Ricahrd L. Raymond
(74) Attorney, Agent, or Firm—Finnegan,. Henderson, Farabow, Garrett & Dunner, LLP

(57) ABSTRACT

New compounds for the inhibition of blood clotting proteins, and more particularly, to malonic acid derivatives of the formula I,

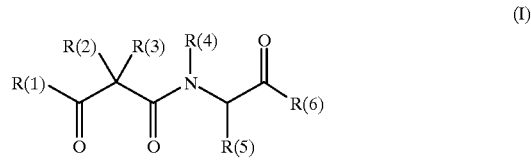

(I)

wherein R(1), R(2), R(3), R(4), R(5), and R(6) have the meanings indicated in the claims. The compounds of formula I are inhibitors of the blood clotting enzyme factor Xa. Processes for the preparation of the compounds of formula I, methods of inhibiting factor Xa activity and of inhibiting blood clotting, use of the compounds of formula I in the treatment and prophylaxis of diseases, which can be treated or prevented by the inhibition of factor Xa activity such as thromboembolic diseases, and use of the compounds of formula I in the preparation of medicaments to be applied in such diseases. Compositions containing a compound of formula I in admixture or otherwise in association with an inert carrier, in particular pharmaceutical compositions containing a compound of formula I together with pharmaceutically acceptable carrier substances and auxiliary substances.

17 Claims, No Drawings

OTHER PUBLICATIONS

Sturzebecher et al., "Structure—Activity Relationships of Inhibitors Derived from 3-Amidinophenylanine," J. Enzyme Inhibition, vol. 9, pp. 87–99 (1995).
Voigt et al., "Synthese von Nα-(Arylsulfonyl)-4-amidino-phenylalanyl-prolinen und von Nα-(Arylsulfonylglycyl)-(amidino-phenylalanyl-prolinen und deren Prufung als Inhibitoren von Serinproteinasen," Pharmazie, vol. 43, 412–414 (1988).
Derwent Abstract of DD 242 404 (1987).
Derwent Abstract of DD 235 866 (1986).
Derwent Abstract of WO 96/05189 (1996).

* cited by examiner

MALONIC ACID DERIVATIVES, PROCESSES FOR THEIR PREPARATION, FOR THEIR USE AND PHARMACEUTICAL COMPOSITIONS CONTAINING THEM

This application claims the benefit of foreign priority to European Application 99100002.7, filed Jan. 2, 1999, and European Application 99119537.1, filed Oct. 1, 1999. Both these priority documents are incorporated by reference herein.

The present invention relates to new compounds for the inhibition of blood clotting proteins, and more particularly, to malonic acid derivatives of the formula I,

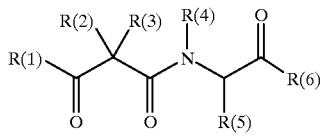

(I)

in which R(1), R(2), R(3), R(4), R(5), and R(6) are defined as indicated below. The compounds of formula I are inhibitors of the blood clotting enzyme factor Xa. The invention also relates to processes for the preparation of the compounds of formula I, to methods of inhibiting factor Xa activity and of inhibiting blood clotting, to the use of the compounds of formula I in the treatment and prophylaxis of diseases which can be treated or prevented by the inhibition of factor Xa activity such as thromboembolic diseases, to and the use of the compounds of formula I in the preparation of medicaments to be applied in such diseases. The invention further relates to compositions containing a compound of formula I in admixture or otherwise in association with an inert carrier, in particular pharmaceutical compositions containing a compound of formula I together with pharmaceutically acceptable carrier substances and auxiliary substances.

The ability to form blood clots is vital to survival. In certain disease states, however, the formation of blood clots within the circulatory system is itself a source of morbidity. It is nevertheless not desirable in such disease states to completely inhibit the clotting system because life threatening hemorrhage would ensue. In order to reduce the instances of the intravascular formation of blood clots those skilled in the art have endeavoured to develop an effective inhibitor of factor Xa, or prothrombinase, the enzyme which is incorporated into the prothrombinase complex where it serves to activate thrombin during clot formation. Appropriate concentrations of such an inhibitor would increase the level of prothrombinase forming agents required to initiate clotting, but would not unduly prolong the clotting process once a threshold concentration of thrombin had been obtained.

Blood coagulation is a complex process involving a progressively amplified series of enzyme activation reactions in which plasma zymogens are sequentially activated by limited proteolysis. Mechanistically the blood coagulation cascade has been divided into intrinsic and extrinsic pathways, which converge at the activation of factor X; subsequent generation of the thrombin proceeds through a single common pathway (see Scheme 1).

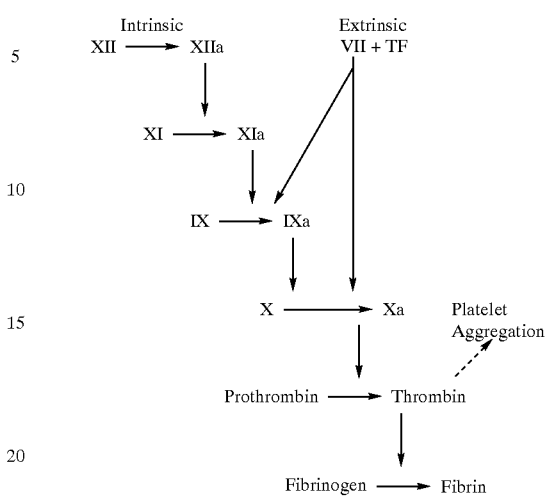

Scheme 1: Blood coagulation cascade

Present evidence suggests that the intrinsic pathway plays an important role in the maintenance and growth of fibrin formation, while the extrinsic pathway is critical in the initiation phase of blood coagulation. It is generally accepted that blood coagulation is physically initiated upon formation of a tissue factor (TF)/factor VIIa complex. Once formed, this complex rapidly initiates coagulation by activating factors IX and X. The newly generated activated factor X, i.e. factor Xa, then forms a one-to-one complex with factor Va and phospholipids to form a prothrombinase complex, which is responsible for converting soluble fibrinogen to insoluble fibrin via the activation of thrombin from its precursor prothrombin. As time progresses, the activity of the factor VIIa/tissue factor complex (extrinsic pathway) is suppressed by a Kunitz-type protease inhibitor protein, TFPI, which, when complexed to factor Xa, can directly inhibit the proteolytic activity of factor VIIa/tissue factor. In order to maintain the coagulation process in the presence of an inhibited extrinsic system, additional factor Xa is produced via the thrombin-mediated activity of the intrinsic pathway. Thus, thrombin plays a dual autocatalytic role, mediating its own production and the conversion of fibrinogen to fibrin.

The autocatalytic nature of thrombin generation is an important safeguard against uncontrolled bleeding and it ensures that, once a given threshold level of prothrombinase is present, blood coagulation will proceed to completion, effecting, for example, an end of the hemorrhage. Thus, it is most desirable to develop agents that inhibit coagulation without directly inhibiting thrombin. However, despite the long standing recognition of the desirability of such an inhibitor, there is at present no effective specific Xa inhibitor in clinical use.

In many clinical applications there is a great need for the prevention of intravascular blood clots or for anti-coagulant therapy. The currently available drugs are not satisfactory in many specific clinical applications. For example, nearly 50% of patients who have undergone a total hip replacement develop deep vein thrombosis (DVT). The currently approved therapies are fixed dose low molecular weight heparin (LMWH) and variable dose heparin. Even with these drug regimes 10% to 20% of patients develop DVT and 5% to 10% develop bleeding complications.

Another clinical situation for which better anticoagulants are needed concerns subjects undergoing transluminal coronary angioplasty and subjects at risk for myocardial infarction or angina.

The most widely used blood-clotting inhibitors are heparin and the related sulfated polysaccharides, LMWH and heparin sulfate. These molecules exert their anti-clotting effects by promoting the binding of a natural regulator of the clotting process, anti-thrombin III, to thrombin and to factor Xa. The inhibitory activity of heparin primarly is directed toward thrombin, which is inactivated approximately 100 times faster than factor Xa. Although relative to heparin, heparin sulfate and LMWH are somewhat more potent inhibitors of Xa than of thrombin, the differences in vitro are modest (3–30 fold) and effects in vivo can be inconsequential. Hirudin and hirulog are two additional thrombin-specific anticoagulants that have been tested in clinical trials. However, these anticoagulants, which inhibit thrombin, also are associated with bleeding complications.

Preclinical studies in baboons and dogs have shown that specific inhibitors of factor Xa prevent clot formation without producing the bleeding side effects observed with direct thrombin inhibitors.

Several specific inhibitors of factor Xa have been reported. Both synthetic and protein inhibitors of factor Xa have been identified, these include, for example, antistasin ("ATS") and tick anticoagulant peptide ("TAP"). ATS, which is isolated from the leech, *Haementerin officinalis*, contains 119 amino acids and has a Ki for factor Xa of 0.05 nM. TAP, which is isolated from the tick, *Ornithodoros moubata*, contains 60 amino acids and has a Ki for factor Xa of about 0.5 nM.

The effectiveness of recombinantly-produced ATS and TAP have been investigated in a number of animal model systems. Both inhibitors decrease bleeding time compared to other anticoagulants, and prevent clotting in a thromboplastin-induced, ligated jugular vein model of deep vein thrombosis. The results achieved in this model correlate with results obtained using the current drug of choice, heparin.

Subcutaneous ATS also was found to be an effective treatment in a thromboplastin-induced model of disseminated intravascular coagulation (DIC). TAP effectively prevents "high-shear" arterial thrombosis and "reduced flow" caused by the surgical placement of a polyester ("DACRON") graft at levels that produced a clinically acceptable prolongation of the activated partial thromboplastin time (aPTT), i.e. less than about two fold prolongation. By comparison, standard heparin, even at doses causing a five fold increase in the aPTT, did not prevent thrombosis and reduced flow within the graft. The aPTT is a clinical assay of coagulation which is particularly sensitive to thrombin inhibitors.

ATS and TAP have not been developed clinically. One major disadvantage of these two inhibitors is that administration of the required repeated doses causes the generation of neutralizing antibodies, thus limiting their potential clinical use. Moreover, the sizes of TAP and ATS render oral administration impossible, further restricting the number of patients able to benefit from these agents.

A specific inhibitor of factor Xa would have substantial practical value in the practice of medicine. In particular, a factor Xa inhibitor would be effective under circumstances where the present drugs of choice, heparin and related sulfated polysaccharides, are ineffective or only marginally effective. Thus, there exists a need for a low molecular weight, factor Xa-specific blood clotting inhibitor that is effective, but does not cause unwanted side effects.

Low molecular weight, factor Xa-specific blood clotting inhibitors, that are effective but does not cause unwanted side effects have been described (International Application WO 9529189). Indole derivatives as low molecular weight, factor Xa-specific blood clotting inhibitors have been described in International Application WO 99338000. However, besides being an effective factor Xa-specific blood clotting inhibitor, it is desirable that such inhibitors will also have advantageous pharmacological properties, for instance high stability in plasma and liver and high selectivity versus other serine proteases. Thus there exists an ongoing need for novel low molecular weight, factor Xa-specific blood clotting inhibitors that are effective and which will have the above advantages as well.

The present invention satisfies this need by providing novel factor Xa activity inhibiting malonic acid derivatives of formula I and by providing related advantages as well.

EP-A 0 075 896 discloses malonic acid derivatives which are used as intermediates for the synthesis of compounds which have an enkephalinase inhibitory activity.

The present invention provides new malonic acid derivatives of formula I which inhibit factor Xa activity but do not substantially inhibit the activity of other proteases especially those involved in the blood coagulation pathway. Thus, a subject of the present invention are compounds of the formula I,

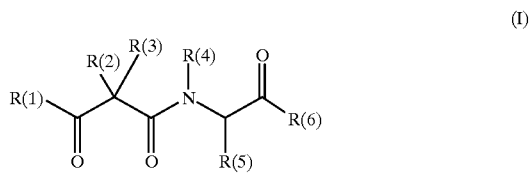

(I)

wherein

R(1) is NR(7)R(8), OR(9), or NR(7a)R(8a);

R(2) is hydrogen or $(C_1-C_4)$-alkyl;

R(3) is $(C_6-C_{10})$-aryl-$(C_1-C_4)$-alkyl which is substituted in the aryl or alkyl moiety by a residue R(11), heteroaryl-$(C_1-C_4)$-alkyl, $(C_3-C_7)$-cycloalkyl-$(C_1-C_4)$-alkyl, where heteroaryl, cycloalkyl, or alkyl are unsubstituted or substituted by one, two, or three residues R(11), or heteroalkyl-$(C_1-C_4)$-alkyl, which is unsubstituted or substituted by a residue R(23);

R(4) is hydrogen, $(C_1-C_4)$-alkyl, $(C_3-C_7)$-cycloalkyl, $(C_3-C_7)$-cycloalkyl-$(C_1-C_4)$-alkyl, or $(C_6-C_{10})$-aryl-$(C_1-C_4)$-alkyl;

R(5) is hydrogen, $(C_1-C_{10})$-alkyl, $(C_3-C_7)$-cycloalkyl, $(C_3-C_7)$-cycloalkyl-$(C_1-C_4)$-alkyl, $(C_6-C_{10})$-aryl, $(C_6-C_{10})$-aryl-$(C_1-C_4)$-alkyl, or a residue of the —C-atom of a natural amino acid, wherein alkyl, cycloalkyl and aryl can be substituted by a residue which is hydroxy, benzyloxy, carboxy, or $N(R(13))_2$; or R(4) and R(5) together form a residue of the formula II or IIII

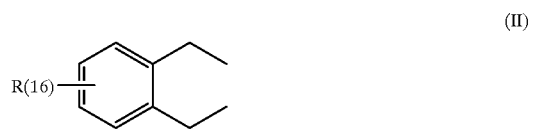

(II)

-continued

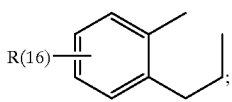
(III)

R(6) is OR(9), N(R(13))$_2$, R(6a), NR(34)R(13), or

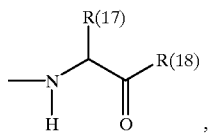

R(6a) is

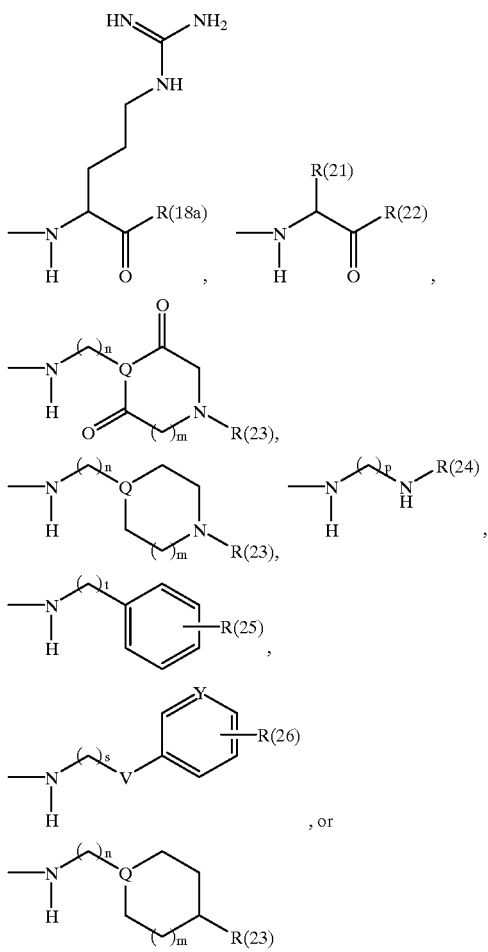

R(7) is hydrogen, (C$_1$–C$_6$)-alkyl or R(8);

R(8) is (C$_1$–C$_6$)-alkyl, (C$_6$–C$_{10}$)-aryl, or (C$_6$–C$_{10}$)-aryl-(C$_1$–C$_4$)-alkyl, where alkyl aryl and aryl in arylalkyl are substituted by one, two or three identical or different residues R(10); or R(7) and R(8) together with the nitrogen atom to which they are bound form a 5- or 6-membered, saturated or unsaturated, heterocyclic ring which does not or does contain an additional nitrogen-, sulfur-, or oxygen-atom atom, and which is unsubstituted or substituted by a residue R(11);

R(7a) and R(8a) are independently of one another hydrogen, (C$_1$–C$_6$)-alkyl, (C$_6$–C$_{10}$)-aryl, or (C$_6$–C$_{10}$)-aryl-(C$_1$–C$_4$)-alkyl;

R(9) is hydrogen, (C$_1$–C$_6$)-alkyl, (C$_6$–C$_{10}$)-aryl, (C$_6$–C$_{10}$)-aryl-(C$_1$–C$_4$)-alkyl, heteroaryl, or heteroaryl-(C$_1$–C$_4$)-alkyl;

R(10) is (C$_1$–C$_4$)-alkoxy, hydroxycarbonyl, (C$_1$–C$_4$)-alkoxycarbonyl, chloro, bromo, fluoro, or (C$_1$–C$_4$)-alkyl, in which 1 to all hydrogen atoms have been replaced by fluorine;

R(11) is R(12) or (C$_1$–C$_4$)-alkyl, which is unsubstituted or substituted by a residue R(12), heteroaryl, which is unsubstituted or substituted by N(R(9))$_2$ or (C$_1$–C$_4$)-alkyl;

R(12) is N(R(13))$_2$, COOR(9), CON(R(13))$_2$, chloro, cyano, NR(15)—C(=NR(14))—NHR(15), C(=NR(14))—R(35), —S(O)(NR(13))—N(R(13))$_2$ or C(=NR(14))—NHR(15);

R(13) is R(15) or (C$_6$–C$_{10}$)-aryl-(C$_1$–C$_4$)-alkyl;

R(14) is R(15), cyano, nitro, amino, hydroxy, (C$_1$–C$_6$)-alkoxy, or (C$_6$–C$_{14}$)-aryl-(C$_1$–C$_6$)-alkoxy, which is unsubstituted or substituted in the aryl moiety for example by (C$_1$–C$_4$)-alkoxy, preferably methoxy, chloro, or (C$_1$–C$_4$)-alkyl, preferably methyl;

R(15) is hydrogen, (C$_1$–C$_6$)-alkyl, (C$_1$–C$_6$)-alkylcarbonyl, (C$_1$–C$_6$)-alkoxycarbonyl, (C$_1$–C$_{18}$)-alkylcarbonyloxy-(C$_1$–C$_6$)-alkoxycarbonyl, optionally substituted (C$_6$–C$_{14}$)-arylcarbonyl, optionally substituted (C$_6$–C$_{14}$)-aryloxycarbonyl or (C$_6$–C$_{14}$)-aryl-(C$_1$–C$_6$)-alkoxycarbonyl which is unsubstituted or substituted in the aryl moiety;

R(16) is hydrogen, (C$_1$–C$_4$)-alkyl, (C$_1$–C$_4$)-alkoxy, fluoro, chloro, bromo, N(R(13))$_2$, nitro, hydroxy, or cyano;

R(17) is (C$_1$–C$_8$)-alkyl, which is substituted by a residue R(12), or heteroaryl-(C$_1$–C$_4$)-alkyl, where the nitrogen, if present in the heteroaryl moiety, is unsubstituted or substituted by (C$_1$–C$_4$)-alkyl to give the N-alkyl heteroaryl moiety which has X$^-$ as the counterion;

R(18) is OR(9) or NR(19)R(20);

R(18a) is NR(19a)R(20a);

R(19) and R(20) independently of one another are hydrogen, (C$_1$–C$_{12}$)-alkyl, (C$_3$–C$_7$)-cycloalkyl, (C$_3$–C$_7$)-cycloalkyl-(C$_1$–C$_4$)-alkyl, where alkyl is unsubstituted or substituted by an aminocarbonyl residue, (C$_6$–C$_{10}$)-aryl, (C$_6$–C$_{10}$)-aryl-(C$_1$–C$_4$)-alkyl, or heteroaryl-(C$_1$–C$_4$)-alkyl; or R(19) and R(20) together with the nitrogen atom to which they are bound form a 5- or 6-membered, saturated or unsaturated, heterocyclic ring, which does not contain or does contain an additional nitrogen-, sulfur- or oxygen atom and which is unsubstituted or substituted by a substituent which is phenyl or naphthyl-sulfonyl which is substituted in the naphtyl-part with chloro, preferably 7-chloro-2-naphthyl-sulfonyl;

R(19a) is hydrogen or R(20a);

R(20a) is (C$_1$–C$_4$)-alkyl, which is substituted by a residue R(27); (C$_3$–C$_7$)-cycloalkyl, (C$_3$–C$_{10}$)-cycloalkyl-(C$_1$–C$_4$)-alkyl, heteroalkyl, heteroalkyl-(C$_1$–C$_4$)-alkyl, heteroaryl-(C$_1$–C$_4$)-alkyl, (C$_6$–C$_{10}$)-aryl, (C$_6$–C$_{10}$)-aryl-(C$_1$–C$_4$)-alkyl, where aryl is substituted by 1, 2, or 3 identical or different residues R(28); or R(19a) and R(20a) together with the nitrogen atom to which they are bound form a 5- or 6-membered heterocyclic ring, which does not contain or does contain an additional nitrogen-, sulfur-, or oxygen atom and which is unsubstituted or substituted by a substituent which is phenyl or $SO_2R(31)$, $SO_2R(31)$ being preferably naphthyl-sulfonyl which is substituted in the naphtyl-part with chloro, most preferably 7-chloro-2-naphthyl-sulfonyl);

R(21) is $(C_6-C_{10})$-aryl, $(C_6-C_{10})$-aryl-$(C_1-C_4)$-alkyl, heteroaryl, or heteroaryl-$(C_1-C_4)$-alkyl, where aryl and heteroaryl are unsubstituted or substituted independently of one another by a residue R(12) or by 1, 2, 3, 4 or 5 identical or different residues R(16), the substitution by these residues at a nitrogen atom of the heteroaryl residue leading to a positively charged nitrogen atom having $X^-$ as the counterion;

R(22) is OR(9), $N(R(13))_2$, or a 5- or 6 membered, nitrogen containing heterocyclic ring, which is bound at the nitrogen;

R(23) is hydrogen, heteroaryl, which is unsubstituted or substituted by a residue $N(R(13))_2$; —NH—S(O)(NR(13))—$(C_1-C_4)$-alkyl, —S(O)(=NR(13))—$N(R(13))_2$, R(12), or R(14);

R(24) is amidino, acetimido, R(29), $(C_6-C_{10})$-aryl, or 2-pyridyl, which is unsubstituted or substituted by a residue R(30);

R(25) is $(C_1-C_4)$-alkyl, which is unsubstituted or substituted with one, two or three residues R(32); $(C_1-C_4)$-alkoxycarbonyl, cyano, chloro, CO—$N(R(13))_2$, hydroxycarbonyl, $(C_1-C_6)$-alkoxycarbonyl, $N(R(13))_2$, $S(O)_r$—$(C_1-C_4)$-alkyl, $S(O)_r$—$N(R(13))_2$, OR(9), or R(12), or two residues R(25) form a —O—$CH_2$—O-bridge;

R(26) is hydrogen, $(C_1-C_6)$-alkyl, $(C_3-C_7)$-cycloalkyl, $(C_3-C_7)$-cycloalkyl-$(C_1-C_4)$-alkyl, $(C_1-C_6)$-alkoxy, $(C_1-C_6)$-alkylthio, fluoro, chloro, bromo, nitro, $N(R(13))_2$, $(C_1-C_4)$-alkylcarbonyl which is unsubstituted or substituted in the alkyl part by a residue $N(R(13))_2$ or two residues R(26) form a —$(CH_2)_q$-bridge, where q is 3 or 4;

R(27) is $(C_1-C_4)$-alkoxy or phenoxy;

R(28) is $(C_1-C_4)$-alkyl, $(C_1-C_4)$-alkyl, in which 1 to all hydrogen atoms have been replaced by fluorine or chlorine, $(C_1-C_4)$-alkoxy, hydroxy, $SO_2N(R(13))_2$, $N(R(13))_2$, nitro, fluoro, chloro, bromo, or cyano;

R(29) is hydrogen, $(C_1-C_4)$-alkoxycarbonyl, $(C_6-C_{10})$-aryl-$(C_1-C_4)$-alkylcarbonyl, $(C_1-C_4)$-alkylcarbonyl, or $SO_2R(31)$;

R(30) is nitro or $N(R(13))_2$;

R(31) is $(C_1-C_4)$-alkyl, $(C_6-C_{10})$-aryl, which is unsubstituted or substituted by 1, 2, or 3 identical or different substituents which are fluoro, chloro, bromo, or $(C_1-C_4)$-alkoxy;

R(32) is fluoro or NHR(29);

R(34) is $(C_1-C_8)$-alkyl, which is substituted by a residue R(12);

R(35) is hydrogen, $(C_6-C_{10})$-aryl, heteroaryl, $N(R(13))_2$, or $(C_1-C_6)$-alkyl, which is unsubstituted or substituted by a residue $N(R(13))_2$ or cyano;

n is 0, 1, 2 or 3;

m is 0 or 1;

p is 2, 3, 4, or 5;

Q is N or CH;

r is 0, 1, or 2;

s is 0, 1, 2, 3, or 4; with the proviso that s is 2, 3, or 4 if V is oxygen or sulfur;

t is 0, 1, 2, 3, or 4;

V is oxygen, carbonyl, sulfur or a single bond;

$X^-$ is a physiologically acceptable anion;

Y is CH or N;

in all their stereoisomeric forms and mixtures thereof in any ratio, and their physiologically acceptable salts, with the exception of the compounds 2-[2-ethoxycarbonyl-3-(4-isopropyl-phenyl)-propionylamino]-4-methyl-pentanoic acid tert-butyl ester and 2-[2-carboxy-3-(4-isopropyl-phenyl)-propionylamino]4-methyl-pentanoic acid tert-butyl ester and with the proviso that R(6) is R(6a) if R(1) is NR(7a)R(8a).

Alkyl residues present in the compounds of formula I can be saturated or unsaturated and straight-chain or branched. This also applies when they carry substituents or appear as substituents in other residues such as, for example, in alkoxy residues, alkylcarbonyl residues, alkoxycarbonyl residues, heteroalkyl-alkyl residues, cycloalkyl-alkyl residues, arylalkyl residues, heteroarylalkyl residues, and arylalkylcarbonyl residues. Examples of alkyl residues are methyl, ethyl, n-propyl, n-butyl, n-pentyl, n-hexyl, n-heptyl, n-octyl, n-nonyl, n-decyl, isopropyl, isobutyl, isopentyl, isohexyl, isooctyl, isononyl, isodecyl, neopentyl, 3-methylpentyl, sec-butyl, tert-butyl, and tert-pentyl, examples of alkenyl residues are vinyl, 1-propenyl, 2-propenyl (i.e. allyl), butenyl, 3-methyl-2-butenyl, pentenyl, hexenyl, heptenyl, octenyl, nonenyl, decenyl, examples of alkynyl residues are ethynyl, 1-propynyl, 2-propynyl (i.e. propargyl), butynyl, pentynyl and hexynyl.

Cycloalkyl residues present in the compounds of formula I can be mono-, di- or tricyclic and are connected in the ring. This also applies when they carry substituents or appear as substituents in other residues. Examples of cycloalkyl residues are cyclopropyl, methyl-cyclopropyl, ethyl-cyclopropyl, dimethyl-cyclopropyl, propyl-cyclopropyl, methyl-ethyl-cyclopropyl, butyl-cyclopropyl, methyl-propyl-cyclopropyl, diethyl-cyclopropyl, pentyl-cyclopropyl, hexyl-cyclopropyl, heptyl-cyclopropyl, cyclobutyl, methyl-cyclobutyl, ethyl-cyclobutyl, cyclopentyl, methyl-cyclopentyl, ethyl-cyclopentyl, dimethyl-cyclopentyl, propyl-cyclopentyl, butyl-cyclopentyl, methyl-propyl-cyclopentyl, diethyl-cyclopentyl, cyclohexyl, methyl-cyclohexyl, ethyl-cyclohexyl, propyl-cyclohexyl, cycloheptyl, octahydro-indene, bicyclo[4.2.0]octane, octahydro-pentalene, bicyclo[3.3.1]nonane, tetradecahydro-phenanthrene, dodecahydro-phenalene, octahydro-1,4-ethano-indene, tetradecahydro-phenanthrene, adamantyl and methyl-adamantyl, where ethyl, propyl, butyl, pentyl, hexyl and heptyl can be straight-chain or branched as described above.

Examples of heteroalkyl are pyrrolidine, piperidine, tetrahydrofurane, perhydropyrane, tetrahydrothiophene, perhydrothiopyrane, pyrazolidine, imidazolidine, hexahydropyrazine, hexahydropyrimidine, piperazine, dioxolane, perhydrodioxane, oxazolidine, isoxazolidine, thiazolidine, isothiazolidine, perhydro-1,2-oxazine, perhydro-1,3-oxazine, perhydro-1,4-oxazine, perhydro-1,3-thiazine and perhydro-1,4-thiazine. Substituents present in heteroalkyl can be bound to any position unless stated otherwise.

Examples of aryl are phenyl, naphthyl, or 9-fluorenyl residues.

Arylalkyl residues present in the compounds of formula I can consist of an alkyl residue, which can contain one to three aryl moieties. Examples of arylalkyl residues are phenyl-methyl, phenyl-ethyl, phenyl-propyl, phenyl-butyl, naphthyl-methyl, naphthyl-ethyl, naphthyl-propyl, naphthyl-butyl, diphenyl-methyl, diphenyl-ethyl, diphenyl-propyl, diphenyl-butyl, naphthyl-phenyl-methyl, naphthyl-phenyl-butyl, dinaphthyl-butyl, and triphenyl-ethyl.

Examples of heteroaryl residues are pyridyl, pyridazinyl, pyrimidyl, pyrazinyl, furanyl, pyrrolyl, imidazolyl, 1H-pyrazolyl, thiazolyl, oxazolyl, thiophenyl, 1H-benzoimidazolyl, benzothiazolyl, benzofuranyl, indolyl, thieno[3,2-c]pyridinyl, thieno[2,3-c]pyridinyl, furo[3,2-c]pyridinyl, furo[2,3-c]pyridinyl, 3H-imidazo[4,5-c]pyridinyl, [1,2,4]oxadiazolyl, quinolinyl, and isoquinolinyl. The residues can be bound at every possible position.

Examples of pyridyl residues are 2-pyridyl, 3-pyridyl and 4-pyridyl. This also applies to pyridyl residues in which the nitrogen atom is substituted by an alkyl group etc. this substitution leading to a positively charged pyridinium group. This pyridinium group has an $X^-$ as counterion.

In monosubstituted phenyl residues the substituent can be located in the 2-position, the 3-position or the 4-position. If phenyl is substituted twice, the substituents can be in the 2,3-position, the 2,4-position, the 2,5-position, the 2,6-position, the 3,4-position or the 3,5-position. In phenyl residues carrying three substituents the substituents can be in the 2,3,4-position, 2,3,5-position, 2,3,6-position, 2,4,5-position, 2,4,6-position, or 3,4,5-position. In phenyl residues carrying four substituents the substituents can be in the 2,3,4,5-position, 2,3,4,6-position, or the 2,3,5,6-position.

Naphthyl residues can be 1-naphthyl and 2-naphthyl. In substituted naphthyl residues the substituents can be in any position, i.e. in monosubstituted 1-naphthyl residues in the 2-, 3-, 4-, 5-, 6-, 7-, or 8-position and in monosubstitued 2-naphthyl residues in the 1-, 3-, 4-, 5-, 6-, 7-, or 8-position.

Examples of the 5- to 6-membered, saturated or unsaturated, heterocyclic ring that can be formed by the residues R(7) and R(8), R(19) and R(20), or R(19a) and R(20a) together with the nitrogen atom to which they are bound, which can contain a heteroatom of the group N, S, or O are pyrrolidine, piperidine, imidazolidine, 2,3-dihydro-1H-imidazole, thiazolidine, 2,3-dihydro-thiazole, oxazolidine, 2,3-dihydro-oxazole, piperazine, 1,2,3,4-tetrahydro-pyrazine, hexahydro-pyrimidine, 1,2,3,4-tetrahydro-pyrimidine, 1,2-dihydro-pyrimidine, hexahydro-pyridazine, 1,2,3,4-tetrahydro-pyridazine, 1,2,3,6-tetrahydro-pyridazine. Substituents present in this ring can be bound to any position unless stated otherwise.

Examples of a 5- to 6-membered heterocyclic ring which is bound at the nitrogen are piperidine and pyrrolidine.

Examples of a residue of the α-C-atom of a natural amino acid are hydrogen, methyl, isopropyl, butyl, isobutyl, aminobutyl, hydroxymethyl, 1-hydroxyethyl, benzyl, 4-hydroxybenzyl, indol-3-yl-methyl, thiomethyl, methylthioethyl, imidazol-4-ylmethyl, hydroxycarbonylmethyl, hydroxycarbonylethyl, aminocarbonylmethyl, aminocarbonylethyl, and 3-guanidinopropyl.

In compounds of the formula I where two residues R(25) form a O—$CH_2$—O-bridge, the residues are vicinal.

In compounds of the formula I where two residues R(26) form a —$(CH_2)_q$-bridge, the residues are vicinal.

A preferred ($C_6$–$C_{10}$)-aryl-($C_1$–$C_4$)-alkyl residue in compounds of formula I is benzyl (phenylmethyl).

($C_1$–$C_4$)-alkyl means alkyl having 1, 2, 3, or 4 carbon atoms.

($C_1$–$C_6$)-alkyl means alkyl having 1, 2, 3, 4, 5, or 6 carbon atoms.

($C_1$–$C_8$)-alkyl means alkyl having 1, 2, 3, 4, 5, 6, 7, or 8 carbon atoms.

($C_1$–$C_{10}$)-alkyl means alkyl having 1, 2, 3, 4, 5, 6, 7, 8, 9, or 10 carbon atoms.

($C_1$–$C_{12}$)-alkyl means alkyl having 1, 2, 3, 4, 5, 6, 7, 8, 9, 10, 11, or 12 carbon atoms.

($C_6$–$C_{10}$)-aryl means aryl having 6, 7, 8, 9, or 10 carbon atoms.

($C_1$–$C_4$)-alkoxy means alkoxy having 1, 2, 3, or 4 carbon atoms.

($C_1$–$C_6$)-alkylthio means alkylthio having 1, 2, 3, 4, 5, or 6 carbon atoms.

($C_1$–$C_6$)-alkoxy means alkoxy having 1, 2, 3, 4, 5, or 6 carbon atoms.

($C_1$–$C_4$)-alkoxycarbonyl means alkoxycarbonyl having 1, 2, 3, or 4 carbon atoms in the alkoxy part.

($C_1$–$C_6$)-alkoxycarbonyl means alkoxycarbonyl having 1, 2, 3, 4, 5, or 6 carbon atoms in the alkoxy part.

($C_1$–$C_4$)-alkylcarbonyl means alkylcarbonyl having 1, 2, 3, or 4 carbon atoms in the alkyl part.

($C_1$–$C_6$)-alkylcarbonyl means alkylcarbonyl having 1, 2, 3, 4, 5, or 6 carbon atoms in the alkyl part.

($C_6$–$C_{10}$)-aryl-($C_1$–$C_4$)-alkyl means aryl-alkyl having independently from each other 6, 7, 8, 9, or 10 carbon atoms in the aryl part and 1, 2, 3, or 4 carbon atoms in the alkyl part.

($C_6$–$C_{10}$)-aryl-($C_1$–$C_4$)-alkylcarbonyl means aryl-alkylcarbonyl having independently from each other 6, 7, 8, 9, or 10 carbon atoms in the aryl part and 1, 2, 3, or 4 carbon atoms in the alkyl part.

($C_6$–$C_{14}$)-aryl-($C_1$–$C_6$)-alkoxy means aryl-alkoxy having independently from each other 6, 7, 8, 9, 10, 11, 12, 13, or 14 carbon atoms in the aryl part and 1, 2, 3, 4, 5, or 6 carbon atoms in the alkoxy part.

Heteroaryl-($C_1$–$C_4$)-alkyl means heteroaryl-alkyl having 1, 2, 3, or 4 carbon atoms in the alkyl part.

($C_1$–$C_{18}$)-alkylcarbonyloxy-($C_1$–$C_6$)-alkoxycarbonyl means alkylcarbonyloxy-alkoxycarbonyl having independently from each other 1, 2, 3, 4, 5, 6, 7, 8, 9, 10, 11, 12, 13, 14, 15, 16, 17, or 18 carbon atoms in the alkyl part and 1, 2, 3, 4, 5, or 6 carbon atoms in the alkoxy part.

($C_6$–$C_{14}$)-arylcarbonyl means arylcarbonyl having 6, 7, 8, 9, 10, 11, 12, 13, or 14 carbon atoms in the aryl part.

($C_6$–$C_{14}$)-aryloxycarbonyl means aryloxycarbonyl having 6, 7, 8, 9, 10, 11, 12, 13, or 14 carbon atoms in the aryl part.

($C_6$–$C_{14}$)-aryl-($C_1$–$C_6$)-alkoxy means aryl-alkoxy having independently from each other 6, 7, 8, 9, 10, 11, 12, 13, or 14 carbon atoms in the aryl part and 1, 2, 3, 4, 5, or 6 carbon atoms in the alkoxy part.

($C_6$–$C_{14}$)-aryl-($C_1$–$C_6$)-alkoxycarbonyl means aryl-alkoxycarbonyl having independently from each other 6, 7, 8, 9, 10, 11, 12, 13, or 14 carbon atoms in the aryl part and 1, 2, 3, 4, 5, or 6 carbon atoms in the alkoxy part.

($C_3$–$C_7$)-cycloalkyl means cycloalkyl having 3, 4, 5, 6, or 7 carbon atoms.

($C_3$–$C_7$)-cycloalkyl-($C_1$–$C_4$)-alkyl means cycloalkyl-alkyl having independently from each other 3, 4, 5, 6, or 7 carbon atoms in the cycloalkyl part and 1, 2, 3, or 4 carbon atoms in the alkyl part.

($C_3$–$C_{10}$)-cycloalkyl-($C_1$–$C_4$)-alkyl means cycloalkyl-alkyl having independently from each other 3, 4, 5, 6, 7, 8, 9, or 10 carbon atoms in the cycloalkyl part and 1, 2, 3, or 4 carbon atoms in the alkyl part.

It is understood that residues and variables present more than one time in a compound of formula I, e.g. the residues R(8), R(10), R(11), R(12), R(13), R(14), R(15), R(16), R(20), R(20a) R(25), R(26), R(27), R(28), R(32), R(34), and R(35) are independent of one another and can be identical or different.

Physiologically acceptable anions $X^-$, which are present in the compounds of formula I if a positively charged group is present, can be anions derived from suitable inorganic acids or organic carboxylic acids or sulfonic acids. Suitable acids are, in particular, pharmaceutically utilizable or non-toxic salts. Examples of such acids are those given below as examples of acids which can form physiologically acceptable salts with the compounds of formula I containing basic groups. If a compound of formula I contains an anion $X^-$) and simultaneously is present as an acid addition salt formed at a basic group, the anion $X^-$) can be the same or different as the anion introduced by salt formation. The present invention also covers inner salts (or betaines) of the compounds of formula I.

Physiologically acceptable salts of the compounds of formula I are, in particular, pharmaceutically utilizable or non-toxic salts. Such salts are formed, for example, from compounds of formula I which contain acid groups, for example carboxylic acid groups. Examples of such salts are, for example, salts containing cations of alkali metals or alkaline earth metals, such as, for example, sodium, potassium, magnesium or calcium, or the unsubstituted ammonium cation or organic ammonium cations, the latter including cations obtained from physiologically acceptable organic amines, such as, for example, methylamine, ethylamine, triethylamine, ethanolamine, tris(2-hydroxyethyl)amine or amino acids by protonation, or suitable quaternary ammonium cations like, for example, tetramethylammonium.

Compounds of formula I which contain basic groups, for example an amino group, an amidino group or a guanidino group, form acid addition salts with, for example, inorganic acids, organic carboxylic and organic sulfonic acids. Examples of such acids the anions of which can be present in physiologically acceptable salts of the compounds of formula I are hydrochloric acid, hydrobromic acid, sulfuric acid, phosphoric acid, acetic acid, benzoic acid, oxalic acid, malonic acid, succinic acid, maleic acid, fumaric acid, malic acid, tartaric acid, citric acid, methanesulfonic acid, p-toluenesulfonic acid or naphthalenesulfonic acids.

Physiologically acceptable salts of the compounds of formula I can be prepared according to standard procedures, for example by combining the compound of formula I with the desired base, for example an alkaline metal hydroxide or carbonate or hydrogen carbonate or an amine, or with the desired acid in a solvent or diluent. A physiologically acceptable salt of a compound of formula I can also be prepared from another salt, for example trifluoroacetic acid salt by cation exchange or anion exchange by standard procedures. The present invention also covers in general salts of the compounds of formula I which are, for example, obtained during the chemical synthesis of the compounds and which can be used as starting materials for the subsequent preparation of a desired physiologically acceptable salt. The present invention further covers solvates of the compounds of formula I, for example hydrates or alcoholates.

The compounds of formula I according to the invention can contain optically active carbon atoms which independently of one another can have R or S configuration. They can thus be present in the form of individual enantiomers or individual diastereomers or in the form of enantiomeric mixtures including racemates, or diastereomeric mixtures. The present invention relates both to pure enantiomers and mixtures of enantiomers in all ratios and to pure diastereomers and mixtures of diastereomers in all ratios. The invention covers mixtures of two stereoisomers as well as mixtures of more than two stereoisomers of formula I, and all ratios of stereoisomers in the mixtures.

The compounds of formula I can also be present as E isomers or Z isomers. The present invention relates to both pure E and Z isomers and to mixtures of E/Z isomers in all ratios. Diastereomers, including E/Z isomers, can be separated into the individual isomers, for example, by chromatography. Racemates can be separated into the two enantiomers by chromatography on chiral phases or by resolution according to standard procedures. Pure enantiomers can otherwise also be obtained by employing into the synthesis optically active starting materials.

The compounds of formula I according to the invention can further contain mobile hydrogen atoms, i.e. they can be present in various tautomeric forms. The present invention also relates to all these tautomers.

The present invention further covers derivatives of the compounds of formula I in which functional groups are masked or protected by suitable groups, for example common protective groups, as well as other derivatives and prodrugs of the compounds of the formula I and metabolites of the compounds of formula I.

Preferred are compounds of the formula I, wherein

R(1) is NR(7)R(8), OR(9), or NR(7a)R(8a);

R(2) is hydrogen or $(C_1-C_4)$-alkyl, preferably methyl;

R(3) is $(C_6-C_{10})$-aryl-$(C_1-C_4)$-alkyl, preferably benzyl which is substituted in the aryl moiety by a residue R(11), heteroaryl-$(C_1-C_4)$-alkyl, $(C_3-C_7)$-cycloalkyl-$(C_1-C_4)$-alkyl, where heteroaryl, cycloalkyl, or alkyl are unsubstituted or substituted by one, two, or three residues R(11), or heteroalkyl-$(C_1-C_4)$-alkyl, which is unsubstituted or substituted by a residue R(23);

R(4) is hydrogen or $(C_1-C_4)$-alkyl, preferably methyl;

R(5) is $(C_1-C_{10})$-alkyl, preferably butyl, $(C_3-C_7)$-cycloalkyl, preferably cyclohexyl, phenyl, $(C_3-C_7)$-cycloalkyl-$(C_1-C_4)$-alkyl, preferably cyclohexylmethyl, or $(C_6-C_{10})$-aryl-$(C_1-C_4)$-alkyl, preferably benzyl; wherein alkyl and aryl can be substituted by a residue which is hydroxy, benzyloxy, carboxy, N(R(13))$_2$; or a residue of the —C-atom of a natural amino acid, or R(4) and R(5) together form a residue of the formula II

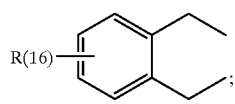
(II)

R(6) is OR(9), R(6a), NR(34)R(13), or

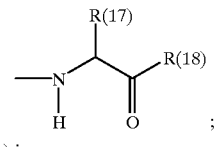

R(6a) is

-continued

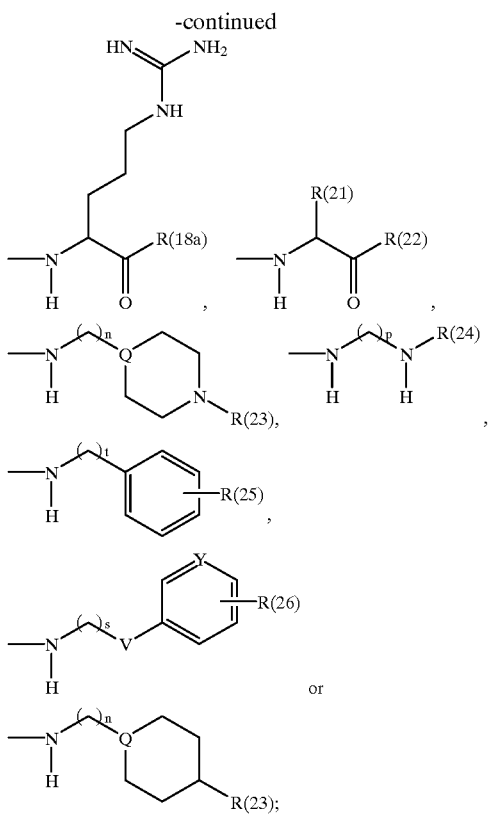

R(7) is (C₁–C₄)-alkyl, preferably methyl or R(8);

R(8) is (C₁–C₆)-alkyl, where alkyl is substituted by 1, 2, or 3 identical or different residues R(10); or R(7) and R(8) together with the nitrogen atom to which they are bound form a 5- or 6-membered, saturated or unsaturated, heterocyclic ring which does not or does contain an additional oxygen atom, and which is unsubstituted or substituted by a residue R(11);

R(7a) and R(8a) are independently of one another hydrogen, (C₁–C₄)-alkyl, preferably methyl or (C₆–C₁₀)-aryl-(C₁–C₄)-alkyl, preferably benzyl;

R(9) is hydrogen or (C₁–C₆)-alkyl;

R(10) is (C₁–C₄)-alkoxy or hydroxycarbonyl;

R(11) is R(12) or heteroaryl, which is unsubstituted or substituted by N(R(9))₂ or (C₁–C₄)-alkyl;

R(12) is N(R(13))₂, COOR(9), CON(R(13))₂, cyano, NR(15)—C(=NR(14))—NHR(15), C(=NR(14))—R(35), —S(O)(NR(13))—N(R(13))₂ or C(=NR(14))—NHR(15);

R(13) is R(15);

R(14) is R(15) or hydroxy;

R(15) is hydrogen, (C₁–C₄)-alkyl, preferably methyl, (C₆–C₁₄)-aryl-(C₁–C₆)-alkoxycarbonyl, preferably benzyloxycarbonyl or (C₁–C₆)-alkoxycarbonyl, preferably tert.-butyloxycarbonyl;

R(16) is hydrogen or (C₁–C₄)-alkyl; preferably hydrogen;

R(17) is (C₁–C₈)-alkyl, which is substituted by a residue R(12);

R(18) is NR(19)R(20);

R(18a) is NR(19a)R(20a);

R(19) and R(20) independently of one another are hydrogen or (C₃–C₇)-cycloalkyl-(C₁–C₄)-alkyl, where alkyl is substituted by an aminocarbonyl residue; or R(19) and R(20) together with the nitrogen atom to which they are bound form a 6-membered, saturated heterocyclic ring, which does not contain or does contain an additional nitrogen atom and which is unsubstituted or substituted by a substituent which is naphthyl-sulfonyl, substituted in the naphtyl-part with chloro, preferably 7-chloro-2-naphthyl-sulfonyl;

R(19a) and R(20a) together with the nitrogen atom to which they are bound form a 6-membered heterocyclic ring, which does not contain or does contain an additional nitrogen atom and which is unsubstituted or substituted by a substituent which is phenyl or SO₂R (31), SO₂R(31) being preferably naphthyl-sulfonyl, which is substituted in the naphtyl-part with chloro, most preferably 7-chloro-2-naphthyl;

R(21) is (C₆–C₁₀)-aryl, (C₆–C₁₀)-aryl-(C₁–C₄)-alkyl or heteroaryl-(C₁–C₄)-alkyl, where and heteroaryl are unsubstituted or substituted independently of one another by a residue R(12) or 1, 2, 3, 4, or 5 residues R(16), the substitution by these residues at a nitrogen atom of the heteroaryl residue leading to a positively charged nitrogen atom having X⁻ as the counterion;

R(22) is OR(9), N(R(13))₂, or a 5-membered nitrogen-containing heterocyclic ring, which is bound at the nitrogen;

R(23) is hydrogen, heteroaryl, which is unsubstituted or substituted by a residue N(R(13))₂; —NH—S(O)(NR (13))—(C₁–C₄)-alkyl, —S(O)(=NR(13))—N(R(13))₂, R(12), or R(14);

R(24) is amidino, R(29), phenyl or 2-pyridyl, which is unsubstituted or substituted by a residue R(30);

R(25) is (C₁–C₄)-alkyl, preferably methyl, which is unsubstituted or substituted with one or two residues R(32); (C₁–C₄)-alkoxycarbonyl, cyano, chloro, CO—N(R(13))₂, N(R(13))₂, SO₂—N(R(13))₂ or R(12);

R(26) is hydrogen, (C₁–C₆)-alkyl, fluoro, chloro, N(R (13))₂ or (C₁–C₄)-alkylcarbonyl which is unsubstituted or substituted in the alkyl part by a residue N(R(13));

R(29) is hydrogen, (C₁–C₄)-alkoxycarbonyl, (C₁–C₄)-alkylcarbonyl or SO₂R(31);

R(30) is nitro;

R(31) is (C₁–C₄)-alkyl, preferably methyl or (C₆–C₁₀)-aryl, preferably phenyl, which is unsubstituted or substituted by 1 or 2 substituents which are chloro;

R(32) is NHR(29);

R(34) is (C₁–C₈)-alkyl, which is substituted by a residue R(12);

R(35) is hydrogen, (C₆–C₁₀)-aryl, heteroaryl, N(R(13))₂, or (C₁–C₆)-alkyl, which is unsubstituted or substituted by a residue N(R(13))₂ or cyano;

n is 0, 1, or 2;

p is 2, 3, or 4;

Q is N or CH;

s is 0, 1 or 2; with the proviso that s is 2 if V is oxygen;

t is 0, 1, 2 or 3;

V is oxygen, carbonyl, or a single bond;

X⁻ is a physiologically acceptable anion;

Y is CH or N;

in all their stereoisomeric forms and mixtures thereof in any ratio, and their physiologically acceptable salts, with the exception of the compounds 2-[2-ethoxycarbonyl-3-(4-isopropyl-phenyl)-propionylamino]4-methylpentanoic acid tert-butyl ester and 2-[2-carboxy-3-(4-isopropyl-phenyl)-propionylamino]4-methyl-pentanoic acid tert-butyl ester;

and with the proviso that R(6) is R(6a) if R(1) is NR(7a)R(8a).

Further preferred are compounds of formula I, wherein R(1) is NR(7)R(8) or NR(7a)R(8a) and where the meaning of R(2), R(3), R(4), R(5) and R(6) is as mentioned above, in all their stereoisomeric forms and mixtures thereof in any ratio, and their physiologically acceptable salts.

Particular preferred are compounds of formula I, wherein

R(1) is NR(7)R(8) or NR(7a)R(8a),

R(2) is hydrogen;

R(3) is $(C_6-C_{10})$-aryl-$(C_1-C_4)$-alkyl, preferably benzyl, which is substituted in the aryl-moiety by a residue R(11);

R(4) is hydrogen;

R(5) is $(C_3-C_7)$-cycloalkyl, preferably cyclohexyl, $(C_6-C_{10})$-aryl, preferably phenyl, or $(C_1-C_6)$-alkyl, preferably butyl;

R(6) is R(6a), NR(34)R(13), or

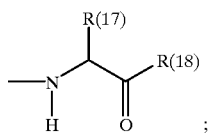

R(6a) is

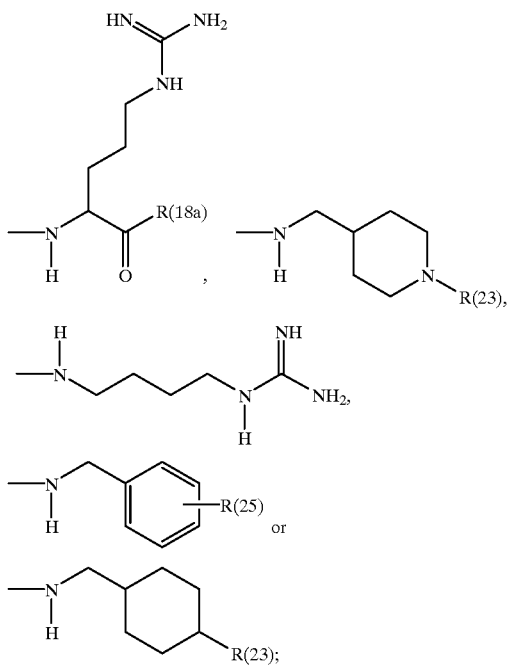

R(7) and R(8) together with the nitrogen atom to which they are bound form a 6-membered, saturated, heterocyclic ring which does not or does contain an additional oxygen atom;

R(7a) and R(8a) are independently of one another hydrogen, $(C_1-C_4)$-alkyl, preferably methyl, or $(C_6-C_{10})$-aryl-$(C_1-C_4)$-alkyl, preferably benzyl;

R(11) is R(12);

R(12) is NR(15)—C(=NR(14))—NHR(15), C(=NR(14))—R(35) or C(=NR(14))—NHR(15);

R(13) is R(15);

R(14) is R(15);

R(15) is hydrogen or $(C_1-C_4)$-alkyl, preferably methyl,

R(17) is $(C_1-C_8)$-alkyl, which is substituted by a residue R(12);

R(18) is NR(19)R(20);

R(18a) is NR(19a)R(20a)

R(19) and R(20) are hydrogen;

R(19a) and R(20a) together with the nitrogen atom to which they are bound form a 6-membered heterocyclic ring, which does contain an additional nitrogen atom and which is substituted by one substituent which is phenyl, or naphthyl-sulfonyl which is substituted in the naphtyl-part with chloro, preferably 7-chloro-2-naphthyl;

R(23) is R(12);

R(25) is R(12);

R(34) is $(C_1-C_6)$-alkyl, which is substituted by C(=NR(14))—NHR(15);

R(35) is $N(R(13))_2$, or $(C_1-C_4)$-alkyl;

in all their stereoisomeric forms and mixtures thereof in any ratio, and their physiologically acceptable salts;

with the proviso that R(6) is R(6a) if R(1) is NR(7a)R(8a).

Especially preferred compounds of formula I are those wherein two or more residues in the formula I have the preferred meanings indicated above, all possible combinations of the preferred meanings being comprised.

Further preferred are compounds of the formula I, wherein

R(6) is R(6a), NHR(34) or

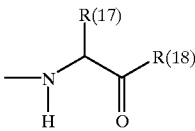

R(6a) is

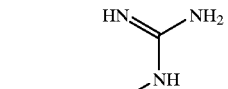

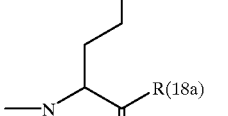

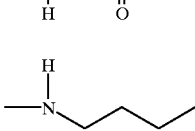

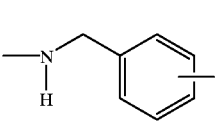

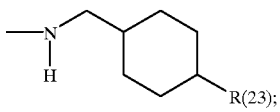

R(12) is NR(15)—C(=NR(14))—NHR(15), C(=NR(14))—R(33) or C(=NR(14))—NHR(15);

R(13) is R(15);

R(14) is R(15);

R(15) is hydrogen or $(C_1-C_4)$-alkyl, preferably methyl,

R(17) is $(C_1-C_8)$-alkyl, which is substituted by a residue R(12);

R(18) is NR(19)R(20);

R(18a) is NR(19a)R(20a);

R(19) and R(20) are hydrogen; R(19a) and R(20a) together with the nitrogen atom to which they are bound form a 6-membered heterocyclic ring, which does contain an additional nitrogen atom and which is substituted by one substituent which is phenyl, or naphthyl-sulfonyl which is substituted in the naphtyl-part with chloro, preferably 7-chloro-2-naphthyl;

R(23) is R(12);

R(25) is R(12);

R(34) is $(C_1-C_6)$-alkyl, which is substituted by C(=NR(14))—NR(15);

R(35) is $N(R(13))_2$, or $(C_1-C_4)$-alkyl;

and wherein the meaning of R(1), R(2), R(3), R(4) and R(5) is as mentioned above, in all their stereoisomeric forms and mixtures thereof in any ratio, and their physiologically acceptable salts with the proviso that R(6) is R(6a) if R(1) is NR(7a)R(8a).

Preferred are also compounds of the formula I, wherein R(1) is NR(7)R(8) or NR(7a)R(8a); with R(7a) and R(8a) are both $CH_3$ or R(7a) is benzyl and R(8a) is hydrogen or $CH_3$ and R(7) and R(8) together with the nitrogen atom to which they are bound form a morpholine or piperidine, and wherein the meaning of R(2), R(3), R(4), R(5) and R(6) is as mentioned above in all their stereoisomeric forms and mixtures thereof in any ratio, and their physiologically acceptable salts. Those compounds are particular preferred if additionally R(2) and R(4) are hydrogen, R(3) is benzyl which is substituted in the aryl part with an amidine group, R(5) is n-butyl, tert. butyl, cyclohexyl, phenyl or benzyl and where the meaning of R(6) is as mentioned above.

Further preferred are compounds of formula I, wherein R(3) is benzyl which is substituted in the aryl part with an amidino group and where the meaning of R(1), R(2), R(4), R(5) and R(6) is as mentioned above, in all their stereoisomeric forms and mixtures thereof in any ratio, and their physiologically acceptable salts.

Particular preferred compounds which may be mentioned are:

N-Benzyl-2-(4-carbamimidoyl-benzyl)-N'-{(S)-cyclohexyl-[4-guanidino-1-(S)-(4-phenyl-piperazine-1-carbonyl)-butylcarbamoyl]-methyl}-malonamide, less polar diastereomer 2-(R,S)-(4-Carbamimidoyl-benzyl)-N-[(4-carbamimidoyl-benzylcarbamoyl)-(S)-cyclohexyl-methyl]-N',N'-dimethyl-malonamide 2-(S)-[2-(R,S)-(4-Carbamimidoyl-benzyl)-3-morpholin-4-yl-3-oxo-propionylamino]-hexanoic acid (1-(S)-carbamoyl-4-guanidino-butyl)-amide 2-(S)-{2-(S)-[2-(R,S)-(4-Carbamimidoyl-benzyl)-3-morpholin-4-yl-3-oxo-propionylamino]-2-phenyl-acetylamino}-5-guanidino-pentanoic acid amide 2-(S)-{2-(S)-[2-(4-Carbamimidoyl-benzyl)-3-oxo-3-piperidin-1-yl-propionylamino]-2-cyclohexyl-acetylamino}-5-guanidino-pentanoic acid amide, less polar diastereomer 2-(S)-{2-(S)-[2-(4-Carbamimidoyl-benzyl)-3-oxo-3-piperidin-1-yl-propionylamino]-2-phenyl-acetylamino}-5-guanidino-pentanoic acid amide, less polar diastereomer 2-(R,S)-(4-Carbamimidoyl-benzyl)-N-({1-(S)-[4-(7-chloro-naphthalene-2-sulfonyl)-piperazine-1-carbonyl]-4-guanidino-butylcarbamoyl}-(S)-cyclohexyl-methyl)-N',N'-dimethyl-malonamide 2-(R,S)-(4-Carbamimidoyl-benzyl)-N-[(S)-cyclohexyl-(4-guanidino-butyl-carbamoyl)-methyl]-N',N'-dimethyl-malonamide N-Benzyl-2-(R)-(4-carbamimidoyl-benzyl)-N'-[(S)-(4-carbamimidoyl-benzyl-carbamoyl)-cyclohexyl-methyl]-malonamide, less polar diastereomer N-Benzyl-2-(4-carbamimidoyl-benzyl)-N'-{(S)-[(1-carbamimidoyl-piperidin-4-ylmethyl)-carbamoyl]-cyclohexyl-methyl}-N-methyl-malonamide, less polar diastereomer 2-(4-Carbamimidoyl-benzyl)-N-{(S)-[(1-carbamimidoyl-piperidin-4-ylmethyl)-carbamoyl]-cyclohexyl-methyl}-N',N'-dimethyl-malonamide, less polar diastereomer 2-(4-Carbamimidoyl-benzyl)-N-{(S)-[(4-carbamimidoyl-cyclohexylmethyl)-carbamoyl]-cyclohexyl-methyl}-N',N'-dimethyl-malonamide N-Benzyl-2-(4-carbamimidoyl-benzyl)-N'-{(S)-[(4-carbamimidoyl-cyclohexylmethyl)-carbamoyl]-cyclohexyl-methyl}-N-methyl-malonamide, less polar diastereomer N-Benzyl-2-(4-carbamimidoyl-benzyl)-N'-(S)-(cyclohexyl-{[1-(1-imino-ethyl)-piperidin-4-ylmethyl]-carbamoyl}-methyl)-N-methyl-malonamide, less polar diastereomer N-Benzyl-2-(4-carbamimidoyl-benzyl)-N'-(S)-(cyclohexyl-{[1-(1-imino-propyl)-piperidin-4-ylmethyl]-carbamoyl}-methyl)-N-methyl-malonamide, less polar diastereomer and/or their physiologically acceptable salts.

The compounds of formula I can be prepared by utilizing procedures and techniques well known and appreciated by one of ordinary skill in the art. Starting materials or building blocks for use in the general synthetic procedures that can be applied in the preparation of the compounds of formula I are readily available to one of ordinary skill in the art. In many cases they are commercially available or have been described in the literature. Otherwise they can be prepared from readily available precursor compounds analogously to procedures described in this application.

Compounds of the formula I can be prepared, for example, by method A described in the schemes 2, 3 and 4, where the residues R(1), R(2), R(3), R(4), R(5), R(6), R(7), R(7a), R(8), R(8a), R(9), are defined as indicated above.

Scheme 2

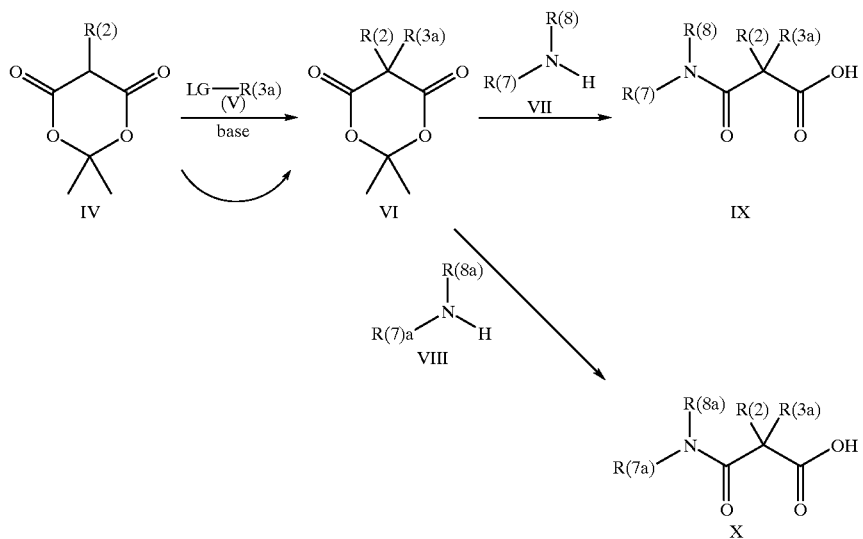

Meldrum acid (R(2) is hydrogen) or alkylated meldrum acid (R(2) is ($C_1$–$C_4$)-alkyl) IV can be alkylated by using base for example potassium carbonate, sodium hydrate, or triethylamine and V, wherein R(3a) is ($C_6$–$C_{10}$)-aryl-($C_1$–$C_4$)-alkyl which is substituted by R(27); heteroaryl-($C_1$–$C_4$)-alkyl, ($C_3$–$C_7$)-cycloalkyl-($C_1$–$C_4$)-alkyl, where heteroaryl, cycloalkyl, or alkyl are unsubstituted or substituted by one, two, or three residues R(27), or heteroalkyl-($C_1$–$C_4$)-alkyl, which is unsubstituted or substituted by a residue R(23); wherein R(23) is as defined above;

R(27) is ($C_1$–$C_4$)-alkyl or R(28), where alkyl can be substituted by R(28);

R(28) is N(R(29))$_2$, nitro, chloro, or cyano, and where residues R(28), if present more than one time in the molecule, are independent of each other and can be identical or different;

R(29) is ($C_1$–$C_6$)-alkyl, ($C_6$–$C_{10}$)-aryl-($C_1$–$C_4$)-alkyl, ($C_1$–$C_6$)-alkylcarbonyl, or ($C_1$–$C_6$)-alkoxycarbonyl, and where residues R(29), if present more than one time in the molecule, are independent of each other and can be identical or different;

and wherein LG is a leaving group like a halogen or a substituted hydroxy group like tosyloxy or mesyloxy;

to give VI, or by condensation of meldrum acid (R(2) is hydrogen) IV with the aldehyde Va in presence of a reducing agent for example sodiumcyanoborohydride, wherein R(3b) is ($C_6$–$C_{10}$)-aryl or ($C_6$–$C_{10}$)-aryl-($C_1$–$C_3$)-alkyl where the aryl moiety is substituted by R(27);

while ring opening of VI can be achieved by reaction of an amine VII or VIII, preferably in the presence of a silylating agent, for example N,O-bis-(trimethylsilyl)-acetamide in an organic solvent, for example in dichloromethane under reflux to give the malonic acid amides IX or X.

Compounds of the formulae V, Va, VII, and VIII are comercially available or can be prepared by standard procedures, which are known to one skilled in the art.

Scheme 3

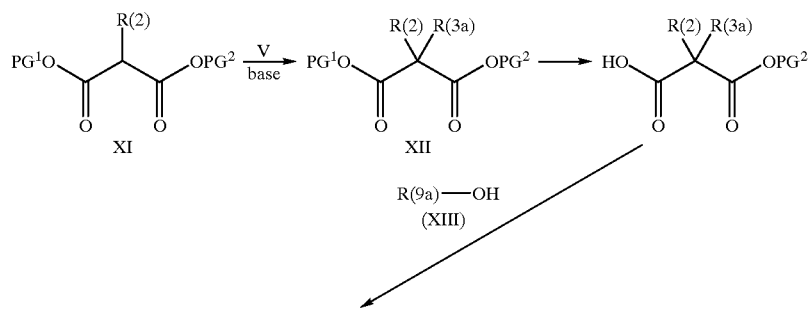

-continued

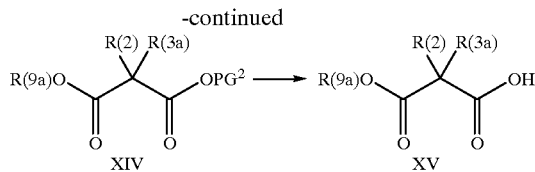

In case of R(1) is OR(9) starting material XI, where PG1 and PG2 are two protecting groups which can be cleaved independently of each other (for example benzyl and tert. butyl), can be alkylated with base, for example by using the same bases as described in scheme 2, and V to give XII, which can be deprotected and esterified with XIII, where R(9a) is $(C_1-C_6)$-alkyl, $(C_6-C_{10})$-aryl, $(C_6-C_{10})$-aryl-$(C_1-C_4)$-alkyl, heteroaryl, or heteroaryl-$(C_1-C_4)$-alkyl; to give XIV and deprotected by standard methods to yield XV.

Compounds of the formula XIII are comercially available or can be prepared by standard procedures which are known to one skilled in the art.

Conversion of R(3a) to R(3) (XVII→XVIII), if necessary, can be made by introduction of a guanidino group or an amidino group as described below, by reduction of a nitro group by hydrogenation with for example Raney-Nickel, palladium/charcoal or other catalysts in the presence of hydrogen, by replacement of a chloro atom by an amino group by reaction of compounds which contain a chloroisochinoline moiety with ammonium acetate in phenol or by other methods well known in the literature, by reaction of an hydroxyamidine moiety with alkyl-chloro-formiate and dehydrogenation with base, for example sodiumcarbonate in water to give the 4H-[1,2,4]oxadiazol-5-one residue, by Scheme 4

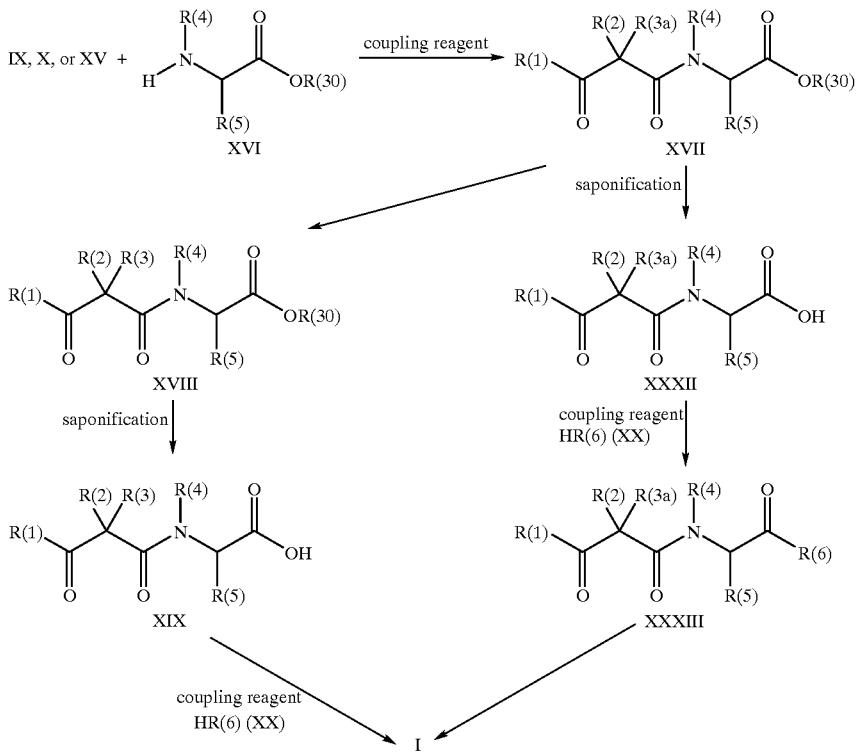

Coupling of IX, X, or XV with XVI, where R(30) is an easily cleavable ester (such as for example $(C_1-C_4)$-alkyl, benzyl, or 4-methoxybenzyl), to yield XVII can be carried out by common coupling reagents used in peptide synthesis. Such coupling reagents are, for example, carbodiimides like dicyclohexylcarbodiimide (DCCI) or diisopropylcarbodiimide (DICI), carbonyidiazoles like carbonyldiimidazole and similar reagents, propylphosphonic anhydride, O-((cyano-(ethoxycarbonyl)-methyleneamino)-N,N,N',N'-tetramethyluronium tetrafluoroborate (TOTU), N-[(dimethylamino)-1H-1,2,3-triazolo[4,5-b]pyridin-1yl-methylene]-N-methylmethanaminium hexafluorophosphate N-oxide (HATU), and many others.

reaction of an hydroxyamidine moiety with acetone under acidic conditions to yield the 5,5-dimethyl-4,5-dihydro-[1,2,4]oxadiazole moiety, or by reaction of an amidine moiety with alkyl chloro formiate to yield the alkyloxycarbonyl protected amidino group.

A guanidino function can be introduced by conversion of an amino function which, for example, may be Qbtained by reduction of a nitro function or a cyano function, using the following reagents:
1. O-Methylisourea (S. Weiss and H. Krommer, Chemiker-Zeitung 98 (1974), 617–618)
2. S-Methylisothiourea (R. F. Borne, M. L. Forrester and I. W. Waters, J. Med. Chem. 20 (1977), 771–776)

3. Nitro-S-methylisothiourea (L. S. Hafner and R. E. Evans, J. Org. Chem. 24 (1959) 1157)
4. Formamidinosulfonic acid (K. Kim, Y.-T. Lin and H. S. Mosher, Tetra. Lett. 29 (1988), 3183–3186)
5. 3,5-Dimethyl-1-pyrazolylformamidinium nitrate (F. L. Scott, D. G. O'Donovan and J. Reilly, J. Amer. Chem. Soc. 75 (1953),4053–4054)
6. N,N'-Di-tert-butyloxycarbonyl-S-methylisothiourea (R. J. Bergeron and J. S. McManis, J. Org. Chem. 52 (1987), 1700–1703)
7. N-Alkoxycarbonyl-,N,N'-dialkoxycarbonyl-,N-alkylcarbonyl- and N,N'-dialkylcarbonyl-S-methylisothiourea (H. Wollweber, H. Kölling, E. Niemers, A. Widdig, P. Andrews, H.-P. Schulz and H. Thomas, Arzneim. Forsch./Drug Res. 34 (1984), 531–542).

Amidines can be prepared from the corresponding cyano compounds by addition of alcohols, for example methanol or ethanol, in acidic anhydrous medium, for example dioxane, methanol or ethanol, and subsequent aminolysis, for example treatment with ammonia in alcohols such as, for example, isopropanol, methanol or ethanol (G. Wagner, P. Richter and Ch. Carbe, Pharmazie 29 (1974), 12–55). Further methods of preparing amidines are the addition of hydrogen sulfide to the cyano group, followed by alkylation, for example methylation, of the resulting thioamide and subsequent reaction with ammonia (GDR Patent No. 235 866), and the addition of hydroxylamine which may be obtained from a hydroxylammonium salt with a base, to the cyano group followed by conversion of the amidoxime to the amidine, for example by catalytic hydrogenation.

Saponification of the ester of compounds of the formula XVIII to give compounds of the formula XIX can be carried out by standard methods. Coupling of XIX with XX to give compounds of the formula I can be carried out with coupling reagents as described above. Compounds of the formula XX are comercially available or can be prepared by standard procedures which are known to one skilled in the art. Another way is the saponification by standard methods of the ester of compounds of the formula XVII to give compounds of the formula XXXII. Coupling of XXXII with XX to give compounds of the formula XXXIII and conversion of the residue R(3a) to R(3) can be done by procedures described above. By this standard procedures functional groups like cyano groups in the residue R(6) can be converted to an amidino group.

Compounds of the formula I can also be obtained by method B as drawn in schemes 5 and 6.

Scheme 5

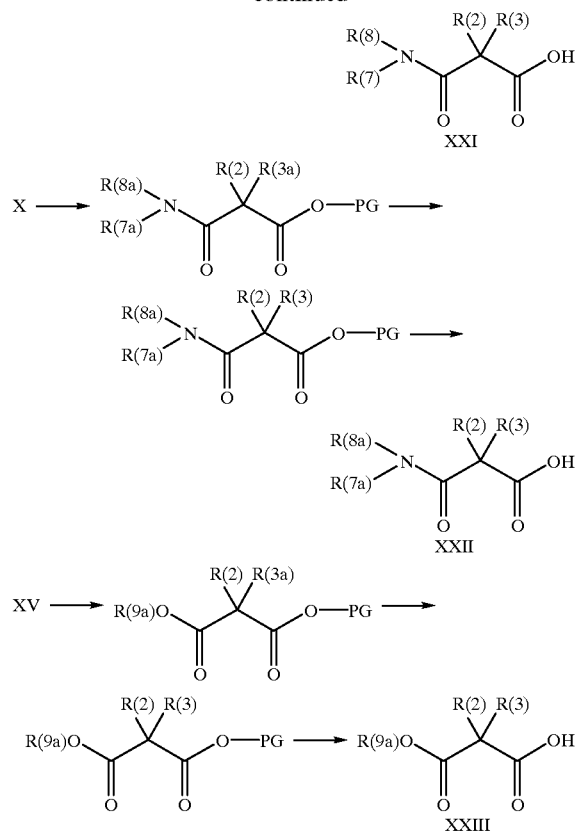

After protection of the carboxylfunction with an easily cleavable protection group (such as for example ($C_1$–$C_4$)-alkyl, benzyl, or 4-methoxybenzyl) by standard methods, the residue R(3a) in compounds of the formulae IX, X, and XV can be transformed to the residue R(3) and deprotected as outlined above to give compounds of the formulae XXI, XXII, and XXIII.

Scheme 6

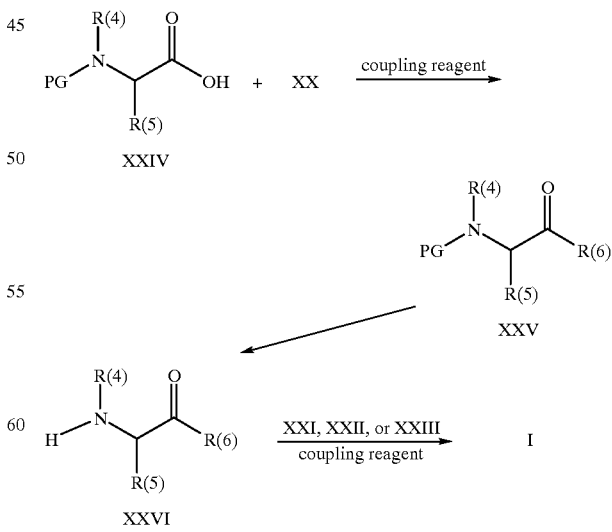

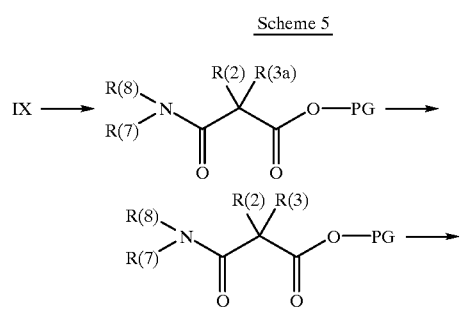

The protected amino acid XXIV, wherein PG is a suitable amino protection group, for example Fmoc, benzyloxycarbonyl (Z), or Boc, preferably Fmoc), can be coupled by standard methods as described above with compounds of the formula XX to give compounds of the formula XXV. Compounds of the formula XXV can be deprotected by standard methods, for example by standard methods for Fmoc-deprotection (L. A. Carpino et al., J. Org. Chem. 1988, 53, 6139–44) to give compounds of the formula XXVI. Compounds of the formula XXVI can be coupled with compounds of the formulae XXI, XXII, or XXIII by standard methods to give compounds of the formula I.

Compounds of the formula I which contain an unsubstituted or substituted amidino, guanidino, or amino residue in the residue R(6) can be synthesized directly by coupling of compounds of the formula XIX or XXIV with compounds of the formula XX or from compounds of formula I which contain the corresponding precursor groups like cyano or amino function. The conversion of the cyano or amino function to the amidino or guanidino function can be done by standard procedures.

Compounds of the formula I can also be obtained by solid phase peptide synthesis (method C) as drawn in scheme 7. Such methods are described, for example, by Steward and Young (Solid Phase Peptide Synthesis (Freeman and Co., San Francisco, 1969), which is incorporated herein by reference. Where solid phase synthesis methods are employed, the chemical composition of a compound can be manipulated while the nascent peptide is attached to the resin or after the peptide has been cleaved from the resin to obtain, for example, an N-terminal derivative. Similar modifications can also be made to a carboxy group of a compound, including a C-terminus carboxy group, which, for example, can be amidated. One skilled in the art can also synthesize a compound of the invention using solution phase organic chemistry.

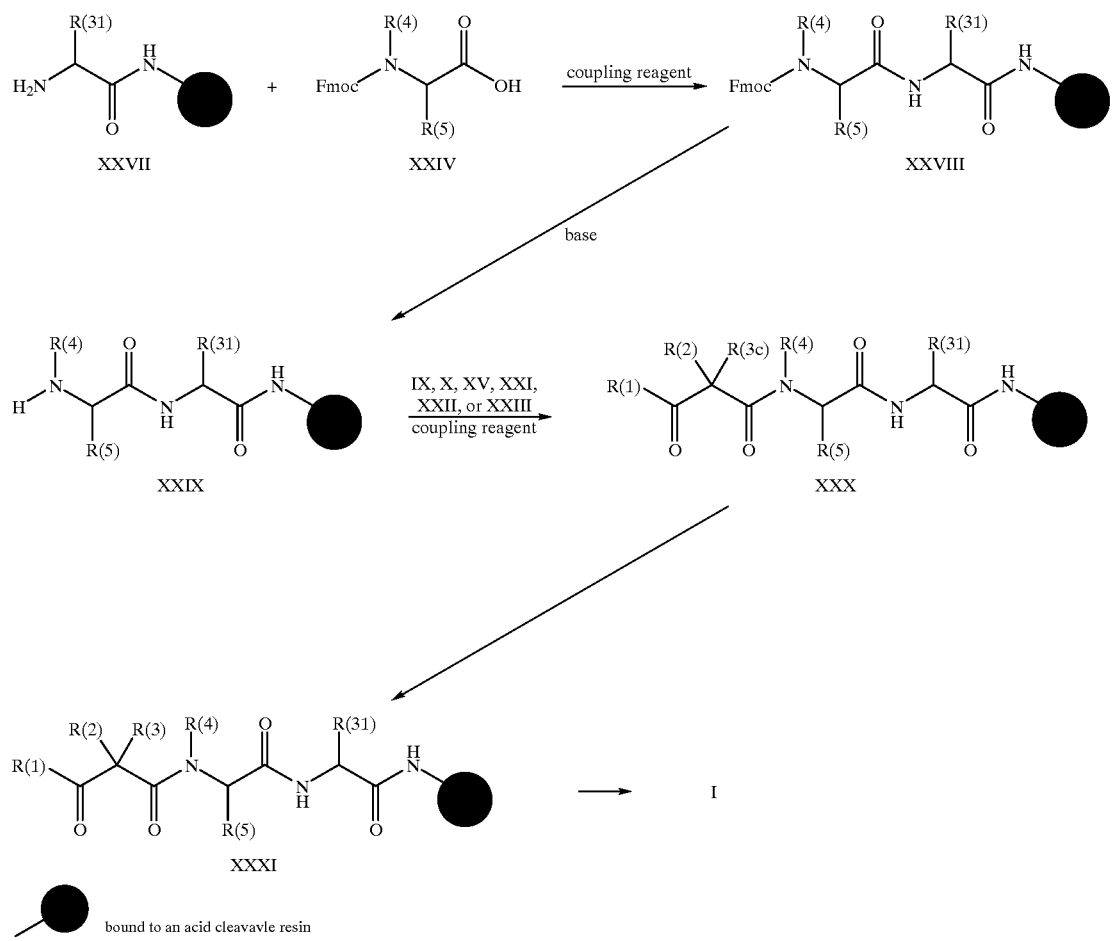

Scheme 7

Using this method (C) (scheme 7) compounds of the formula XXVII, where an amino acid is coupled to a suitable carrier, which are for instance Wang, Trityl or Rink resin or other acid cleavable resins which are known to a person skilled in the art, and wherein R(31) is R(17), R(21), or $(CH_2)_3$—NR(33)—C(=N—R(32))—NH—R(33); wherein R(17) and R(21) are as defined above;

R(32) is R(33), cyano, hydroxy, $(C_1-C_6)$-alkoxy, $(C_6-C_{14})$-aryl-$(C_1-C_6)$-alkoxy which can also be substituted in the aryl moiety, or amino, and where residues R(32), if present more than one time in the molecule, are independent of each other and can be identical or different;

R(33) is hydrogen, $(C_1-C_6)$-alkyl, or $(C_1-C_6)$-alkylcarbonyl;

can be coupled with an Fmoc-protected amino acid XXIV using standard techniques. The resulting dipeptide XXVIII can be deprotected using base, for example a solution of 20–50% of piperidin in dimethylformamide to obtain compounds of the formula XXIX with a primary or secondary amino group, which can be coupled to the building blocks IX, X, XV, XXI, XXII, or XXIII prepared using methods A and B to yield compounds of the formula XXX, where R(3c) has the meaning of R(3) or R(3a). Conversion of the residue R(3a) of the resulting compound XXX, where R(3c) has the meaning of R(3a), to the residue R(3) can be done as described above. Compounds of the formula I can be obtained by cleaving compounds of the formula XXXI under acidic conditions for example trifluoroacetic acid/water in different concentrations depending on the used resin varying from 1% to 95% of trifluoroacetic acid.

These synthesized compounds can be purified using well known methods such as reverse phase-high performance liquid chromatography (RP-HPLC) or other methods of separation based, for example, on the size, charge or hydrophobicity of the compound. Similarly, well known methods such as amino acid sequence analysis or mass spectrometry (MS or HPLC/ESMS) can be used for characterizing the structure of a compound of the invention (see Example 9).

Thus, the present inventions covers a process for the preparation of a compound of formula I, which comprises i)
  a1) alkylating a compound of the formula IV

wherein R(2) is as defined above with a compound of the formula V,

wherein R(3a) is $(C_6-C_{10})$-aryl-$(C_1-C_4)$-alkyl which is substituted in the aryl or alkyl moiety by a residue R(27); heteroaryl-$(C_1-C_4)$-alkyl, $(C_3-C_7)$-cycloalkyl-$(C_1-C_4)$-alkyl, where heteroaryl, cycloalkyl, or alkyl are unsubstituted or substituted by one, two, or three residues R(27), or heteroalkyl-$(C_1-C_4)$-alkyl, which is unsubstituted or substituted by a residue R(23); wherein R(23) is as defined above;

R(27) is R(28) or $(C_1-C_4)$-alkyl, which is unsubstituted or substituted by a residue R(28);
  R(28) is $N(R(29))_2$, nitro, chloro or cyano, and where residues R(28), if present more than one time in the molecule, are independent of each other and can be identical or different;
  R(29) is $(C_1-C_6)$-alkyl, $(C_6-C_{10})$-aryl-$(C_1-C_4)$-alkyl, $(C_1-C_6)$-alkylcarbonyl, or $(C_1-C_6)$-alkoxycarbonyl, and wherein residues R(29), if present more than one time in the molecule, are independent of each other and can be identical or different;

and wherein LG is a leaving group like a halogen or a substituted hydroxy group like tosyloxy or mesyloxy;

in the presence of a base to give a compound of the formula VI,

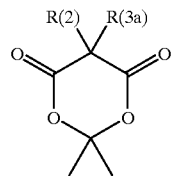

or reacting a compound of the formula IV with a compound of the formula Va,

wherein R(3b) is $(C_6-C_{10})$-aryl or $(C_6-C_{10})$-aryl-$(C_1-C_3)$-alkyl which are substituted by R(27);

in the presence of a reducing agent to give a compound of the formula VI;

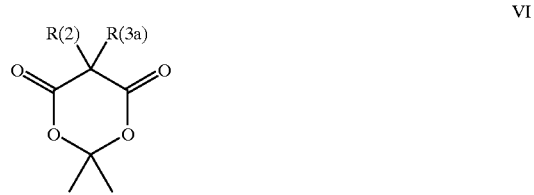

b1) reacting a compound of the formula VI with a compound of the formula VII or VIII,

wherein R(7), R(8), R(7a) and R(8a) are as defined above, to give a compound of the formula IX or X;

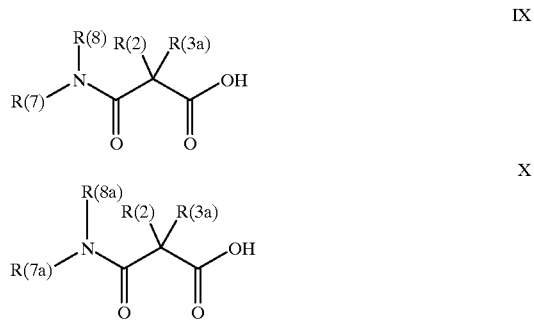

or in case R(1) is OR(9), a2) alkylating a compound of the formula XI,

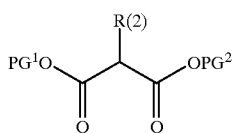

XI wherein R(2) is as defined above and PG1 and PG2 are two protecting groups, which can be cleaved independently of each other, in the presence of a base and a compound of the formula V according to step a1) to give a compound of the formula XII,

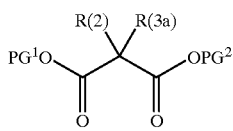

XII b2) deprotecting a compound of the formula XII and esterifying the deprotected compound with a compound of the formula XIII, R(9a)—OH (XIII)

wherein R(9a) is $(C_1-C_6)$-alkyl, $(C_6-C_{10})$-aryl, $(C_6-C_{10})$-aryl-$(C_1-C_4)$-alkyl, heteroaryl, or heteroaryl-$(C_1-C_4)$-alkyl; to give a compound of the formula XIV and XV

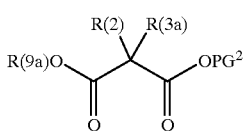

XIV

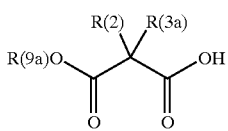

XV b3) subsequently deprotecting a compound of the formula XIV to yield a compound of the formula XV;

c1) coupling of a compound of the formula IX, X, or XV with a compound of the formula XVI,

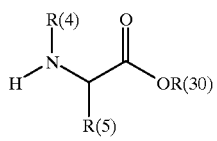

XVI wherein R(4) and R(5) are as defined above and R(30) is an easily cleavable ester to yield a compound of the formula XVII,

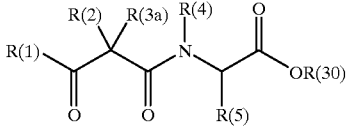

XVII d1) optionally converting a compound of the formula XVII into a compound of the formula XVIII

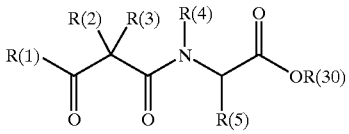

XVIII wherein R(3) is as defined above; for instance by introducing an amidino or guanidino group, by reduction of a nitro group, by replacement of a chloro atom by an amino group, by reaction of compounds which contain a chloroisochinoline moiety with ammonium acetate in phenol, by reaction of a hydroxyamidine moiety with alkyl-chloro-formiate and dehydrogenation with base, for example sodiumcarbonate in water to give the 4H-[1,2,4]oxadiazol-5-one residue, by reaction of a hydroxyamidine moiety with acetone under acidic conditions to yield the 5,5-dimethyl-4,5-dihydro-[1,2,4]oxadiazole moiety, or by reaction of an amidine moiety with alkyl chloro formiate to yield the alkyloxycarbonyl protected amidino group;

e1) saponification of the ester group R(30) in XVII or XVIII and coupling the resulting compound XXXII or XIX according to step c1) with a compound of the formula XX

HR(6)  (XX)

wherein R(6) is as defined above to give a compound of the formula I; or c2) protecting the carboxylfunction in a compound of the formula IX, X or XV with an easily cleavable protecting group and optionally introducing an amidino or guanidino group or reduction of a nitro group according to step d1) to give a compound of the formula XXI, XXII, or XXIII; and

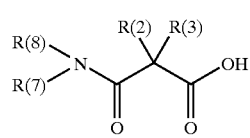

XXI

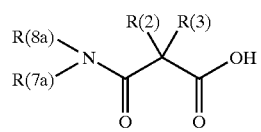

XXII

XXIII

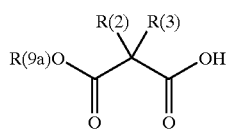

d2) coupling a compound of the formula XXI, XXII or XXIII according to step c1) with a compound of formula XXVI;

XXVI

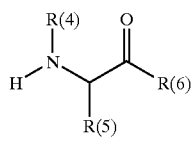

to give a compound of the formula I; or ii)
a) coupling a compound of the formula XXVII,

XXVII

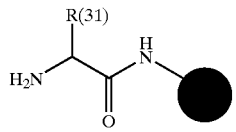

which is bound to a suitable carrier, for example an acid cleavable resin, and wherein
R(31) is R(17), R(21), or $(CH_2)_3$—NR(33)—C(=N—R(32))—NH—R(33);
wherein R(17) and R(21) are as defined above;
R(32) is R(33), cyano, hydroxy, $(C_1-C_6)$-alkoxy, $(C_6-C_{14})$-aryl-$(C_1-C_6)$-alkoxy, which can also be substituted in the aryl moiety, or amino, and where residues R(32), if present more than one time in the molecule, are independent of each other and can be identical or different;
R(33) is hydrogen, $(C_1-C_6)$-alkyl, or $(C_1-C_6)$-alkylcarbonyl;
with a compound of the formula XXIV

XXIV

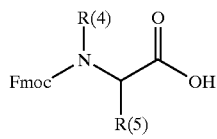

wherein R(4) and R(5) are as defined above to give a compound of the formula XXVI

XXVI

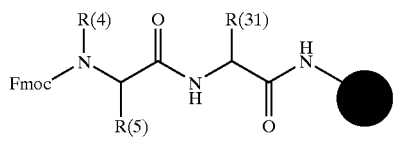

b) and after deprotecting a compound of the formula XXVI with a base coupling the deprotected compound to a compound of the formula IX, X, XV, XXI, XXII, or XXIII to give a compound of the formula XXX;

XXX

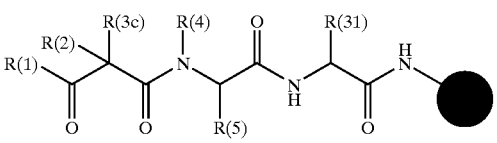

c) optionally converting a compound of the formula XXX to a compound of formula XXXI (i.e. transforming the residue R(3a) to a residue R(3) by introducing an amidino or guanidino group or reduction of a nitro group)

XXXI

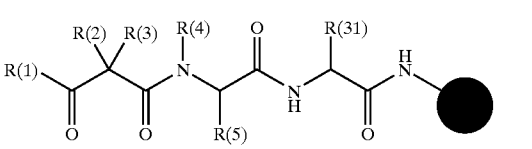

and d) cleaving a compound of the formula XXXI (or XXX) off the resin to give a compound of the formula I.

As is demonstrated in the pharmacological tests described below, the compounds of formula I inhibit factor Xa activity. They can therefore advantageously be used as pharmaceuticals, especially when it is desired to reduce factor Xa activity or to produce effects that can be achieved by inhibiting factor Xa activity in a system, such as influencing coagulation or inhibiting blood clotting. Thus, the present invention also relates to the compounds of formula I for use as pharmaceuticals as well as for the production of medicaments, especially of medicaments for treatment or prophylaxis of the conditions and diseases mentioned below and above. Further, the present invention provides a method of specifically inhibiting factor Xa activity by contacting factor Xa with a compound of formula I. More specifically, an effective amount of a compound of the invention inhibits factor Xa catalytic activity either directly, within the prothrombinase complex or as a soluble subunit, or indirectly, by inhibiting the assembly of factor Xa into the prothrombinase complex. A preferred embodiment of the invention comprises such compounds of the formula I which can inhibit factor Xa activity with a $K_i \leq 100\,\mu M$ and, preferably, with a $K_i \leq 1\,\mu M$.

As used herein, the term "factor Xa activity" refers to the ability of factor Xa, by itself or in the assembly of subunits known as the prothrombinase complex, to catalyze the conversion of prothrombin to thrombin. When used in reference to factor Xa activity, the term "inhibition" includes both the direct and indirect inhibition of factor Xa activity. Direct inhibition of factor Xa activity can be accomplished, for example, by the binding of a compound of formula I to factor Xa or to prothrombinase so as to prevent the binding of prothrombin to the prothrombinase complex active site. Indirect inhibition of factor Xa activity can be accomplished, for example, by the binding of a compound of the invention to soluble factor Xa so as to prevent its assembly into the prothrombinase complex. As used herein, the term "specific" when used in reference to the inhibition of factor Xa activity means that a compound of formula I can inhibit factor Xa activity without substantially inhibiting the activity of other specified proteases, including thrombin (using the same concentration of the inhibitor). Such proteases are involved in the blood coagulation and fibrinolysis cascade.

Inhibition of factor Xa activity or the production of effects achieved by such an inhibition can take place in vivo, i. e. in an individual. As used herein, the term "individual" means a vertebrate, including a mammal such as, for example a mice, a rat, a rabbit, a dog, a pig, a monkey, and especially a human, in which factor Xa is involved in the clotting cascade. It can also take place outside the body of an individual, for example, in an extracorporeal circulation or in the treatment of blood samples from an individual, and generally in vitro. In vitro uses of the compounds of formula I are, for example, the use as a biochemical tool in scientific or analytical investigations or the use for in vitro diagnoses. A compound of formula I can advantageously be used as an anticoagulant, which can be contacted with a blood sample to prevent coagulation. For example, an effective amount of a compound of formula I can be contacted with a freshly drawn blood sample to prevent coagulation of the blood sample.

As used herein, the term "effective amount" when used in this connection means an amount of a compound of formula I that inhibits factor Xa activity to the desired extent. The skilled artisan would recognize that an effective amount of a compound of the invention can be determined using the methods disclosed herein or otherwise known in the art.

In view of the disclosed utility of the compounds of formula I, the skilled artisan also would recognize that an agent such as heparin can be replaced with a compound of the invention. Such a use of a compound of formula I can result, for example, in a cost saving as compared to other anticoagulants.

In a further embodiment, the present invention provides a method of inhibiting factor Xa in a patient in need thereof, comprising administering to said patient an effective factor Xa inhibitory amount of a compound of formula I. As used herein, the term "patient" refers especially to a warm-blooded animal including a mammal and particularly a human. A patient is in need of treatment to inhibit factor Xa when the patient is suffering from a disease state that can be beneficially influenced by inhibiting factor Xa activity or that is expected by the clinician to be beneficially influenced by inhibiting factor Xa acitivity.

The identification of those patients who are in need of treatment to inhibit factor Xa is well within the ability and knowledge of one skilled in the art. A clinician skilled in the art can readily identify, by the use of clinical tests, physical examination and medical/family history, those patients who are in need of such a treatment.

Since a compound of formula I can inhibit factor Xa activity, such a compound can be used for reducing or inhibiting blood clotting in an individual. Thus, the present invention further provides a method of reducing or inhibiting the formation of blood clots in an individual, especially in a patient in need thereof, by administering a therapeutically effective amount of a compound of formula I.

A therapeutically effective amount relating to the production in an individual of an effect like inhibition or reduction of blood clotting, or an effective factor Xa inhibitory amount of a compound of formula I means the amount or the dose of a compound of formula I that has to be administered to an individual in order to achieve or to maintain the desired effect or to inhibit factor Xa activity in the individual to the desired extent. Such an effective amount or dose to be administered has to be adjusted to the individual circumstances in each case. It can be readily determined by the use of conventional techniques using the methods described herein or otherwise Known in the an, and by observing results obtained under analogous circumstances. In determining the effective dose, a number of factors are considered including, but not limited to: the species of patient; its size, age, and general health; the specific disease involved; the degree or the involvement or the severity of the disease; the response of the individual patient; the particular compound administered; the mode of administration; the bioavailability characteristics of the pharmaceutical preparation administered; the dose regimen selected; and the use of comcomitant medication. An appropriate dosage can be established using clinical approaches well known in the medical art.

In general, in view of the above factors it is evident that the effective factor Xa inhibitory amount or the therapeutically effective amount of a compound of formula I will vary and can be varied within wide limits. Usually, an effective amount will vary from about 0.01 milligram per kilogram of body weight per day (mg/kg per day) to about 20 mg/kg per day. A daily dose of from about 0.1 mg/kg to about 10 mg/kg is preferred. These data refer to a human of about 75 kg of body weight. In particular when administering relatively large quantities, it can be favorable to subdivide the daily dose into several, for example 2, 3 or 4 subdose administrations.

A compound of formula I can be administered to an individual for the treatment of a variety of clinical conditions, including, for example, the treatment and prophylaxis of cardiovascular disorders or complications associated, for example, with infection or surgery. Examples of cardiovascular disorders include restenosis, for example restenosis following angioplasty, reocclusion prophylaxis, conditions after coronary bypass operations, arterial, venous and microcirculatory disease states, cardiac infarction, angina pectoris, thromboembolic diseases, thromboses, embolism, adult respiratory distress syndrome, multi-organ failure, stroke or disseminated intravascular coagulation clotting disorder. Examples of related complications associated with surgery include, for example, deep vein and proximal vein thrombosis, which can occur following surgery. Thus, a compound of the invention is useful as a medicament for reducing or inhibiting unwanted coagulation or blood clotting in an individual.

The compounds of formula I, their physiologically acceptable salts and other suitable derivatives thereof can be employed as medicaments or pharmaceuticals in the above-mentioned methods on their own, in mixtures with each other or in the form of pharmaceutical compositions which comprise, as the active ingredient, an effective amount of at least one compound of formula I and/or of a physiologically acceptable salt and/or another suitable derivative thereof in admixture or otherwise in association with one or more pharmaceutically acceptable carrier substances and auxiliary substances.

In effecting treatment of a patient, compounds of formula I on their own or pharmaceutical compositions comprising them can be administered in any form or mode which makes the compounds of formula I bioavailable in effective amounts, including oral and parenteral routes. For example, they can be administered orally, subcutaneously, intramuscularly, intravenously, transdermally, intranasally, rectally, and the like. Oral administration is generally preferred but depending on the specific case other modes of administration can also be favourable, for example in an acute stage of a disease intravenous administration by means of injection or infusion. One skilled in the art of preparing formulations can readily select the proper form and mode of administration depending upon the disease state to be treated, the stage of the disease, and other relevant circumstances.

Pharmaceutical compositions or medicaments comprising a compound of formula I and/or a physiologically acceptable salt and/or another suitable derivative thereof can be made by combining the compounds of formula I and/or their physiologically acceptable salts and/or other suitable derivatives thereof with pharmaceutically acceptable carrier substances and auxiliary substances, the proportion and nature of which are determined by the chosen route of administration and standard pharmaceutical practice. The pharmaceutical compositions or medicaments are prepared in a manner well known in the pharmaceutical art. The pharmaceutical compositions will, in general, contain an effective amount of a compound of formula I and/or a physiologically acceptable salt and/or another suitable derivative thereof together with a suitable amount of a carrier so as to comprise the proper dosage for administration to an individual. The pharmaceutical compositions may be adapted for oral or parenteral use and may be administered to the patient in the form, for example, of tablets, capsules, suppositories, solutions, suspensions, ointments, tinctures, nasal sprays, aerosol mixtures, implants, rods, microcapsules or the like. Thus, together with the claimed compounds the present invention provides useful pharmaceutical compositions or medicaments for inhibiting factor Xa activity and blood clotting in an individual.

The present invention further encompasses a process for the preparation of pharmaceutical compositions or medicaments which comprise at least one compound of formula I and/or a physiologically acceptable salt and/or another suitable derivative thereof, as well as it encompasses the use of the compounds of formula I and/or physiologically acceptable salts and/or other suitable derivatives thereof for the preparation of medicaments, especially of medicaments for the treatment or prophylaxis of the above-mentioned diseases.

Pharmaceutically acceptable carrier and auxiliary substances are referred to as substances or compositions that are non-toxic to an individual or have acceptable toxicity as determined by the appropriate regulatory agency. The carrier substance or excipient may be a solid, semi-solid, or liquid material which can serve as a vehicle or medium for the active ingredient. As used herein, the term "pharmaceutically acceptable carrier" encompasses any of the standard pharmaceutical carriers such as liquid carriers, for example phosphate buffered saline, water, an emulsion such as an oil/water orwater/oil emulsion, or solid or semi-solid carriers such as, for example, lactose, corn starch, fats, waxes, etc. Suitable pharmaceutical carriers and their formulations are well known in the art and are, for example, described by Martin in Remington's Pharmaceutical Sciences, 15th Ed. (Mack Publishing Co., Easton 1975) which is incorporated herein by reference also with respect to other aspects of the ingredients and the preparation of pharmaceutical compositions.

Examples of auxiliary substances are fillers, disintegrants, binders, glidants, wetting agents, stabilizers, emulsifiers, preservatives, sweeteners, dyes, flavorants, aromatizing agents, thickeners, diluents, buffering substances, solubilizing agents, agents for achieving a slow-release effect, salts for altering the osmotic pressure, coating agents, antioxidants, etc.

For the purpose of oral administration, the compounds of formula I may be incorporated with excipients or inert diluents or edible carriers and used in the form of, for example, tablets, film tablets, coated tablets, pills, troches, capsules, granules, solutions, suspensions, emulsions, elixirs, syrups, wafers, chewing gums and the like, or they may be enclosed in gelatin capsule. The pharmaceutical compositions for oral administration may be varied depending upon the particular form. Usually they contain at least 1% of the active ingredient of formula I and may conveniently contain up to about 90% of the weight of the unit. Preferably the content of the compounds of formula I and/or their physiologically acceptable salts and/or other suitable derivatives is from about 4% to about 70% by weight. The amount of the active ingredient present in the compositions is such that a unit dosage form suitable for administration will be obtained.

The tablets, pills, capsules, troches and the like may also contain, for example, one or more of the following carrier and auxiliary substances: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, for example sucrose as a sweetening agent and certain preservatives, dyes and colorings and flavors.

For the purpose of parenteral administration, the compounds of formula I and/or physiologically acceptable salts thereof and/or other suitable derivatives thereof may be incorporated into a solution or a suspension. The solutions or suspensions may, for example, also include one or more of the following carrier and auxiliary substances: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminotetra-acetic acid; buffers such as acetates, citrates or phosphates: agents for the adjustment of toxicity such as sodium chloride or dextrose. The content of the compounds of formula I in the preparations for parenteral adminstration may be varied. Usually they contain at least 0.1% by weight of the compound of formula I. Preferably the content of the compound of formula I and/or the physiologically acceptable salts thereof and/or other suitable derivatives thereof is from about 0.1% to 50%. The parenteral preparations can be enclosed in ampules, disposable syringes, multiple dose vials made of glass or plastic, or infusion bottles. Suitable excipients for microcapsules, implants and rods are, for example, mixed polymers of glycolic acid and lactic acid.

Materials used in preparing the various pharmaceutical compositions should be pharmaceutically pure and non-toxic in the amounts used.

Besides one or more compounds of formula I and/or one or more physiologically acceptable salts thereof and/or one or more other suitable derivatives thereof as active compounds the pharmaceutical compositions according to present invention may also contain one or more other pharmacologically active compounds.

In another, more general embodiment the present invention provides compositions comprising at least one compound of formula I and/or salt thereof and/or another suitable derivative thereof in admixture or otherwise in association with one or more inert carriers. These compositions are useful, for example, as assay standards, as convenient means of making bulk shipments, or as pharmaceutical compositions. An assayable amount of a compound of formula I is an amount which is readily measurable by standard assay procedures and techniques as are well known and appreciated by those skilled in the art. Assayable amount of a compound of formula I will generally vary from about 0.001% to about 90% of the composition by weight. Inert carriers can be any material which does not degrade or otherwise covalently react with a compound of formula I. Examples of suitable inert carriers are water; aqueous buffers, such as, for example, those which are generally useful in High Performance Liquid Chromatography (HPLC) analysis; organic solvents, such as acetonitrile, ethyl acetate, hexane and the like; and pharmaceutically acceptable carrier and auxiliary substances.

The compounds of formula I can also be used as starting materials or chemical intermediates in the preparation of other compounds, especially in the preparation of other pharmacologically active compounds. Examples for such conversions of compounds of the invention into other compounds of the invention are given below. For this use, besides the compounds of formula I and their physiologically acceptable salts also other salts of the compounds of the formula I can be useful which not suitable or less suitable for use as pharmaceuticals. Thus, the present invention also relates to compounds of the formula I and their salts in general as chemical intermediates, especially as intermediates in the preparation of pharmacologically active compounds.

The following tests can serve to investigate the pharmacological activity and to illustrate the utility of the compounds of the present invention as factor Xa inhibitors.

Test 1: In Vitro Inhibition of Selected Purified Coagulation Enzymes and Other Serine Proteases The ability of a compound of formula I to inhibit factor Xa, thrombin, plasmin, elastase and trypsin may be assessed by determining the concentration of compound of formula I that inhibits enzyme activity by 50% ($IC_{50}$). Purified enzymes are used in chromogenic assays. To determine the inhibition constant, the $IC_{50}$ value is corrected for competition with substrate using the formula:

$$K_i = IC_{50} \times (1/\{1+((\text{substrate concentration})/\text{substrate Km})\})$$

where Km is the Michaelis-Menten-constant (Y.-C. Chen and W.H. Prusoff, Biochem. Pharmacol. 22: 3099–3018 (1973), which is incorporated herein by reference).

a. Factor Xa Assay

TBS-PEG buffer (50 mM Tris-Cl, pH 7.8, 200 mM NaCl, 0.05% (w/v) PEG-8000, 0.02% (w/v) $NaN_3$) is used for this assay. The $IC_{50}$ is determined by combining in appropriate wells of a Costar half-area microtiter plate 25 µl human factor Xa (Enzyme Research Laboratories, Inc.; South Bend, Ind.) in TBS-PEG; 40 µl 10% (v/v) DMSO in TBS-PEG (uninhibited control) or various concentrations of the compound to be tested diluted in 10% (v/v) DMSO in TBS-PEG; and substrate S-2765 (N-benzyloxycarbonyl-D-Arg-Gly-L-Arg-p-nitroanilide; Kabi Pharmacia, Inc.; Franklin Ohio) in TBS-PEG.

The assays are performed by pre-incubating the compound of formula I plus enzyme for 10 min, then the assay is initiated by adding substrate to obtain a final volume of 100 µl. The initial velocity of chromogenic substrate hydrolysis is measured by the change in absorbance at 405 nm using a Bio-tek Instruments kinetic plate reader (Ceres UV900HDi) at 25° C. during the linear portion of the time course (usually 1.5 min after addition of substrate). The concentration of inhibitor that causes a 50% decrease in the rate of substrate hydrolysis is predicted by linear regression after plotting the relative rates of hydrolysis (compared to the uninhibited control) versus the log of the compound of formula I concentration. The enzyme concentration is 0.5 nM and substrate concentration is 140 µM.

b. Thrombin Assay

TBS-PEG buffer is used for this assay. The $IC_{50}$ is determined as above for the Factor Xa assay, except that the substrate is S-2366 (L-PyroGlu-L-Pro-L-Arg-p-nitroanilide; Kabi) and the enzyme is human thrombin (Enzyme Research Laboratories, Inc.; South Bend Ind.). The enzyme concentration is 175 µM.

c. Plasmin Assay

TBS-PEG buffer is used for this assay. The $IC_{50}$ is determined as described above for the factor Xa assay, except that the substrate is S-2251 ((D)-Val-L-Leu-L-Lys-p-nitroanilide; Kabi) and the enzyme is human plasmin (Kabi). The enzyme concentration is 5 nM and the substrate concentration is 300 µM.

d. Trypsin Assay

TBS-PEG buffer containing 10 mM $CaCl_2$ is used for this assay. The $IC_{50}$ is determined as described above in the factor Xa assay, except that the substrate is BAPNA (Benzoyl-L-Arg-p-nitroanilide; Sigma Chemical Co.; St. Louis Mo.) and the enzyme is bovine pancreatic trypsin (Type XIII, TPCK treated; Sigma). The enzyme concentration is 50 nM and the substrate concentration is 300 µM.

e. Elastase Assay

Tris-Cl, pH 7.4, 300 mM NaCl, 2% (v/v) N-methylpyrrolidone, 0.01% (w/v) $NaN_3$ buffer is used for this assay. The $IC_{50}$ is determined as described above in the factor Xa assay, except that the substrate is succinyl-Ala-Ala-Ala-p-nitroanilide (Calbiochem-Nova Biochem Corp.; San Diego Calif.) and the enzyme is human neutrophil elastase (Athens Research and Technology, Inc.; Athens Ga.). The enzyme concentration is 75 nM and the substrate concentration is 600 µM. The control compound is "TENSTOP" (N-alpha-tosyl-Gly-p-amidinophenylalanine methyl ester; American Diagnostica, Inc.; Greenwish Conn.), which is a reversible factor Xa inhibitor (Stuerzebecher et al., Thromb. Res. 54: 245–252 (1989); Hauptmann et al., Thromb. Haem. 63: 220–223 (1990), each of which is incorporated herein by reference).

Test 2: Assays for Determining Inhibition of Coagulation

The effectiveness of compounds of formula I may be assessed by the in vitro prothrombin time (PT) assay using pooled human donor plasma. An ex vivo assay may also be used in which plasma is collected at various times after intravenous (iv) administration of a compound of formula I to rats or to rabbits or intraduodenal (id) administration to rats and analysis using the PT assay to determine plasma half-life. The PT assay is initiated with a thromboplastin dilution selected to obtain an extended and highly reproducible coagulation endpoint, referred to as the "dilute PT assay" as described below. The effectiveness of various compounds may also be determined using an in vivo rat arteriovenous shunt model of thrombosis.

a. In Vitro Dilute Prothrombin Time Assay

100 µl prewarmed (37° C.) pooled human platelet poor plasma (PPP) is added to a fibrometer cup (Baxter Diagnostics., Inc.; McGaw Park IL). 50 µl of various concentrations of a compound of formula I in TBS-BSA with calcium (50 mM Tris-Cl, 100 mM NaCl, 0.1% (w/v) bovine serum albumin, 20 mM $CaCl_2$) is added. In control experiments, TBS-BSA with calcium but without test compound of formula I is added for measurement of uninhibited coagulation time. 150 μl diluted prewarmed rabbit thromboplastin (Baxter) with calcium is added to the fibrometer cup and the fibrometer timer is started. A rabbit thromboplastin dilution curve is obtained prior to treating the compound and is used to choose a thromboplastin dilution that allows approximately 30 sec PT time for uninhibited controls. The experimental concentration giving 50% inhibition of coagulation ($EC_{50}$) with test compound is calculated from the dilution curve times.

Alternatively, the dilute prothrombin time assay is conducted using the "research" mode on an Instrumentation Laboratories (IL) ACL3000-plus automated coagulation instrument (IL; Milan, Italy). Thromboplastin is diluted until a clotting time of 30–35 seconds is achieved. This clotting time is taken as 100% activity. A standard curve for calibration is established by serial 2-fold dilution of the diluted thromboplastin reagent (rabbit brain IL-brand thromboplastin). During the assay, a 50 μl sample (plasma separated by centrifugation) is mixed with 100 μl thromboplastin reagent and nephelometric readings are taken over 169 sec. Coagulation time is determined from the maximal rate of change of light scatter calculated by the instrument. Inhibition is expressed as percent activity as determined by comparison with the calibration curve.

b. Ex Vivo Dilute Prothrombin Time Assay

A test compound of formula I is administered iv either through the tail vein (rat) or ear vein (rabbit) following an approved protocol. 0.5 ml blood samples are removed at timed intervals after administration of a test compound of formula I from a cannulated carotid artery (rat) or auricular artery (rabbit). After centrifugation to obtain PPP, the plasma is immediately stored on ice or frozen.

For dilute prothrombin time determination, the plasma is prewarmed and assayed as described above. Percent inhibition is calculated from a thromboplastin dilution curve, which is run with each series of samples, and used to determine the time at which approximately 50% of the initial anticoagulant activity remains in the plasma ($T_{1/2}$).

The test compounds of formula I can also be administered to rats using an intraduodenal dosing protocol. Male Sprague-Dawley rats weighing approximately 300 g are anesthetized with a combination of ketamine/xylazine, subcutaneously, following an approved protocol. The right carotid artery is cannulated for blood sampling. A laparotomy is performed and duodenum is cannulated with a ball-tip needle and tied into place to ensure that the suture is distal to the point of insertion. An additional tie is placed proximal to the insertion point to prevent leakage of gastric contents. The effectiveness of the suture in preventing a compound from reaching the site of insertion is tested by pressure testing at the conclusion of each experiment. The point of insertion is approximately 4 cm from the duodenal-gastric junction. Compounds are administered in 1 ml normal saline. A 0.7 ml blood sample is drawn prior to administration of the test compound of formula I and at 15, 30, 60, 90 and 120 min after administration. Plasma is separated by centrifugation and assayed for inhibition of coagulation using the dilute prothrombin time assay.

c. Rat Arteriovenous Shunt Model of Thrombosis

The anti-thrombotic efficacy of various compounds of the invention may be assessed using rat extracorporeal arteriovenous (AV) shunt. The AV shunt circuit consisted of a 20 cm length of polyethylene (PE) 60 tubing inserted into the right carotid artery, a 6 cm length of PE 160 tubing containing a 6.5 cm length of mercerized cotton thread (5 cm exposed to blood flow), and a second length of PE 60 tubing (20 cm) completeing the circuit into the left jugular vein. The entire circuit is filled with normal saline prior to insertion.

Test compounds of formula I are administered by continuous infusion into the tail vein using a syringe pump and butterfly catheter (infusion volume 1.02 ml/h). A compound is administered for 30 min, then the shunt is opened and blood allowed to flow for period of 15 min (total of 46 min infusion). At the end of the 15 min period, the shunt is clamped and the thread is carefully removed and weighed on an analyktical balance. Percent inhibition of thrombus formation is calculated using the thrombus weight obtained from control rats, which are infused with saline.

The following Table 1 shows the factor Xa inhibitory activities ($K_i$-values) of selected compounds of the formula I (testing the compounds for inhibitory activity was accomplished using the in vitro Factor Xa assay described above (Test 1a).

TABLE 1

Factor Xa inhibitory activity ($K_i$-values):

| Example | $K_i$ (Xa) [μM] |
|---------|-----------------|
| 4 | 0.006 |
| 16 | 0.026 |
| 23 | 0.013 |
| 27 | 0.0035 |
| 28 | 2.0 |
| 35 | 0.084 |
| 40 | 0.50 |
| 41 | 0.0062 |
| 43 | 0.19 |
| 45 | 0.012 |
| 47 | 0.46 |
| 59 | 5.23 |
| 63 | 2.36 |
| 67 | 0.26 |
| 69 | 0.78 |
| 87 | 0.17 |
| 88 | 0.054 |
| 96 | 0.96 |
| 101 | 0.037 |
| 107 | 2.76 |
| 112 | 0.001 |
| 113 | 0.003 |
| 116 | 0.002 |
| 120 | 0.006 |
| 125 | 0.006 |
| 126 | 0.035 |

EXAMPLES

The following examples present typical syntheses of the compounds of formula I. These eamples are understood to be illustrative only and are not intended to limit the scope of the present invention in any way. The compounds of the examples were characterized by mass spectra (MS) andlor NMR spectra andlor melting point.

Example 1

2-(R,S)-4-Carbamimidoyl-benzyl)-N-[(S)-cyclohexyl-(piperidin-4-ylcarbamoyl)-methyl]-N',N'-dimethyl-malonamide Acetic Acid Salt a) (R,S)-4-(2,2-Dimethyl-4,6-dioxo-[1,3]dioxan-5-ylmethyl)-benzonitrile 2,2-Dimethyl-[1,3]dioxane-4,6-dione (114 g, 0.79 mol), 4-formyl-benzonitrile (103.6 g, 0.79 mol) and sodium cyano borohydride (54 g, 0.86 mol) were dissolved in dimethylformamide and stirred at room temperature for 24 hours. The reaction was conduced under argon atmosphere and an efficacious hood. The mixture was poured into 15 l of cold water, acidified with hydrochloric acid (5% strength) to pH 3.8 and the solid separated by filtration and dried. Yield: 100.55 g (49%); mp.: 139–141° C., MS m/z: 260.1 (M+H)⁺.

b) 2-(R,S)-(4-Cyano-benzyl)-N,N-dimethyl-malonamic Acid

Dimethyl-amine hydrochloride (60 g, 735 mmol) and N,O-bis-(trimethylsilyl)-acetamide (80 g, 393 mmol) were stirred under reflux for 3 hours. After cooling to room temperature (R,S)-4-(2,2-dimethyl-4,6-dioxo-[1,3]dioxan-5-ylmethyl)-benzonitrile (20 g, 77 mmol) was added and stirred under reflux for additional 4 hours. After cooling 1 n hydrochloric acid (350 ml) was added slowly, the layers were separated and the organic layer was evaporated. After treatment with ethyl acetate a solid was removed, the organic layer was washed with brine, dried and evaporated. Yield: 16.38 g (86%); MS m/z: 247.2 (M+H)⁺.

c) [3-(4-Cyano-phenyl)-2-(R,S)-dimethylcarbamoyl-propionylamino]-(S)-cyclohexyl-acetic Acid Methyl Ester 2-(R,S)-(4-Cyano-benzyl)-N,N-dimethyl-malonamic acid (10 g, 40.6 mmol) and L-cyclohexylglycine methylester hydrochloride (8.3 g, 40 mmol) were dissolved in dimethylformamide (500 ml). After cooling to −10° C. TOTU (13.1 g, 40 mmol) and diisopropylethylamine (10.34 g, 80 mmol) were added. The mixture was stirred for 1 hour and then allowed to warm to room temperature. After evaporation ethyl acetate was added to the residue and the organic layer was extracted with aqueous sodium hydogen carbonate solution, potassium hydrogen sulfate solution and water. The organic layer was evaporated. Yield: 14.53 g (90%); MS m/z: 400.3 (M+H)⁺.

d) (S)-Cyclohexyl-{2-(R,S)-dimethylcarbamoyl-3-[4-(N-hydroxycarbamimidoyl)-phenyl]-propionylamino}-acetic Acid Methyl Ester

[3-(R,S)-(4-Cyano-phenyl)-2-dimethylcarbamoyl-propionylamino]-(S)-cyclohexyl-acetic acid methyl ester (14 g, 35 mmol), hydroxylamine hydrochloride (7.3 g, 105 mmol) and triethylamine (10.6 g, 105 mmol) were stirred in isopropanol (500 ml) at room temperature for 15 hours. After evaporation ethyl acetate was added to the residue and the organic layer was extracted with water. The organic layer was evaporated and the residue dissolved in dichloromethane. After addition of cyclohexane the separated solid was filtered off and dried. Yield: 13.5 g (89%); MS m/z: 433.4 (M+H)⁺.

e) [3-(4-Carbamimidoyl-phenyl)-2-(R,S)-dimethylcarbamoyl-propionylamino]-(S)-cyclohexyl-acetic Acid Methyl Ester Acetic Acid Salt (S)-Cyclohexyl-{2-(R,S)-dimethylcarbamoyl-3-[4-(N-hydroxycarbamimidoyl)-phenyl]-propionylamino}-acetic acid methyl ester (13 g, 30 mmol) was dissolved in acetic acid (150 ml). After addition of palladium on charcoal (10%, 100 mg) the mixture was hydrogenated at 50° C. for 9 hours. The catalyst was filtered off, the solvent evaporated and the residue dissolved in water and lyophilized. Yield: 14.3 g (100%); MS m/z: 417.4 (M+H)⁺.

f) [3-(4-Carbamimidoyl-phenyl)-2-(R,S)-dimethylcarbamoyl-propionylamino]-(S)-cyclohexyl-acetic Acid

[3-(4-Carbamimidoyl-phenyl)-2-(R,S)-dimethylcarbamoyl-propionylamino]-(S)-cyclohexyl-acetic acid methyl ester acetic acid salt (7 g, 14.7 mmol) was dissolved in a mixture of hydrochloric acid (50 ml) and water (50 ml). After 15 hours stirring at room temperature the mixture was evaporated and after addition of water lyophilized. The residue was purified by chromatography on Sephadex LH20 employing n-butanol (17): glacial acetic acid (1): water (2) as eluent. Pure fractions were combined. The solvent was evaporated, the residue was taken up in water and the aqueous solution was lyophilized. Yield: 4.5 g (76%); MS m/z: 403.3 (M+H)⁺.

g) 2-(R,S)-(4-Cyano-benzyl)-N-{(S)-cyclohexyl-[1-(1-imino-ethyl)-piperidin-4-ylcarbamoyl]-methyl}-N',N'-dimethyl-malonamide Trifluoroacetic Acid Salt EMBEDDCCI (295 mg, 1.4 mmol) was added to a solution of [3-(4-cyanophenyl)-2-(R,S)-dimethylcarbamoyl-propionylamino]-(S)-cyclohexyl-acetic acid (500 mg, 1.3 mmol), 4-(1-imino-ethyl)-cyclohexylamine trifluoroacetic acid salt (478 mg, 1.3 mmol), triethylamine (131 mg, 1.3 mmol) and HOBt (260 mg, 1.3 mmol) in dimethylformamide (20 ml) at 0° C. The mixture was stirred at 0° C. for 1 hour and at 22° C. for 15 hours. The precipitated urea was filtered off and the filtrate was evaporated to give 800 mg (85%) of the desired product. MS m/z: 509.4 (M+H)⁺.

h) 2-(R,S)-(4-Carbamimidoyl-benzyl)-N-[(S)-cyclohexyl-(piperidin-4-ylcarbamoyl)-methyl]-N',N'-dimethyl-malonamide Acetic Acid Salt

EMBED

Dry hydrochloric acid was bubbled into a solution of 2-(R,S)-(4-cyano-benzyl)-N-{(S)-cyclohexyl-[1-(1-imino-ethyl)-piperidin-4-ylcarbamoyl]-methyl}-N',N'-dimethyl-malonamide trifluoroacetic acid salt (800 mg, 1.19 mmol) in ethanol (20 ml) at 0° C. for 7 hours. The mixture was stirred over night and evaporated. The residue was dissoved in ethanol (20 ml) which was saturated with ammonia. After stirring over night the mixture was evaporated. After chromatography on silica gel (dichloro-methane/methanol/water/acetic acid 8:6:1:1) the residue was lyophilized to give 600 mg (97%) of the desired product. MS m/z: 485.4 (M+H)⁺.

Example 2

2-(R,S)-(4-Carbamimidoyl-benzyl)-N-{(S)-cyclohexyl-[1-(1-imino-ethyl)-piperidin-4-ylcarbamoyl]-methyl}-N',N'-dimethyl-malonamide Hydrochloric Acid Salt Acetic Acid Salt A solution of 2-(R,S)-(4-carbamimidoyl-benzyl)-N-[(S)-cyclohexyl-(piperidin-4-ylcarbamoyl)-methyl]-N',N'-dimethyl-malonamide acetic acid salt (150 mg, 0.27 mmol, example 1 h), acetimidic acid ethyl ester (76 mg, 0.62 mmol) and triethylamine (68 mg, 0.67 mmol) in ethanol (6 ml) was stirred over molecular sieves (10 Å) for 3 days. The mixture was filtered and evaporated to give 50 mg (31%) of the desired product. MS m/z: 526.3 (M+H)⁺.

Example 3

N-Benzyl-2-(4-carbamimidoyl-benzyl)-N'-{(S)-cyclohexyl-[4-guanidino-1-(S)-(4-phenyl-piperazine-1-carbonyl)-butylcarbamoyl]-methyl}-malonamide trifluoroacetic acid salt, less polar diastereomer and N-Benzyl-2-(4-carbamimidoyl-benzyl)-N'-{(S)-cyclohexyl-[4-guanidino-1-(S)-(4-phenyl-piperazine-1-carbonyl)-butylcarbamoyl]-methyl}-malonamide trifluoroacetic acid salt, more polar diastereomer a) N-Benzyl-2-(R,S)-(4-cyano-benzyl)-malonamic Acid A solution of benzylamine (58.6 g, 534 mmol), N,O-bis-(trimethylsilyl)-acetamide (71 ml, 90 mmol) and anhydrous dichloromethane (600 ml) was heated to reflux for 3 hours. The reaction mixture was allowed to cool to room temperature and 4-(R,S)-(2,2-dimethyl-4,6-dioxo-[1,3]dioxan-5-ylmethyl)-benzonitrile (15 g, 58 mmol) was added portionwise. The reaction mixture was refluxed for further 3 hours, allowed to cool to room temperature and poured into a cool mixture of 1 l 1 n hydrochloric acid and 500 ml ethyl acetate, acidified to pH 4 with 2 n hydrochloric acid, and extracted with ethyl acetate. The combined organic layers were washed with brine, dried and concentrated in vacuo. The precipitated crystals were sucked off and dried to give 11.07 g (62%) of the desired product. mp.: 152–153° C. (dc), MS m/z: 309 (M+H)$^+$.

b) [2-(R,S)-Benzylcarbamoyl-3-(4-cyano-phenyl)-propionylamino]-(S)-cyclohexyl-acetic Acid Methyl Ester A solution of N-benzyl-2-(R,S)-(4-cyano-benzyl)-malonamic acid (10 g, 32.4 mmol), (S)-amino-cyclohexyl-acetic acid methyl ester (5.94 g, 34.7 mmol), diisopropylethyl-amine (6.45 ml, 37.9 mmol), 3-hydroxy-3H-benzo[d][1,2,3]triazin-4-one (1.32 g, 8.1 mmol), and dimethylformamide (100 ml) was cooled to 10° C. A solution of dicyclohexyl-carbodiimide (7.83 g, 37.9 mmol) in toluene (10 ml) was added dropwise and the reaction mixture stand over night. The precipitated urea was sucked off, the filtrate was evaporated in vacuo, solved in ethyl acetate, washed with saturated sodium hydrogen carbonate-solution and brine, dried, and evaporated in vacuo. Crystallization from n-heptane/isopropanol gave 9.91 g (66%) of the desired product. mp.: 170–174° C., MS m/z: 462 (M+H)$^+$.

c) {2-(R,S)-Benzylcarbamoyl-3-[4-(N-hydroxycarbamimidoyl)-phenyl]-propionylamino}-(S)-cyclohexyl-acetic Acid Methyl Ester A suspension of [2-(R,S)-benzylcarbamoyl-3-(4-cyano-phenyl)-propionylamino]-(S)-cyclohexyl-acetic acid methyl ester (9 g, 19.5 mmol) and hydroxylamine (3.22 g, 97.5 mmol) in ethanol (180 ml) was heated to reflux for 4 hours. The reaction mixture was cooled to room temperature, evaporated in vacuo, solved in ethanol and poured in ice-water. The precipitate was collected by suction and dried at 50° C. in vacuo to give 7.9 g (82%) of the desired product. mp.: 101–104° C., MS m/z: 495 (M+H)$^+$.

d) [2-(R,S)-Benzylcarbamoyl-3-(4-carbamimidoyl-phenyl)-propionylamino]-(S)-cyclohexyl-acetic Acid Methyl Ester {2-(R,S)-Benzylcarbamoyl-3-[4-(N-hydroxycarbamimidoyl)-phenyl]-propionylamino}-(S)-cyclohexyl-acetic acid methyl ester (7.6 g, 15.4 mmol) was hydrogenated in acetic acid with palladium/charcoal to give the desired product which was used without further purification in the next step. mp.: 101–104° C., MS m/z: 479 (M+H)$^+$.

e) [2-(R,S)-Benzylcarbamoyl-3-(4-carbamimidoyl-phenyl)-propionylamino]-(S)-cyclohexyl-acetic Acid The above [2-(R,S)-benzylcarbamoyl-3-(4-carbamimidoyl-phenyl)-propionylamino]-(S)-cyclohexyl-acetic acid methyl ester was suspended in water/concentrated hydrochloric acid (1/1, 200 ml) and stirred at room temperature. After 8 days acetonitrile (100 ml) was added and stirred for 2 more days. The reaction mixture was filtered and poured into ice-water. The precipitate was collected by fractionized crystallization:

Fr.1: 3.36 g (52%, diast. mixture: 6.7% more polar, 78.0% less polar)

Fr.2: 857 mg (13%, diast. mixture: 55.3% more polar, 31.9% less polar), oil

Fr.3: 461 mg (7%, diast. mixture: 3.8% more polar, 93.5% less polar), mp.: 166° C. (subl.)

Fr.4: 455 mg (7%, 96.7% less polar diastereomer), oil

HPLC: more polar diastereomer: 15.62 min, less polar diastereomer: 16.21 min.

HPLC-conditions: Nucleosil 250/4, 7 μM, 1 ml/min, gradient: 100% ($H_2O$+0.1% trifluoroacetic acid) to 100% acetonitrile in 30 min, 100% acetonitrile 5 min, λ=254 nm.

MS of all fractions show: 465 (M+H).

It was tried to purify Fr.1 by flash chromatography on silica gel (dichloromethane/methanol/glacial acetic acid=9/1/0.5), but isomerization of the malonic chiral center took place to give the acetic acid salt of the title compound.

f) N-Benzyl-2-(4-carbamimidoyl-benzyl)-N'-{(S)-cyclohexyl-[4-guanidino-1-(S)-(4-phenyl-piperazine-1-carbonyl)-butylcarbamoyl]-methyl}-malonamide Trifluoroacetic Acid Salt, Less Polar Diastereomer and N-Benzyl-2-(4-carbamimidoyl-benzyl)-N'-{(S)-cyclohexyl-[4-guanidino-1-(S)-(4-phenyl-piperazine-1-carbonyl)-butylcarbamoyl]-methyl}-malonamide Trifluoroacetic Acid Salt, More Polar Diastereomer A solution of [2-(R,S)-benzylcarbamoyl-3-(4-carbamimidoyl-phenyl)-propionylamino]-(S)-cyclohexyl-acetic acid acetic acid salt (100 mg, 0.19 mmol), diisopropylethylamine (95 mg, 0.73 mmol), and N-pmc-N'-[4-amino-5-oxo-5-(4-phenyl-piperazin-1-yl)-pentyl]-guanidine (178 mg, 0.31 mmol) in dimethylformamide (5 ml) was stirred at room temperature for 45 min. Diphenylphosphorylazid (89 mg, 0.32 mmol) was added and the reaction mixture was allowed to stand over night. The reaction mixture was filtered, evaporated in vacuo, and the residue was treated with 10% $Na_2CO_3$-solution and dichloromethane. The organic layer was dried (magnesium sulfate), evaporated in vacuo, solved in a mixture of trifluoroacetic acid/$H_2O$ (95/5), and stirred for 45 min. After lyophilization the residue was purified by MPLC ($H_2O$/ethanol/trifluoroacetic acid=71310.1) to give 14 mg (10%) of F1 (more polar diastereomer) and 12 mg (6%) of F2 (more polar diastereomer/less polar diastereomer=19/65). F1: mp.: 116–118° C., MS m/z: 765 ((M+H)$^+$, 2%), 383.5 ((M+2H)$^{2+}$, 78%), 255.6 ((M+3H)$^{3+}$, 100%). F2: mp.: 130–131° C. MS m/z 765 ((M+H)$^+$, 3%), 383.5 ((M+2H)$^{2+}$, 72%), 255.6 ((M+3H)$^{3+}$, 100%).

Example 4

2-(R,S)-(4-Carbamimidoyl-benzyl)-N-[(4-carbamimidoyl-benzylcarbamoyl)-(S)-cyclohexyl-methyl]-N',N'-dimethyl-malonamide Hydrochloric Acid Salt a) 2-(R,S)-(4-Carbamimidoyl-benzyl)-N-[(4-cyano-benzylcarbamoyl)-(S)-cyclohexyl-methyl]-N',N'-dimethyl-malonamide Acetic Acid Salt To a solution of [3-(4-carbamimidoyl-phenyl)-2-(R,S)-dimethylcarbamoyl-propionylamino]-(S)-cyclohexyl-acetic acid (100 mg, 0.248 mmol, example 1 h) and 4-aminomethyl-benzonitrile hydrochloride (37 mg, 0.22 mmol) in dimethylformamide (10 ml) TOTU (79 mg, 0.24 mmol) and N-ethylmorpholine (50 mg, 0.44 mmol) were added at −15° C. The mixture was stirred for 1 hour and then allowed to warm to room temperature. After evaporation the residue was purified by chromatography on Sephadex LH20 employing n-butanol (17): glacial acetic acid (1): water (2) as eluent. Pure fractions were combined. The solvent was evaporated, the residue was taken up in water and the aqueous solution was lyophilized to yield 83 mg (65%) of the desired product. MS m/z: 517.4 (M+H)$^+$.

b) 2-(R,S)-(4-Carbamimidoyl-benzyl)-N-[(4-carbamimidoyl-benzylcarbamoyl)-(S)-cyclohexyl-methyl]-N',N'-dimethyl-malonamide Hydrochloric Acid Salt Through a solution of 2-(R,S)-(4-carbamimidoyl-benzyl)-N-[(4-cyano-benzylcarbamoyl)-(S)-cyclohexyl-methyl]-N',N'-dimethyl-malonamide acetic acid salt (60 mg, 0.104 mmol) in dry ethanol (15 ml) was passed dry hydrochloric acid gas at −20° C. for 3 hours. The solution was stirred at room temperature for 12 hours, evaporated and treated with a solution of ammonia in dry 2-propanol (15 ml) for 12 hours. After evaporation the residue was purified by chromatography on Sephadex LH20 employing n-butanol (17): glacial acetic acid (1): water (2) as eluent. Pure fractions were combined. The solvent was evaporated, the residue was taken up in water and the aqueous solution was lyophilized to yield 40 mg (60%) of the desired product. MS m/z: 534.4 (M+H)$^+$, 267.8 (M+2H)$^{2+}$.

Example 5

N-Benzyl-2-(R,S)-(4-carbamimidoyl-benzyl)-N'-[(S)-cyclohexyl-(3,5-dichloro-benzylcarbamoyl)-methyl]-malonamide Trifluoroacetic Acid Salt A solution of [2-(R,S)-benzylcarbamoyl-3-(4-carbamimidoyl-phenyl)-propionylamino]-(S)-cyclohexyl-acetic acid hydrochloric acid salt (100 mg, 0.2 mmol), diisopropylethylamine (88 mg, 0.7 mmol), and 3,5-dichloro-benzylamine (53 mg, 0.3 mmol) in dimethylformamide (5 ml) was stirred at room temperature for 1 hour. Diphenylphosphorylazid (82 mg, 0.3 mmol) was added and the reaction mixture was allowed to stand over night. After evaporation in vacuo the residue was treated with 10% $Na_2CO_3$-solution and dichloromethane. The product precipitated between the two layers, was sucked off and purified by HPLC to give 7.6 mg (6%) of the desired product as a diastereomeric mixture. HPLC-conditions: Nucleosil $C_{18}$ 250/21, 7 μM, 4 ml/min, $H_2O$+0.1% trifluoroacetic acid/acetonitrile=50/50, mp.: >230° C., MS m/z: 623 (M+H)$^+$.

Example 6

4-(2-{2-(S)-[2-(R,S)-Benzylcarbamoyl-3-(4-carbamimidoyl-phenyl)-propionylamino]-2-cyclohexyl-acetylamino}-ethyl)-piperazine-1-carboxylic Acid Tert-butyl Ester Trifluoroacetic Acid Salt a) 4-(2-Amino-ethyl)-piperazine-1-carboxylic Acid Tert-butyl Ester A solution of N-tert-butoxycarbonyl-piperazin (5 g, 26.8 mmol), triethylamine (7.44 ml, 53.6 mmol), and chloroethylamine (3.11 g, 26.8 mmol) in dimethylformamide (50 ml) was stirred at room temperature for 72 hours. The reaction mixture was filtered, partitioned between $H_2O$ and ethyl acetate. The aqueous phase was lyophilized, the residue stirred with methanol and the precipitate collected by suction. The precipitate was purified by flash chromatography on silica gel (dichloromethane/methanol/aqueous ammonia=9/1/0.1) to give 1.6 g (26%) of the desired product. MS m/z: 230 ((M+H)$^+$, 91%).

b) 4-(2-{2-(S)-[2-(R,S)-Benzylcarbamoyl-3-(4-carbamimidoyl-phenyl)-propionylamino]-2-cyclohexyl-acetylamino}-ethyl)-piperazine-1-carboxylic Acid Tert-butyl Ester N-ethyl-morpholine (28 μl, 0.22 mmol) and TOTU (78 mg, 0.24 mmol) was added to a solution of [2-benzylcarbamoyl-3-(4-carbamimidoyl-phenyl)-propionylamino]-(S)-cyclohexyl-acetic acid hydrochloric acid salt, (100 mg, 0.2 mmol, example 3 h, less polar diastereomer) in dimethylformamide (4 ml) at −15 to −20° C. After 30 min at that temperature 4-(2-amino-ethyl)-piperazine-1-carboxylic acid tert-butyl ester (55 mg, 0.24 mmol, step a) in dimethylformamide (1 ml) was added and stirred for 2 more hours. The reaction mixture was warmed to room temperature and stand over night. The solvent was evaporated in vacuo, stirred for 2 days with diethyl ether, and the precipitate collected by suction to give the title compound in quantitative yield. mp.: 125–128° C., MS m/z: 676 ((M+H)$^+$, 3%), 339.0 ((M+2H)$^{2+}$, 100%).

Example 7

N-Benzyl-2-(R,S)-(4-carbamimidoyl-benzyl)-N'-[(S)-cyclohexyl-(2-piperazin-1-yl-ethylcarbamoyl)-methyl]-malonamide Trifluoroacetic Acid Salt 4-(2-{2-(S)-[2-(R,S)-Benzylcarbamoyl-3-(4-carbamimidoyl-phenyl)-propionylamino]-2-cyclohexyl-acetylamino}-ethyl)-piperazine-1-carboxylic acid tert-butyl ester (30 mg, 0.04 mmol, example 6b) was treated with a mixture of trifluoroacetic acid/dichloromethane (1/1, 0.5 ml) and stirred for 20 hours. The solvent was evaporated in vacuo and the residue lyophilized to give the desired product. mp.: 196° C. (dc), MS (FAB) m/z: 576.3 ((M+H)$^+$, 100%).

Example 8

2-(4-Carbamimidoyl-benzyl)-N-{(S)-cyclohexyl-[3-(3,5-dichloro-benzenesulfonylamino)-propylcarbamoyl]-methyl}N',N'-dimethyl-malonamide Trifluoroacetic Acid Salt, Less Polar Diastereomer and 2-(4-Carbamimidoyl-benzyl)-N-{(S)-cyclohexyl-[3-(3,5-dichloro-benzenesulfonylamino)-propylcarbamoyl]-methyl}-N',N'-dimethyl-malonamide Trifluoroacetic Acid Salt, More Polar Diastereomer a) N-(3-Amino-propyl)-3,5-dichloro-benzenesulfonamide Trifluoroacetic Acid Salt 3,5-Dichlorobenzenesulfonyl chloride (2.00 g, 8.15 mmol) was added over 3 hours to a solution of 1,3-diaminopropane (6.04 g, 81.5 mmol) and 1,4-dioxan (45 ml) at 15–20° C. under stirring. Stirring was continued for 30 hours at room temperature. The white precipitate formed was sucked off and the filtrate concentrated in vacuo. Water and ethyl acetate were added and the organic layer was separated, dried over magnesium sulfate and concentrated to yield 2 g of crude material. 750 mg of this material was purified by preparative HPLC to yield 675 mg of the title compound after lyophilization. HPLC-conditions: LiChrospher 100, RP-18, 250/25 mm, 5 μM, 15 ml/min, gradient: 100% $H_2O$+0.1% trifluoroacetic acid to 100% acetonitrile in 30 min. MS m/z: 283 ((M+H)$^+$, 100%, 2 $^{35}$Cl), 285 ((M+H)$^+$, 60%, $^{35}$Cl, $^{37}$Cl), 287 ((M+H)$^+$, 14%, 2 $^{37}$Cl).

b) 2-(4-Carbamimidoyl-benzyl)-N-{(S)-cyclohexyl-[3-(3,5-dichloro-benzenesulfonylamino)-propylcarbamoyl]-methyl}-N',N'-dimethyl-malonamide Trifluoroacetic Acid Salt, More Polar Diastereomer and 2-(4-Carbamimidoyl-benzyl)-N-{(S)-cyclohexyl-[3-(3,5-dichloro-benzenesulfonylamino)-propylcarbamoyl]-methyl}-N',N'-dimethyl-malonamide Trifluoroacetic Acid Salt, Less Polar Diastereomer The above sulfonamide (200 mg) was dissolved in ethyl acetate and the resulting solution washed with potassium carbonate solution (5 ml). The organic layer was separated, dried with magnesium sulfate and concentrated. A part of this sulfonamide (8 mg, 0.027 mmol), HOBt hydrate (10 mg, 0.068 mmol) and [3-(R,S)-(4-cyanophenyl)-2-dimethylcarbamoyl-propionylamino]-(S)-cyclohexyl-acetic acid (10 mg, 0.023 mmol, example 1f) were dissolved in dry dichloromethane (1.5 ml) and dimethylformamide (0.5 ml). To this solution DlCl (6 mg, 0.046 mmol) was added under stirring at room temperature. After stirring for 3 hours and standing over night the mixture was concentrated, the residue dissolved in water/ethyl acetate, the organic layer separated and the aqueous layer again extracted with ethyl acetate. The aqueous layer was lyophilized to yield 12 mg of crude material which was purified by preparative HPLC to give two diastereomers: fraction F1, more polar diastereomer (2.5 mg after lyophilization), and fraction F2, less polar diastereomer (2 mg after lyophilization). HPLC-conditions: Nucleosil 250/21 mm, 7 µM, 10 ml/min, gradient: 100% ($H_2O$+0.1% trifluoroacetic acid) to 100% acetonitrile in 30 min. F1: MS m/z: 667 (($M+H$)$^+$, 100%, 2 $^{35}Cl$), 669 (($M+H$)$^+$, 73%, $^{35}Cl$, $^{37}Cl$), 671 (($M+H$)$^+$, 16%, 2 $^{37}Cl$), 334 (($M+2H$)$^{2+}$, 70%, 2 $^{35}Cl$). F2: MS m/z: 667 (($M+H$)$^+$, 67%, 2 $^{35}Cl$), 669 (($M+H$)$^+$, 57%, $^{35}Cl$, $^{37}Cl$), 334 (($M+2H$)$^{2+}$, 100%, 2 $^{35}Cl$), 335 (($M+2H$)$^{2+}$, 75%, $^{35}Cl$, $^{37}Cl$).

Example 9

General Method for Synthesis of Malonic Acid Derivatives on Solid Phase

General solid-phase peptide synthesis was used to produce a part of the compounds of this invention. Such methods are described, for example, by Steward and Young (Solid Phase Peptide Synthesis (Freeman and Co., San Francisco, 1969), which is incorporated herein by reference.

Unless indicated otherwise, compounds were synthesized on polystyrene resin cross-linked with 1% divinylbenzene. An acid sensitive linker (Rink Linker) was coupled to the solid support (Rink, Tetr. Lett. 28:3787 (1987); Sieber, Tetr. Lett. 28:2107 (1987), each of which is incorporated herein by reference). All compounds were synthesized on a semi-automated peptide synthesizer built in house. Boc- and Fmoc-protected L- and D-amino acid derivatives were from various commercial sources like Advanced ChemTech (Louisville, Ky. 40228-9973, USA); Bachem (King of Prussia, Pa. 19406, USA) and PerSeptive Biosystems (Framingham, Mass. 01701, USA). Synthesis of the compounds of formula I was carried out according to the classical Fmoc methodology (E. Atherton and R. C. Sheppard in "Solid Phase Peptide Synthesis: A Practical Approach", IRL Press, Oxford, England, 1989) using DlCl and HOBt as activating reagents. All couplings were done in dimethylformamide or dimethylformamide: dichloromethane (1:1 mixture) at room temperature for 40 min. Completion of coupling was monitored by ninhydrin test as described by Kaiser (Kaiser et al., Anal. Biochem. 34:595 (1970)), which is incorporated herein by reference. A second (double) coupling was performed where coupling in the first instance was incomplete. After completion of peptide assembly on the resin, the final Fmoc deprotection was performed followed by normal wash cycles and determination of the amount of Fmoc group released by deprotection at 302 nm. Then the malonic acid derivatives were similarly coupled by DlCl/HOBt procedure. The finished resin was washed successively with dichloromethane, dimethylformamide and dichloromethane, then dried under vacuo and used in the next step.

Solid-Phase Synthesis of Amidoxime

The general procedure was by mixing the resin (from the step above) of the nitrile containing substance with 20–40 equivalents of hydroxylamine hydrochloride in presence of 1:1:1 (by volumes) mixture of triethylamine, pyridine and dimethylformamide. The suspension was usually sonicated for about 30 sec and shaken at room temperature for 12–24 hours. The completion of conversion of nitrile to amidoxime was monitored by either FT-IR (KBr disk) looking for the disappearance of —CN absorption at 2225 $cm^{-1}$ or by cleavage of small sample of the resin by trifluoroaceticacid: $H_2O$ (95:5) or reagent K (see below) and determination of the molecular weight by HPLC/ESMS. The finished resin was washed with dimethylformamide, 10% $H_2O$ in dimethylformamide, ethanol, dichloromethane and dried in vacuo before its use in the next step.

Solid-Phase Synthesis of Amidine

Several methods are reported for the synthesis of amidine-containing compounds (for review see P. J. Dunn (1995) in "Comprehensive Organic Functional Group Transformations: Amidines and N-Substituted Amidines", Vol. 5, 741–782 (edts. Alan R. Katritzky, Otto Meth-Cohen & Charles W. Rees), Pergamon, N.Y., 1995). None of these methods were compatible with the solid-phase organic synthesis. Here we developed the proper procedure of amidine synthesis via amidoxime precursor by reduction using excess triethylsilane in presence of soluble catalyst (DCRu). It was found that addition of triphenylphosphine in presence of acetic acid facilitated the reduction and enhanced the yield of amidine compounds. Thus, the current invention also relates to a process of the reduction of an amidoxime group on solid phase to an amidino group using excess triethylsilane in presence of the soluble catalyst dichlorotetrakis(triphenylphosphine)ruthenium(II) and optionally further in the presence of triphenylphosphin and acetic acid in a solvent, for example dimethylformamid.

In a typical experiment the dried resin was added to the reduction cocktail composed of DCRu, triphenylphosphine, acetic acid, dimethylformamide and triethylsilane in a stoppered reaction vessel (see example 11). The reduction usually will take 12–24 hours at room temperature. Additional amount of triethylsilan was used in case of incomplete reduction and the time of reaction was extended by 4–8 additional hours.

The finished peptidomimetic resin was washed with dimethylformamide, ethanol, dichloromethane and suspended in reagent K (King et al., Int. J. Pept. Prot. Res. 36:255–266 (1990) cocktail (5 ml/g peptide resin) for 180 min at room temperature. Then the cleavage mixture was filtered in anhydrous diethyl ether and the solid precipitate was isolated by centrifugation and dried in vacuo over solid pellets of KOH and the solid material was dissolved in a mixture of 1:1 of 0.1% trifluoroacetic acid in water and acetonitrile and lyophilized.

For peptidomimetic purification, a sample of crude lyophilized compound was dissolved in a mixture of 0.1% aqueous trifluoroaceticacid containing 10% to 50% acetonitrile. The compound solution usually filtered through a syringe connected to a 0.45 m nylon "ACRODISC" 13 (Gelman Sciences; Ann Arbor Mich.) filter. A proper volume of filtered peptidomimetic solution was injected into a semi-preparative $C_{18}$ column (Vydac Protein and Peptide C18, 218TP1010; The Separation Group; Hesperia Calif.). The flow rate of a gradient or isocratic mixture of 0.1% trifluoroacetic acid buffer and acetonitrile (HPLC grade) as an eluent was maintained using a Beckman "SYSTEM GOLD" HPLC. Elution of the peptidomimetic was monitored by UV detection at 230 nm (Beckman, System Gold, Programmable Solvent Module 126 and Programmable Detector Module 166 controlled by "SYSTEM GOLD" software). After identifying the peak corresponding to each diastereomer using MS, the compounds were collected, lyophilized and biologically tested. MS was performed using a SCIEX API III+ instrument. In addition, NMR was performed using a General Electric instrument (300 MHz) or

Example 10

2-(R,S)-(4-Carbamimidoyl-benzyl)-N-[(1-(S)-carbamoyl-4-guanidino-butylcarbamoyl)-(S)-cyclohexyl-methyl]-2-methyl-malonamic Acid Trifluoroacetic Acid Salt a) 2-(R,S)-(4-Cyano-benzyl)-2-methyl-malonic Acid

2-Methyl-malonic acid diethyl ester (5.25 g, 36 mmol) was mixed with α-Bromo-p-tolunitrile (7.062 g, 36 mmol) in anhydrous dimethylformamide (70 ml). In a separate vessel potassium tert-butoxide (4.4 g, 39 mmol) was dissolved in anhydrous dimethylformamide (30 ml) and added slowly via a syringe to the reaction mixture. The reaction mixture was stirred over night at room temperature. The completion of the reaction was monitored by TLC. After evaporation of dimethylformamide in vacuo, the residue was suspended in 500 ml of 10% aqueous hydrochloric acid and extracted by dichloromethane (2×150 ml). The combined layers were washed with water and dried over magnesium sulfate. After evaporation of dichloromethane the residue was recrystallized from methanol:water to give a white solid with mp.: 84–86° C. This crude diester (2.52 g) was hydrolyzed by lithiumhydroxide in water:tetrahydrofuran and the product (diacid) was extracted with dichloromethane after acidifying slowly with concentrated hydrochloric acid. The organic layer was dried (magnesium sulfate), evaporated, and the residue recrystallized from ether/hexane. The product was a white solid with mp.: 140° C. and characteristic NMR. The compound was used in the next step without further purification.

b) N-[(1-(S)-Carbamoyl-4-guanidino-butylcarbamoyl)-(S)-cyclohexyl-methyl]-2-(R,S)-(4-hydroxycarbamimidoyl-benzyl)-2-methyl-malonamic Acid

EMBED

Dried 2-(S)-amino-2-cyclohexyl-N-(1-(S)-{carbonylamino-(Rink-resin)}-4-[pmc-guanidino]-butyl)-acetamide (1 g, 0.62 mmol) was coupled to 2-(R,S)-(4-cyano-benzyl)-2-methyl-malonic acid (177 mg, 0.75 mmol) in presence of HOBt (189 mg, 1.4 mmol) and diisopropyl-carbodiimide (195 mg, 1.5 mmol) in dimethylformamide (6 ml) and coupling continued over night. The finished peptidomimetic resin was washed and subjected to hydroxylamine reaction as outlined in example 9. The resin was cleaved by trifluoroacetic acid:water (95:5) and lyophilized to give 309.5 mg of the desired product. The compound was used in the next step without further purification and checked by MS to give 560.65 (cal. 560.65).

c) 2-(R,S)-(4-Carbamimidoyl-benzyl)-N-[(1-(S)-carbamoyl-4-guanidino-butylcarbamoyl)-(S)-cyclohexyl-methyl]-2-methyl-malonamic Acid Trifluoroacetic Acid Salt The compound from step b was dissolved in saturated solution of ammonia in methanol (10 ml). To the methanolic solution a Raney nickel slurry (250 μl) was added. The reaction mixture was hydrogenated at 40 psi over night. The reaction mixture was filtered and the solvent evaporated to dryness. The crude amidine compound was purified by HPLC as outlined in example 9. The title compound was identified by MS to give 544.3 (cal. 544.3).

Example 11

3-(2-{2-[2-(4-Carbamimidoyl-benzyl)-3-oxo-3-piperidin-1-yl-propionylamino]-2-(S)-cyclohexyl-acetylamino}-2-(S)-carbamoyl-ethyl)-1-methyl-pyridinium Trifluoroacetic Acid Salt More Polar Diastereomer and 3-(2-{2-[2-(4-Carbamimidoyl-benzyl)-3-oxo-3-piperidin-1-yl-propionylamino]-2-(S)-cyclohexyl-acetylamino}-2-(S)-carbamoyl-ethyl)-1-methyl-pyridiniunt Trifluoroacetic Acid Salt Less Polar Diastereomer and 3-[2-(S)-Carbamoyl-2-(2-(S)-cyclohexyl-2-{2-[4-(N,N'-dimethyl-carbamimidoyl)-benzyl]-3-oxo-3-piperidin-1-yl-propionylamino}-acetylamino)-ethyl]-1-methyl-pyridinium Trifluoroacetic Acid Salt More Polar Diastereomer and 3-[2-(S)-Carbamoyl-2-(2-(S)-cyclohexyl-2-{2-[4-(N,N'-dimethyl-carbamimidoyl)-benzyl]-3-oxo-3-piperidin-1-yl-propionylamino}-acetylamino)-ethyl]-1-methyl-pyridinium Trifluoroacetic Acid Salt Less Polar Diastereomer a) N-[(1-(S)-Carbamoyl-2-pyridin-3-yl-ethylcarbamoyl)-methyl]-2-(R,S)-(4-cyano-benzyl)-3-oxo-3-piperidin-1-yl-propionamide Dried 2-amino-2-cyclohexyl-N-(2-(carbonyl-Rink-resin)-1-pyridin-3-ylmethyl-ethyl)-acetamide (1 g) was coupled to 2-(R,S)-(4-cyano-benzyl)-3-oxo-3-piperidin-1-yl-propionic acid (273 mg, 0.98 mmol) in presence of HOBt (136 mg, 1 mmol) and diisopropyl-carbodiimide (167 mg, 1.3 mmol) in N-methyl-pyrrolidone (5 ml). Coupling was continued over night. The finished peptidomimetic resin was cleaved as outlined in example 9. The lyophilized crude compound weighed 170 mg. Analysis by MS gave of 508.2 (cal. 508.2).

b) 3-(2-{2-[2-(4-Carbamimidoyl-benzyl)-3-oxo-3-piperidin-1-yl-propionylamino]-2-(S)-cyclohexyl-acetylamino}-2-(S)-carbamoyl-ethyl)-1-methyl-pyridinium Trifluoroacetic Acid Salt More Polar Diastereomer and 3-(2-{2-[2-(4-Carbamimidoyl-benzyl)-3-oxo-3-piperidin-1-yl-propionylamino]-2-(S)-cyclohexyl-acetylamino}-2-(S)-carbamoyl-ethyl)-1-methyl-pyridinium Trifluoroacetic Acid Salt Less Polar Diastereomer and 3-[2-(S)-Carbamoyl-2-(2-(S)-cyclohexyl-2-{2-[4-(N,N'-dimethyl-carbamimidoyl)-benzyl]-3-oxo-3-piperidin-1-yl-propionylamino}-acetylamino)-ethyl]-1-methyl-pyridinium Trifluoroacetic Acid Salt More Polar Diastereomer and 3-[2-(S)-Carbamoyl-2-(2-(S)-cyclohexyl-2-{2-[4-(N,N'-dimethyl-carbamimidoyl)-benzyl]-3-oxo-3-piperidin-1-yl-propionylamino}-acetylamino)-ethyl]-1-methyl-pyridinium Trifluoroacetic Acid Salt Less Polar Diastereomer Crude compound (80 mg) from step a was dissolved in triethylamine (3 ml) and pyridine (3 ml), cooled down to 0° C. and saturated with dihydrogensulfide for 30 min to give a clear green solution. The reaction solution was stirred over night at room temperature. After evaporation of the solvent the residue was taken up in acetone (20 ml) and treated with methyl iodide (3 ml). After stirring for 8 hours at room temperature the solvent was concentrated in vacuo and the residue redissolved in methanol (40 ml). To the methanolic solution, ammonium acetate (1.5 g) was added and the mixture was stirred at 60° C. for 1 hour. The reaction mixture was evaporated to dryness, the residue was lyophilized, and purified by HPLC. The isolated compounds gave the following MS: F2 (more polar diastereomer) and F4 (less polar diastereomer): 632 (M⁺, dimethylguanidino diastereomers), and E1 (more polar diastereomer) and E2 (less polar diastereomer): 604 (M⁺, guanidino diastereomers).

The following compounds were synthesized using the procedures described above:

Bruker Avance DPX 300 (300 MHz). For NMR, samples typically were measured in DMSO-$d_6$ or CDCl$_3$ (Aldrich). Typical synthesis of individual compounds is summarized in scheme 7 and the following examples illustrate the experimental details.

| No. | Name | MS | Method |
|---|---|---|---|
| 12 | 2-(S)-{3-(4-Amino-phenyl)-2-(S)-[2-(R,S)-(4-carbamimidoyl-benzyl)-3-morpholin-4-yl-3-oxo-propionylamino]-propionyl-amino}-5-guanidino-pentanoic acid amide trifluoroacetic acid salt | ok | solid ph. |
| 13 | 2-(S)-{[2-(R,S)-(4-Carbamimidoyl-benzyl)-3-morpholin-4-yl-3-oxo-propionyl]-methyl-amino}-3-(S)-methyl-pentanoic acid (1-carbamoyl-4-guanidino-butyl)-amide trifluoroacetic acid salt | ok | solid ph. |
| 14 | 2-(S)-(2-(S)-{[2-(R,S)-(4-Carbamimidoyl-benzyl)-3-morpholin-4-yl-3-oxo-propionyl]-methyl-amino}-3-phenyl-propionyl-amino)-5-guanidino-pentanoic acid amide trifluoroacetic acid salt | ok | solid ph. |
| 15 | 2-[2-(R,S)-(4-Carbamimidoyl-benzyl)-3-morpholin-4-yl-3-oxo-propionyl]-1,2,3,4-tetrahydro-isoquinoline-3-(S)-carboxylic acid (1-(S)-carbamoyl-4-guanidino-butyl)-amide trifluoroacetic acid salt | ok | solid ph. |
| 16 | 2-(S)-[2-(R,S)-(4-Carbamimidoyl-benzyl)-3-morpholin-4-yl-3-oxo-propionyl-amino]-hexanoic acid(1-(S)-carbamoyl-4-guanidino-butyl)-amide trifluoroacetic acid salt | ok | solid ph. |
| 17 | 4-(S)-[2-(R,S)-(4-Carbamimidoyl-benzyl)-3-morpholin-4-yl-3-oxo-propionyl-amino]-4-(1-(S)-carbamoyl-4-guanidino-butyl-carbamoyl)-butyric acid trifluoroacetic acid salt | ok | solid ph. |
| 18 | 2-(S)-{2-(S)-[2-(R,S)-4-Carbamimodoyl-benzyl)-3-morpholin-4-yl-3-oxo-propionyl-amino]-3-naphthalen-2-yl-propionyl-amino}-5-guanidino-pentanoic acid amide trifluoroacetic acid salt | ok | solid ph. |
| 19 | 2-(S)-{2-(S)-[2-(R,S)-(4-Carbamimidoyl-benzyl)-3-morpholin-4-yl-3-oxo-propionyl-amino]-4-phenyl-butyrylamino}-5-guanidino-pentanoic acid amide trifluoroacetic acid salt | ok | solid ph. |
| 20 | 2-(S)-{5-Amino-2-(S)-[2-(R,S)-(4-carbamimidoyl-benzyl)-3-morpholin-4-yl-3-oxo-propionylamino]-pentanoylamino}-5-guanidino-pentanoic acid amide trifluoroacetic acid salt | ok | solid ph. |
| 21 | 3-(S)-[2-(R,S)-(4-Carbamimidoyl-benzyl)-3-morpholin-4-yl-3-oxo-propionyl-amino]-N-(1-(S)-carbamoyl-4-guanidino-butyl)-succinamic acid trifluoroacetic acid salt | ok | solid ph. |
| 22 | 2-(S)-{2-(S)-[2-(R,S)-(4-Carbamimidoyl-benzyl)-3-morpholin-4-yl-3-oxo-propionyl-amino]-3-hydroxy-propionylamino}-5-guanidino-pentanoic acid amide trifluoroacetic acid salt | ok | solid ph. |
| 23 | 2-(S)-{2-(S)-[2-(R,S)-(4-Carbamimidoyl-benzyl)-3-morpholin-4-yl-3-oxo-propionyl-amino]-2-phenyl-acetylamino}-5-guanidino-pentanoic acid amide trifluoroacetic acid salt | ok | solid ph. |
| 24 | 2-(S){-3-Benzyloxy-2-(S)-[2-(R,S)-(4-carbamimidoyl-benzyl)-3-morpholin-4-yl-3-oxo-propionylamino]-propionylamino}-5-guanidino-pentanoic acid amide trifluoroacetic acid salt | ok | solid ph. |
| 25 | [5-(S)-[2-(R,S)-(4-Carbamimidoyl-benzyl)-3-morpholin-4-yl-3-oxo-propionyl-amino]-5-(1-(S)-carbamoyl-4-guanidino-butyl-carbamoyl)-pentyl]-carbamic acid benzyl ester trifluoroaceticacid salt | ok | solid ph. |
| 26 | 4-(S)-[2-(R,S)-(4-Carbamimidoyl-benzyl)-3-morpholin-4-yl-3-oxo-propionyl-amino]-4-[1-(S)-(1-(S)-carbamoyl-2-cyclohexyl-ethyl-carbamoyl)-4-guanidino-butylcarbamoyl]-butyric acidtrifluoroacetic acid salt | ok | solid ph. |
| 27 | 2-(S)-{2-(S)-[2-(4-Carbamimidoyl-benzyl)-3-oxo-3-piperidin-1-yl-propionyl-amino]-2-cyclohexyl-acetylamino}-5-guanidino-pentanoic acid amide, less polar diastereomer | ok | solid ph. |
| 28 | 2-(S)-{2-(S)-[2-(4-Carbamimidoyl-benzyl)-3-oxo-3-piperidin-1-yl-propionyl-amino]-2-cyclohexyl-acetylamino}-5-guanidino-pentanoic acid amide, more polar diastereomer | ok | solid ph. |
| 29 | 2-(4-Carbamimidoyl-benzyl)-N-[(1-(S)-carbamoyl-4-guanidino-butylcarbamo-yl)-(S)-cyclohexyl-methyl]-N',N'-bis-(2-methoxy-ethyl)-malonamide trifluoroacetic acid salt, more polar diastereomer | ok | solid ph. |
| 30 | 2-(4-Carbamimidoyl-benzyl)-N-[(1-(S)-carbamoyl-4-guanidino-butylcarbamoyl)-(S)-cyclohexyl-methyl]-N',N'-bis-(2-methoxy-ethyl)-malonamide trifluoroacetic acid salt, less polardiastereomer | ok | solid ph. |
| 31 | 2-(S)-{2-(S)-[2-(4-Carbamimidoyl-benzyl)-3-oxo-3-piperidin-1-yl-propiony-amino]-2-cyclohexyl-acetylamino}-5-(N',N''-dimethyl-guanidino)-pentanoic acid amide trifluoroacetic acid salt, less polar diastereomer | ok | solid ph. |
| 32 | 6-Amino-2-(S)-{2-(S)-[2-(4-carbamimidoyl-benzyl)-3-oxo-3-piperidin-1-yl-propionyl-amino]-2-cyclohexyl-acetylamino}-hexanoic acid amide trifluoroacetic acid salt, less polar diastereomer | ok | solid ph. |
| 33 | 6-Amino-2-(S)-{2-(S)-[2-(4-carbamimidoyl-benzyl)-3-oxo-3-piperidin-1-yl-propionyl-amino]-2-cyclohexyl-acetylamino}-hexanoic acid amide trifluoroacetic acid salt, more polar diastereomer | ok | solid ph. |
| 34 | 1-(3-(4-Carbamimidoyl-phenyl)-2-{[(S)-(1-(S)-carbamoyl-4-guanidino-butyl-carbamoyl)-cyclohexyl-methyl]-carbamoyl}-propionyl)-pyrrolidine-2-carboxylic acid trifluoroacetic acid salt, more polar diastereomer | ok | solid ph. |
| 35 | 1-(3-(4-Carbamimidoyl-phenyl)-2-{[(S)-(1-(S)-carbamoyl-4-guanidino-butyl-carbamoyl)-cyclohexyl-methyl]-carbamoyl}-propionyl)-pyrrolidine-2-carboxylic acid trifluoroacetic acid salt, less polar diastereomer | ok | solid ph. |
| 36 | 2-(S)-{2-(S)-[2-(4-Carbamimidoyl-benzyl)-3-oxo-3-piperidin-1-yl-propionyl-amino]-2-phenyl-acetylamino}-5-guanidino-pentanoic acid amide trifluoroacetic acid salt, more polar diastereomer | ok | solid ph. |
| 37 | 2-(S)-{2-(S)-[2-(4-Carbamimidoyl-benzyl)-3-oxo-3-piperidin-1-yl-propionyl-amino]-2-phenyl-acetylamino}-5-guanidino-pentanoic acid amide trifluoroacetic acid salt, less polar diastereomer | ok | solid ph. |
| 38 | [3-(4-Carbamimidoyl-phenyl)-2-{[(1-(S)-carbamoyl-4-guanidino-butyl-carbamoyl)-(S)-cyclohexyl-methyl]-carbamoyl}-propionyl)-methyl-amino]-acetic acidtrifluoroacetic acid salt, more polar diastereomer | ok | solid ph. |
| 39 | [3-(4-Carbamimidoyl-phenyl)-2-{[(1-(S)-carbamoyl-4-guanidino-butyl-carbamoyl)-(S)-cyclohexyl-methyl]-carbamoyl}-propionyl)-methyl-amino]-acetic acidtrifluoroacetic acid salt, less polar diastereomer | ok | solid ph. |
| 40 | 2-(S)-{2-(S)-[2-(R,S)-(4-Carbamimidoyl-benzyl)-3-morpholin-4-yl-3-oxo-propionyl-amino]-3,3-dimethyl-butyrylamino}-5-guanidino-pentanoic acid amide trifluoroacetic acid salt | ok | solid ph. |
| 41 | 2-(S)-{2-(S)-[2-(R,S)-(4-Carbamimidoyl-benzyl)-3-morpholin-4-yl-3-oxo-propionyl-amino]-2-cyclohexyl-acetylamino}-5-guanidino-pentanoic acid amide trifluoroacetic acid salt | ok | solid ph. |
| 42 | 2-(S)-{2-(S)-[2-(R,S)-(4-Carbamimidoyl-benzyl)-3-morpholin-4-yl-3-oxo-propionyl-amino]-3-cyclohexyl-propionylamino}-5-guanidino-pentanoic acid amide trifluoroacetic acid salt | ok | solid ph. |
| 43 | 2-(S)-{2-(S)-[2-(R,S)-(4-Carbamimidoyl-benzyl)-3-morpholin-4-yl-3-oxo-propionyl-amino]-3-phenyl-propionylamino}-5-guanidino-pentanoic acid amide trisfluoroacetic acid salt | ok | solid ph. |

-continued

| No. | Name | MS | Method |
|---|---|---|---|
| 44 | 2-(R,S)-(4-Carbamimidoyl-benzyl)-N-((S)-carboxy-cyclohexyl-methyl)-malonamic acid hydrochloric acid salt | ok | class. Syn. |
| 45 | 2-(R,S)-(4-Carbamimidoyl-benzyl)-N-({1-(S)-[4-(7-chloro-naphthalene-2-sulfonyl)-piperazine-1-carbonyl]-4-guanidino-butylcarbamoyl}-(S)-cyclohexyl-methyl)-N',N'dimethyl-malonamide hydrochloric acid salt | ok | class. Syn. |
| 46 | N-{[(6-Amino-pyridin-3-ylmethyl)-carbamoyl]-(S)-cyclohexyl-methyl}-2-(R,S)-(4-carbamimidoyl-benzyl)-N',N'-dimethyl-malonamide hydrochloric acid salt | ok | class. Syn. |
| 47 | 2-(R,S)-(4-Carbamimidoyl-benzyl)-N-{(S)-cyclohexyl-[(piperidin-4-ylmethyl)-carbamoyl]-methyl}-N',N'-dimethyl-malonamide hydrochloric acid salt | ok | class. Syn. |
| 48 | 2-(R,S)-(4-Carbamimidoyl-benzyl)-N-[(4-cyano-benzylcarbamoyl)-(S)-cyclohexyl-methyl]-N',N'-dimethyl-malonamide acetic acid salt | ok | class. Syn. |
| 49 | 2-(4-Carbamimidoyl-benzyl)-N-[(4-cyano-benzylcarbamoyl)-(S)-cyclohexyl-methyl]-N',N'-dimethyl-malonamide acetic acid salt, less polar diastereomer | ok | class. Syn. |
| 50 | N-Benzyl-2-(R,S)-(4-carbamimidoyl-benzyl)-N'-(S)-(3-chloro-benzylcarbamoyl)-cyclohexyl-methyl]-malonamide trifluoroacetic acid salt | ok | class. Syn. |
| 51 | N-Benzyl-2-(R,S)-(4-carbamimidoyl-benzyl)-N'-[(S)-cyclohexyl-(2-phenylamino-ethylcarbamoyl)-methyl]-malonamide hydrochloric acid salt | ok | class. Syn. |
| 52 | N-{[(Benzo[1,3]dioxol-5-ylmethyl)-carbamoyl]-(S)-cyclohexyl-methyl}-N'-benzyl-2-(R,S)-(4-carbamimidoyl-benzyl)-malonamide hydrochloric acid salt | ok | class. Syn. |
| 53 | N-Benzyl-2-(R,S)-(4-carbamimidoyl-benzyl)-N'-[(S)-cyclohexyl-(2-phenoxy-ethyl-carbamoyl)-methyl]-malonamide hydrochloric acid salt | ok | class. Syn. |
| 54 | (2-{2-(S)-[3-(4-Carbamimidoyl-phenyl)-2-(R,S)-dimethylcarbamoyl-propionyl-amino]-2-cyclohexyl-acetylamino}-ethyl)-carbamic acid tert-butyl ester hydrochloric acid salt | ok | class. Syn. |
| 55 | (3-{2-(S)-[3-(4-Carbamimidoyl-phenyl)-2-(R,S)-dimethylcarbamoyl-propionyl-amino]-2-cyclohexyl-acetylamino}-propyl)-carbamic acid tert-butyl ester hydrochloric acid salt | ok | class. Syn. |
| 56 | N-Benzyl-2-(R,S)-(4-carbamimidoyl-benzyl)-N'-[(4-chloro-benzylcarbamoyl)-cyclohexyl-methyl]-malonamide hydrochloric acid salt | ok | class. Syn. |
| 57 | N-Benzyl-2-(R,S)-(4-carbamimidoyl-benzyl)-N'-{[2-(S)-(4-chloro-phenyl)-ethyl-carbamoyl]-cyclohexyl-methyl}-malonamide hydrochloric acid salt | ok | class. Syn |
| 58 | N-Benzyl-N'-{[2-(S)-(3,5-bis-trifluoromethyl-phenyl)-ethylcarbamoyl]-cyclohexyl-methyl}-2-(R,S)-(4-carbamimidoyl-benzyl)-malonamide hydrochloric acid salt | ok | class. Syn. |
| 59 | 2-(R,S)-(4-Carbamimidoyl-benzyl)-N-{(S)-cyclohexyl-[2-(3,4-dichloro-phenyl)-ethylcarbamoyl]-methyl}-N',N'-dimethyl-malonamide acetic acid salt | ok | class. Syn. |
| 60 | [3-({2-[3-(4-Carbamimidoyl-phenyl)-2-(R,S)-dimethylcarbamoyl-propionylamino]-2-(S)-cyclohexyl-acetylamino}-methyl)-benzyl]-carbamic acid tert-butyl ester trifluoroacetic acid salt | ok | class. Syn. |
| 61 | N-[((S)-2-Amino-ethylcarbamoyl)-cyclohexyl-methyl]-2-(R,S)-(4-carbamimidoyl-benzyl)-N',N'-dimethyl-malonamide trifluoroacetic acid salt | ok | class. Syn. |
| 62 | N-[((S)-3-Amino-propylcarbamoyl)-cyclohexyl-methyl]-2-(R,S)-(4-carbamimidoyl-benzyl)-N',N'-dimethyl-malonamide trifluoroacetic acid salt | ok | class. Syn. |
| 63 | N-[((S)-3-Aminomethyl-benzylcarbamoyl)-cyclohexyl-methyl]-2-(R,S)-(4-carbamimidoyl-benzyl)-N',N'-dimethyl-malonamide trifluoroacetic acid salt | ok | class. Syn. |
| 64 | 2-(R,S)-(4-Carbamimidoyl-benzyl)-N-[((S)-3-cyano-benzylcarbamoyl)-cyclohexyl-methyl]-N',N'-dimethyl-malonamide hydrochloric acid salt | ok | class. Syn. |
| 65 | N-[((S)-2-Acetylamino-ethylcarbamoyl)-cyclohexyl-methyl]-2-(R,S)-(4-carbamimidoyl-benzyl)-N',N'-dimethyl-malonamide trifluoroacetic acid salt | ok | class. Syn. |
| 66 | N-[((S)-3-Acetylamino-propylcarbamoyl)-cyclohexyl-methyl]-2-(R,S)-(4-carbamimidoyl-benzyl)-N',N'-dimethyl-malonamide trifluoroacetic acid salt | ok | class. Syn. |
| 67 | N-{[(S)-3-(Acetylamino-methyl)-benzylcarbamoyl]-cyclohexyl-methyl}-2-(R,S)-(4-carbamimidoyl-benzyl)-N',N'-dimethyl-malonamide trifluoroacetic acid salt | ok | class. Syn. |
| 68 | 2-(R,S)-(4-Carbamimidoyl-benzyl)-N-[((S)-3-carbamimidoyl-benzylcarbamoyl)-cyclohexyl-methyl]-N',N'-dimethyl-malonamide hydrochloric acid salt | ok | class. Syn. |
| 69 | 2-(R,S)-(4-Carbamimidoyl-benzyl)-N-[((S)-3-carbamoyl-benzylcarbamoyl)-cyclohexyl-methyl]-N',N'-dimethyl-malonamide hydrochloric acid salt | ok | class. Syn. |
| 70 | 3-({2-(S)-[3-(4-Carbamimidoyl-phenyl)-2-(R,S)-dimethylcarbamoyl-propionyl-amino]-2-cyclohexyl-acetylamino}-methyl)-benzoic acid ethyl ester hydrochloric acid salt | ok | class. Syn. |
| 71 | N-Benzyl-2-(S)-(4-carbamimidoyl-benzyl)-N'-{(S)-cyclohexyl-[2-(5-nitro-pyridin-2-ylamino)-ethylcarbamoyl]-methyl-malonamide trifluoroacetic acid salt, more polar diastereomer | ok | class. Syn. |
| 72 | N-Benzyl-2-(R,S)-(4-carbamimidoyl-benzyl)-N'-{(S)-cyclohexyl-[2-(5-nitro-pyridin-2-ylamino)-ethylcarbamoyl]-methyl}-malonamide trifluoroacetic acid salt | ok | class. Syn. |
| 73 | N-Benzyl-N'-{[2-(2-tert-butyl-phenoxy)-ethylcarbamoyl]-cyclohexyl-methyl}-2-(4-carbamimidoyl-benzyl)-malonamide hydrochloric acid salt, less polar diastereomer | ok | class. Syn. |
| 74 | N-Benzyl-2-(R,S)-(4-carbamimidoyl-benzyl)-N'-{(S)-cyclohexyl-[2-(3,4-difluoro-phenoxy)-ethylcarbamoyl]-methyl}-malonamide hydrochloric acid salt | ok | class. Syn. |
| 75 | N-Benzyl-2-(R,S)-4-carbamimidoyl-benzyl-N'-{(S)-[2-(2-chloro-3,5-difluoro-phenoxy)-ethylcarbamoyl]-cyclohexyl-methyl}-malonamide hydrochloric acid salt | ok | class. Syn. |
| 76 | N-Benzyl-2-(R,S)-(4-carbamimidoyl-benzyl)-N'-{[2-(3-chloro-05-fluoro-phenoxy)-ethylcarbamoyl]-cyclohexyl-methyl}-malonamide hydrochloirde | ok | class. Syn. |
| 77 | N-Benzyl-2-(R,S)-(4-carbamimidoyl-benzyl)-N'-{[2-(3-chloro-phenoxy)-ethyl-carbamoyl]-cyclohexyl-methyl}-malonamide hydrochloric acid salt | ok | class. Syn. |
| 78 | N-Benzyl-2-(R,S)-(4-carbamimidoyl-benzyl)-N'-{(S)-cyclohexyl-[2-(2,3-dichloro-phenoxy)-ethylcarbamoyl]-methyl}-malonamide hydrochloric acid salt | ok | class. Syn. |
| 79 | N-{[(S)-2-(4-Amino-phenyl)-ethylcarbamoyl]-cyclohexyl-methyl}-N'-benzyl-2-(R,S)-(4-carbamimidoyl-benzyl)-malonamide hydrochloric acid salt | ok | class. Syn. |
| 80 | N-{[(S)-3-(2-Amino-phenyl)-3-oxo-propylcarbamoyl]-cyclohexyl-methyl}-N'-benzyl-2-(R,S)-(4-carbamimidoyl-benzyl)-malonamide hydrochloric acid salt | ok | class. Syn. |
| 81 | N-{[(S)-2-(3-Amino-propionyl)-phenylcarbamoyl]-cyclohexyl-methyl}-N'-benzyl-2-(R,S)-(4-carbamimidoyl-benzyl)-malonamide hydrochloric acid salt | ok | class. Syn. |

-continued

| No. | Name | MS | Method |
|---|---|---|---|
| 82 | 2-(R,S)-(4-Carbamimidoyl-benzyl)-N-((S)-cyclohexyl-{3-[(naphthalene-1-sulfonyl-amino)-methyl]-benzylcarbamoyl}-methyl)-N',N'-dimethyl-malonamide trifluoroacetic acid salt | ok | class. Syn. |
| 83 | 2-(4-Carbamimidoyl-benzyl)-N-((S)-cyclohexyl-{3-[(naphthalene-2-sulfonyl-amino)-methyl]-benzylcarbamoyl}-methyl)-N',N'-dimethyl-malonamide trifluoroacetic acid salt, more polar diastereomer | ok | class. Syn. |
| 84 | 2-(4-Carbamimidoyl-benzyl)-N-((S)-cyclohexyl-}3-[(naphthalene-2-sulfonyl-amino)-methyl]-benzylcarbamoyl}-methyl)-N',N'-dimethyl-malonamide trifluoroacetic acid salt, less polar diastereomer | ok | class. Syn. |
| 85 | 2-(4-Carbamimidoyl-benzyl)-N-((S)-cyclohexyl-{3-[(3,5-dichloro-benzene-sulfonylamino)-methyl]-benzylcarbamoyl}-methyl)-N',N'-dimethyl-malonamide trifluoroacetic acid salt, more polar diastereomer | ok | class. Syn. |
| 86 | 2-(4-Carbamimidoyl-benzyl)-N-((S)-cyclohexyl-{3-[(3,5-dichloro-benzene-sulfonylamino)-methyl]-benzylcarbamoyl}-methyl)-N',N'-dimethyl-malonamide trifluoroacetic acid salt, less polar diastereomer | ok | class. Syn. |
| 87 | 2-(R,S)-(4-Carbamimidoyl-benzyl)-N-{(S)-[2-(4-carbamimidoyl-phenyl)-1-carbamoyl-ethylcarbamoyl]-cyclohexyl-methyl}N',N'-dimethyl-malonamide acetic acid salt | ok | class. Syn. |
| 88 | 2-(R,S)-(4-Carbamimidoyl-benzyl)-N-[(S)-cyclohexyl-(4-guanidino-butyl-carbamoyl)-methyl]-N',N'-dimethyl-malonamide sulfuric acid salt | ok | class. Syn. |
| 89 | 2-(R,S)-(4-Carbamimidoyl-benzyl)-N-[(S)-(4-carbamoyl-benzylcarbamoyl)-cyclo-hexyl-methyl]-N',N'-dimethyl-malonamide hydrochloric acid salt | ok | class. Syn. |
| 90 | N-[(S)-(4-Amino-benzylcarbamoyl)-cyclohexyl-methyl]-2-(4-carb-amimidoyl-benzyl)-N',N'-dimethyl-malonamide hydrochloric acid salt, more polar diastereomer | ok | class. Syn. |
| 91 | N-[(S)-(4-Amino-benzylcarbamoyl)-cyclohexyl-methyl]-2-(4-carbamimidoyl-benzyl)-N',N'-dimethyl-malonamide hydrochloric acid salt, less polar diastereomer | ok | class. Syn. |
| 92 | 2-(4-Carbamimidoyl-benzyl)-N-[(S)-cyclohexyl-(4-sulfamoyl-benzyl-carbamoyl)-methyl]-N',N'-dimethyl-malonamide hydrochloric acid salt, more polar diastereomer | ok | class. Syn. |
| 93 | 2-(4-Carbamimidoyl-benzyl)-N-[(S)-cyclohexyl-(4-sulfamoyl-benzyl-carbamoyl)-methyl]-N',N'-dimethyl-malonamide hydrochloric acid salt, less polar diastereomer | ok | class. Syn. |
| 94 | 2-(R,S)-(4-Carbamimidoyl-benzyl)-N-{(S)-cyclohexyl-[3-(methanesulfonylamino-methyl)-benzylcarbamoyl]-methyl}-N',N'-dimethyl-malonamide trifluoroacetic acid salt | ok | class. Syn. |
| 95 | N-{(S)-Cyclohexyl-[4-(N-hydroxycarbamimidoyl)-benzylcarbamoyl]-methyl}-2-(R,S)-[4-(N-hydroxy-carbamimidoyl)-benzyl]-N',N'-dimethyl-malonamide | ok | class. Syn. |
| 96 | 2-(R,S)-(4-Carbamimidoyl-benzyl)-N-{(S)-cyclohexyl-[1-(4-guanidino-phenyl)-2-oxo-2-pyrrolidin-1-yl-ethylcarbamoyl]-methyl}-N',N'-dimethyl-malonamide hydrochloric acid salt | ok | class. Syn. |
| 97 | 2-(4-Carbamimidoyl-benzyl)-N-[(S)-cyclohexyl-(4-guanidino-benzyl-carbamoyl)-methyl]-N',N'-dimethyl-malonamide trifluoroacetic acid salt, more polar diastereomer | ok | class. Syn. |
| 98 | 2-(4-Carbamimidoyl-benzyl)-N-[(S)-cyclohexyl-(4-guanidino-benzyl-carbamoyl)-methyl]-N',N'-dimethyl-malonamide trifluoroacetic acid salt, less polar diastereomer | ok | class. Syn. |
| 99 | N-Benzyl-2-(4-carbamimidoyl-benzyl)-N'-{(S)-cyclohexyl-[4-guanidino-1-(4-phenyl-piperazine-1-carbonyl)-butylcarbamoyl]-methyl}-N-methyl-malonamide trifluoroacetic acid salt, less polar diastereomer | ok | class. Syn. |
| 100 | N-Benzyl-2-(4-carbamimidoyl-benzyl)-N'-{(S)-cyclohexyl-[4-guanidino-1-(4-phenyl-piperazine-1-carbonyl)-butylcarbamoyl]-methyl}-N-methyl-malonamide trifluoroacetic acid salt, more polar diastereomer | ok | class. Syn. |
| 101 | N-Benzyl-2-(4-carbamimidoyl-benzyl)-N'-[(S)-(4-carbamimidoyl-benzyl-carbamoyl)-cyclohexyl-methyl]-malonamide trifluoroacetic acid salt, less polar diastereomer | ok | class. Syn. |
| 102 | N-Benzyl-2-(4-carbamimidoyl-benzyl)-N'-[(S)-(4-carbamimidoyl-benzyl-carbamoyl)-cyclohexyl-methyl]-malonamide trifluoroacetic acid salt, more polar diastereomer | ok | class. Syn. |
| 103 | N-[(S)-(4-Aminomethyl-benzylcarbamoyl)-cyclohexyl-methyl]-2-(4-carbamoyl-benzyl)-N',N'-dimethyl-malonamide trifluoroacetic acid salt, less polar diastereomer | ok | class. Syn. |
| 104 | N-[(S)-(4-Aminomethyl-benzylcarbamoyl)-cyclohexyl-methyl]-2-(4-carbamoyl-benzyl)-N',N'-dimethyl-malonamide trifluoroacetic acid salt, more polar diastereomer | ok | class. Syn. |
| 105 | N-[(S)-(4-Aminomethyl-benzylcarbamoyl)-cyclohexyl-methyl]-2-(4-carbamimidoyl-benzyl)-N',N'-dimethyl-malonamide trifluoroacetic acid salt, less polar diastereomer | ok | class. Syn. |
| 106 | N-[(S)-(4-Aminomethyl-benzylcarbamoyl)-cyclohexyl-methyl]-2-(4-carbamimidoyl-benzyl)-N',N'-dimethyl-malonamide trifluoroacetic acid salt, more polar diastereomer | ok | class. Syn. |
| 107 | 2-{2-(S)-[2-(Benzyl-methyl-carbamoyl)-3-(4-carbamimidoyl-phenyl)-propionylamino]-2-cyclohexyl-acetylamino}-3-naphthalen-1-yl-propionic acid ethyl ester trifluoroacetic acid salt, more polar diastereomeric mixture | ok | class. Syn. |
| 108 | 2-{2-(S)-[2-(Benzyl-methyl-carbamoyl)-3-(4-carbamimidoyl-phenyl)-propionylamino]-2-cyclohexyl-acetylamino}-3-naphthalen-1-yl-propionic acid ethyl ester trifluoroacetic acid salt, less polar diastereomeric mixture | ok | class. Syn. |
| 109 | N-Benzyl-2-(4-carbamimidoyl-benzyl)-N'-((S)-cyclohexyl-{2-[4-(1-imino-ethyl)-piperazin-1-yl]-ethylcarbamoyl}-methyl)-malonamide trifluoroacetic acid salt, more polar diastereomer | ok | class. Syn. |
| 110 | N-Benzyl-2-(4-carbamimidoyl-benzyl)-N'-((S)-cyclohexyl-{2-[4-(1-imino-ethyl)-piperazin-1-yl]-ethylcarbamoyl}-methyl)-malonamide trifluoroacetic acid salt, less polar diastereomer | ok | class. Syn. |
| 111 | N-Benzyl-2-(R)-(4-carbamimidoyl-benzyl)-N'-{(S)-[(1-carbamimidoyl-piperidin-4-ylmethyl)-carbamoyl]-cyclohexyl-methyl}-N-methyl-malonamide trifluoroacetic acid salt, more polar diastereomer | ok | class. Syn. |
| 112 | N-Benzyl-2-(S)-(4-carbamimidoyl-benzyl)-N'-{(S)-[(1-carbamimidoyl-piperidin-4-ylmethyl)-carbamoyl]-cyclohexyl-methyl}-N-methyl-malonamide trifluoroacetic acid salt, less polar diastereomer | ok | Class. Syn. |
| 113 | 2-(S)-(4-Carbamimidoyl-benzyl)-N-{(S)-[(1-carbamimidoyl-piperidin-4-ylmethyl)-carbamoyl]-cyclohexyl-methyl}-N',N'-dimethyl-malonamide hydrochloric acid salt, less polar diastereomer | ok | Class. Syn. |
| 114 | 2-(R)-(4-Carbamimidoyl-benzyl)-N-{(S)-[(1-carbamimidoyl-piperidin-4-ylmethyl)-carbamoyl]-cyclohexyl-methyl}-N',N'-dimethyl-malonamide hydrochloric acid salt, more polar diastereomer | ok | Class. Syn. |
| 115 | 2-(R,S)-(4-Carbamimicloyl-benzyl)-N-{(S)-[(4-cyano-cyclohex-ylmethyl)-carbamoyl]- | ok | Class. Syn. |

-continued

| No. | Name | MS | Method |
|---|---|---|---|
| | cyclohexyl-methyl}-N',N'-dimethyl-malonamide hydrochloric acid salt | | |
| 116 | 2-(4-Carbamimidoyl-benzyl)-N-{(S)-[(4-carbamimidoyl-cyclohexylmethyl)-carbamoyl]-cyclohexyl-methyl}-N',N'-dimethyl-malonamide | ok | class. Syn. |
| 117 | N-{(S)-[(4-Aminomethyl-cyclohexylmethyl)-carbamoyl]-cyclohexyl-methyl}-2-(4-carbamimidoyl-benzyl)-N',N'-dimethyl-malonamide | ok | class. Syn. |
| 118 | 2-(4-Carbamimidoyl-benzyl)-N-[(S)-(5-carbamimidoyl-pentylcarbamoyl)-cyclohexyl-methyl]-N',N'-dimethyl-malonamide, less polar diastereomer | ok | class. Syn. |
| 119 | 2-(4-Carbamimidoyl-benzyl)-N-[(S)-(5-carbamimidoyl-pentylcarbamoyl)-cyclohexyl-methyl]-N',N'-dimethyl-malonamide, more polar diastereomer | ok | class. Syn. |
| 120 | N-(S)-(Cyclohexyl-{[4-(N,N-dimethyl-carbamimidoyl)-cyclohexylmethyl]-carbamoyl}-methyl)-2-[4-(N,N-dimethyl-carbamimidoyl)-benzyl]-N',N'-dimethyl-malonamide | ok | class. Syn. |

Example 121 and 122

N-Benzyl-2-(4-carbamimidoyl-benzyl)-N'-{(S)-[(4-carbamimidoyl-cyclohexylmethyl)-carbamoyl]-cyclohexyl-methyl}-N-methyl-malonamide, Less Polar Diastereomer and N-Benzyl-2-(4-carbamimidoyl-benzyl)-N'-{(S)-[(4-carbamimidoyl-cyclohexylmethyl)-carbamoyl]-cyclohexyl-methyl}-N-methyl-malonamide, More Polar Diastereomer a) N-Benzyl-2-(4-cyano-benzyl)-N-methyl-malonamic Acid N-Benzyl-2-(4-cyano-benzyl)-N-methyl-malonamic acid was synthesized by using the procedure described in Example 3a) by using methylbenzylamine instead of benzylamine (yield: 81%). mp.: 144–145° C. (dc), MS m/z: 323 (M+H)+.

b) [2-(R,S)-(Benzyl-methyl-carbamoyl)-3-(4-cyano-phenyl)-propionylamino]-(S)-cyclohexyl-acetic Acid Methyl Ester

[2-(R,S)-(Benzyl-methyl-carbamoyl)-3-(4-cyano-phenyl)-propionylamino]-(S)-cyclohexyl-acetic acid methyl ester was synthesized by using the procedure described in example 3b) by using N-benzyl-2-(4-cyano-benzyl)-N-methyl-malonamic acid instead of N-benzyl-2-(4-cyano-benzyl)-malonamic acid (yield: 71%).

c) [2-(R,S)-(Benzyl-methyl-carbamoyl)-3-(4-cyano-phenyl)-propionylamino]-(S)-cyclohexyl-acetic Acid 1.5 g (3.15 mmol) of the above [2-(R,S)-(Benzyl-methyl-carbamoyl)-3-(4-cyano-phenyl)-propionylamino]-(S)-cyclohexyl-acetic acid methyl ester was suspended in water/concentrated hydrochloric acid (1/1, 40 ml) and acetonitrile (40 ml) was added to give a solution. The reaction mixture was stirred at room temperature for 10 days. The reaction mixture was concentrated in vacuo and the residue lyophilized to give the desired product in 63% yield.

d) N-Benzyl-2-(R,S)-(4-cyano-benzyl)-N'-{[(4-cyano-cyclohexylmethyl)-carbamoyl]-(S)-cyclohexyl-methyl}-N-methyl-malonamide To [2-(R,S)-(Benzyl-methyl-carbamoyl)-3-(4-cyano-phenyl)-propionylamino]-(S)-cyclohexyl-acetic acid (910 mg, 1.97 mmol) in dimethylformamide (150 ml) were added HATU (825 mg, 2.17 mmol) and collidine (263 mg, 2.17 mmol) at 0° C. After 30 minutes at 0° C. 4-aminomethyl-cyclohexanecarbonitrile (272 mg, 1.97 mmol) was added. The mixture was stirred for 1 hour, then allowed to warm to room temperature, and stand at room temperature for 72 hours. After evaporation the residue was stirred with Na₂CO₃ solution and the precipitate was sucked off to yield 1.18 g of the desired product which was used for further reactions without purification.

e) N-Benzyl-2-(4-carbamimidoyl-benzyl)-N'-{(S)-[(4-carbamimidoyl-cyclohexylmethyl)-carbamoyl]-cyclohexyl-methyl}-N-methyl-malonamide, Less Polar Diastereomer and N-Benzyl-2-(4-carbamimidoyl-benzyl)-N'-{(S)-[(4-carbamimidoyl-cyclohexylmethyl)-carbamoyl]-cyclohexyl-methyl}-N-methyl-malonamide, More Polar Diastereomer The title compounds were synthesized by using the procedure described in example 4b) by using in the second step dimethylformamide instead of 2-propanol. The separation of the diastereomers was done by preparative HPLC (Nucleosil $C_{18}$ 250/21, 7 µM, acetonitrile/water+0.1% TFA). MS m/z: 616.4 (M+H)+, 308.9 (M+2H)²+. Both diastereomers showed the same MS.

Example 123 and 124

N-Benzyl-2-(4-carbamimidoyl-benzyl)-N'-(S)-(cyclohexyl-{[1-(1-imino-ethyl)-piperidin-4-ylmethyl]-carbamoyl}-methyl)-N-methyl-malonamide, More Polar Diastereomer and N-Benzyl-2-(4-carbamimidoyl-benzyl)-N'-(S)-(cyclohexyl-{[1-(1-imino-ethyl)-piperidin-4-ylmethyl]-carbamoyl}-methyl)-N-methyl-malonamide, Less Polar Diastereomer a) [2-(R,S)-(Benzyl-methyl-carbamoyl)-3-(4-carbamimidoyl-phenyl)-propionylamino]-(S)-cyclohexyl-acetic Acid Methyl Ester

[2-(R,S)-(Benzyl-methyl-carbamoyl)-3-(4-cyano-phenyl)-propionylamino]-(S)-cyclohexyl-acetic acid methyl ester (described in example 121/122 b)) was used to synthesize the title compound analogously to the procedure described in example 4 b) by using in the second step dimethylformamide instead of 2-propanol.

b) [2-(R,S)-(Benzyl-methyl-carbamoyl)-3-(4-carbamimidoyl-phenyl)-propionylamino]-(S)-cyclohexyl-acetic Acid Trifluoroacetic Acid Salt 22.1 g (44.8 mmol) of the above [2-(R,S)-(Benzyl-methyl-carbamoyl)-3-(4-carbamimidoyl-phenyl)-propionylamino]-(S)-cyclohexyl-acetic acid methyl ester was suspended in water/concentrated hydrochloric acid (1/1, 40 ml) and acetonitrile (40 ml) was added to give a solution. The reaction mixture was stirred at room temperature for 7 days. The reaction mixture was concentrated in vacuo and the residue was purified on silica gel with dichloromethane/methanol/TFA as solvent to give the desired product.

c) N-Benzyl-2-(R,S)-(4-carbamimidoyl-benzyl)-N'-{(S)-cyclohexyl-[(piperidin-4-ylmethyl)-carbamoyl]-methyl}-N-methyl-malonamide trifluoroacetic Acid Salt, More Polar Diastereomer and N-Benzyl-2-(R,S)-(4-carbamimidoyl-benzyl)-N'-{(S)-cyclohexyl-[(piperidin-4-ylmethyl)-carbamoyl]-methyl}N-methyl-malonamide Trifluoroacetic Acid Salt, Less Polar Diastereomer To [2-(R,S)-(Benzyl-methyl-carbamoyl)-3-(4-carbamimidoyl-phenyl)-propionylamino]-(S)-cyclohexyl-acetic acid trifluoroacetic acid salt (1.5 g, 2.53 mmol) in dimethylformamide (100 ml) were added HATU (963 mg, 2.53 mmol) and N-ethyl-diisopropylamine (1.31 g, 10.10 mmol) at 0° C. After 30 minutes at 0° C. 4-aminomethyl-piperidine-1-carboxylic acid tert-butyl ester (542 mg, 2.53 mmol) was added. The mixture was then allowed to warm to room temperature, and stand at room temperature for 16 hours. After evaporation the residue was stirred with Na$_2$CO$_3$ solution and the precipitate was sucked off to yield 1.68 g of the BOC-protected desired product. The residue was solved in trifluoroacetic acid/water (95/5, 10 ml) and stirreed at room temperature for 90 minutes. The reaction mixture was evaporated in vacou and purified by preparative HPLC (HPLC-conditions: lichrospher, 250/25, 5 μM, acetonitrile/water+0.1% TFA) to yield 102 mg of the more polar and 117 mg of the less polar diastereomer. MS of both diastereomers showed the correct molecular weight.

d) N-Benzyl-2-(4-carbamimidoyl-benzyl)-N'-(S)-(cyclohexyl-{[1-(1-imino-ethyl)-piperidin-4-ylmethyl]-carbamoyl}-methyl)-N-methyl-malonamide Trifluoroacetic Acid Salt, More Polar Diastereomer and N-Benzyl-2-(4-carbamimidoyl-benzyl)-N'-(S)-(cyclohexyl-{[1-(1-imino-ethyl)-piperidin-4-ylmethyl]-carbamoyl}-methyl)-N-methyl-malonamide Trifluoroacetic Acid Salt, Less Polar Diastereomer N-Benzyl-2-(R,S)-(4-carbamimidoyl-benzyl)-N'-{(S)-cyclohexyl-[(piperidin-4-ylmethyl)-carbamoyl]-methyl}-N-methyl-malonamide trifluoroacetic acid salt (50 mg, 0.06 mmol, less polar diastereomer) was solved in methanol (10 ml) and triethylamine (73 mg, 0.72 mmol) and ethylacetimidate hydrochloride (23 mg, 0.18 mmol) in methanol (10 ml) were added. During the following 6 days the addition of triethylamine and ethylacetimidate was repeated three times. The reaction mixture was evaporated and purified by prep. HPLC (HPLC-conditions: lichrospher, 250/25, 5 μM, acetonitrile/water+0.1% TFA) to yield the more polar diastereomer in 28% and the less polar diastereomer in 21%. MS of both diastereomers showed the correct molecular weight.

Example 125 and 126

N-Benzyl-2-(4-carbamimidoyl-benzyl)-N'-(S)-(cyclohexyl-{[1-(1-imino-propyl)-piperidin-4-ylmethyl]-carbamoyl}-methyl)-N-methyl-malonamide, more polar diastereomer and N-Benzyl-2-(4-carbamimidoyl-benzyl)-N'-(S)-(cyclohexyl-{[1-(1-imino-propyl)-piperidin-4-ylmethyl]-carbamoyl}-methyl)-N-methyl-malonamide, Less Polar DiastereQmer The title compounds were synthesized as described in example 123/124 d) by using propionimidic acid ethyl ester instead of ethyl acetimidate.

Abbreviations used in the text:

| | |
|---|---|
| Å | Ångström |
| aPTT | activated partial thromboplastin time |
| ATS | Antistasin |
| AV | Arteriovenous |
| Boc | tert butoxycarbonyl |
| ° C. | degrees Celsius |
| CDCl$_3$ | deutero chloroform |
| Class. syn. | classical synthesis |
| cm | Centimeter |
| dc | Decomposition |
| DCCI | Dicyclohexylcarbodiimide |
| DCRu | Dichlorotetrakis(triphenylphosphine)ruthenium(II) |
| diast. | Diastereomeric |
| DIC | disseminated intravascular coagulation |
| DICI | Diisopropylcarbodiimide |
| DMSO | Dimethylsulfoxide |
| DVT | deep vein thrombosis |
| FAB | fast atom bombardment |
| Fmoc | 9-fluorenylmethoxycarbonyl |
| FT-IR | fourier transformed infrared |

-continued

| | |
|---|---|
| g | Gram |
| h | Hour |
| HATU | N-[(Dimethylamino)-1H-1,2,3-triazolo[4,5-b]pyridin-1yl-methylene]-N-methylmethanaminium hexafluorophosphate N-oxide |
| HOBt | 1-Hydroxybenzotriazole |
| HPLC | high pressure liquid chromatography |
| HPLC/ESMS | high pressure liquid chromatography/electrospray mass spectra |
| id | Intraduodenal |
| iv | Intravenous |
| kg | Kilogram |
| l | Liter |
| LMWH | low molecular weight haparin |
| mg | Milligram |
| MHz | Megahertz |
| min | Minutes |
| ml | Milliliter |
| mM | Millimolar |
| mmol | Millimol |
| MPLC | medium pressure liquid chromatography |
| MS | mass spetra |
| mp. | melting point |
| μl | Microliter |
| μm | Micrometer |
| μM | Micromolar |
| nm | Nanometer |
| nM | Nanomolar |
| NMR | nuclear magnetic resonance |
| PE | Polyethylene |
| PEG | Polyethyleneglycole |
| PG | protecting group |
| Pmc | 2,2,5,7,8-pentamethylchroman-6-sulfonyl- |
| PPP | platelet poor blood |
| psi | pounds per square inch |
| PT | prothrombin time |
| sec | Seconds |
| Solid ph. | solid phase synthesis |
| Subl. | Sublimation |
| TAP | tick anticoagulant peptide |
| TBS-BSA | tris buffered saline bovine serum albumin |
| TBS-PEG | tris buffered saline polyethylene glycole |
| TF | tissue factor |
| TFPI | tissue factor pathway inhibitor |
| TLC | thin layer chromatography |
| TOTU | O-((Cyano-(ethoxycarbonyl)-methylen)amino)-N,N,N',N'-tetra-methyluronium tetrafluoroborate |
| TPCK | Tosyl phenyl chloromethyl ketone |
| UV | ultra violet |

We claim:
1. A compound of the formula I,

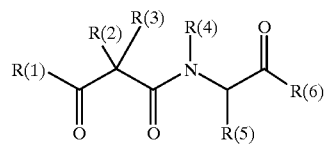

(I)

in any stereoisomeric form,
its physiologically acceptable salt, or mixtures thereof, wherein R(1) is NR(7)R(8), OR(9), or NR(7a)R(8a);

R(2) is hydrogen or (C$_1$–C$_4$)-alkyl;

R(3) is (C$_6$–C$_{10}$)-aryl-(C$_1$–C$_4$)-alkyl which is substituted in the aryl or alkyl moiety by a residue R(11), heteroaryl-(C$_1$–C$_4$)-alkyl, (C$_3$–C$_7$)-cycloalkyl-(C$_1$–C$_4$)-alkyl, where heteroaryl, cycloalkyl, or alkyl are unsubstituted or substituted by one, two, or three residues R(11), or heteroalkyl-(C$_1$–C$_4$)-alkyl, which is unsubstituted or substituted by a residue R(23);

R(4) is hydrogen, (C₁–C₄)-alkyl, (C₃–C₇)-cycloalkyl, (C₃–C₇)-cycloalkyl-(C₁–C₄)-alkyl, or (C₆–C₁₀)-aryl-(C₁–C₄)-alkyl;

R(5) is hydrogen, (C₁–C₁₀)-alkyl, (C₃–C₇)-cycloalkyl, (C₃–C₇)-cycloalkyl-(C₁–C₄)-alkyl, (C₆–C₁₀)-aryl, (C₆–C₁₀)-aryl-(C₁–C₄)-alkyl, or a residue of the α-C-atom of a natural amino acid, wherein alkyl, cycloalkyl and aryl are unsubstituted or substituted by a residue which is hydroxy, benzyloxy, carboxy, or N(R(13))₂; or R(4) and R(5) together form a residue of the formula II or III

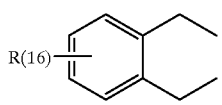
(II)

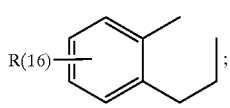
(III)

R(6) is OR(9), N(R(13))₂, R(6a), NR(34)R(13), or

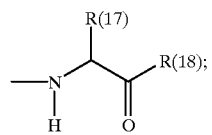

R(6a) is

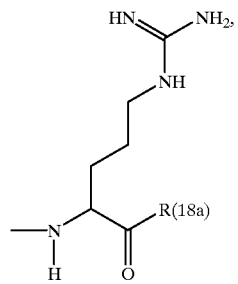

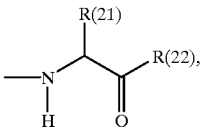

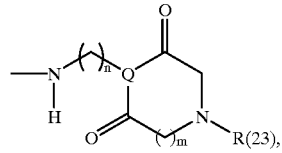

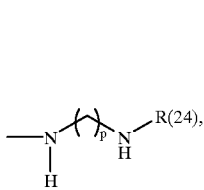

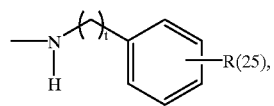

-continued

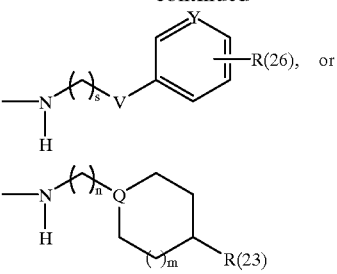

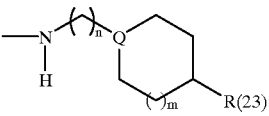

R(7) is hydrogen, (C₁–C₆)-alkyl or R(8);

R(8) is (C₁–C₆)-alkyl, (C₆–C₁₀)-aryl, or (C₆–C₁₀)-aryl-(C₁–C₄)-alkyl, where alkyl, aryl and aryl in arylalkyl are substituted by one, two or three identical or different residues R(10); or R(7) and R(8) together with the nitrogen atom to which they are bound form a 5- or 6-membered, saturated or unsaturated, heterocyclic ring which does not or does contain an additional nitrogen-, sulfur-, or oxygen-atom atom, and which is unsubstituted or substituted by a residue R(11);

R(7a) and R(8a) are, independently of one another hydrogen, (C₁–C₆)-alkyl, (C₆–C₁₀)-aryl, or (C₆–C₁₀)-aryl-(C₁–C₄)-alkyl;

R(9) is hydrogen, (C₁–C₆)-alkyl, (C₆–C₁₀)-aryl, (C₆–C₁₀)-aryl-(C₁–C₄)-alkyl, heteroaryl, or heteroaryl-(C₁–C₄)-alkyl;

R(10) is (C₁–C₄)-alkoxy, hydroxycarbonyl, (C₁–C₄)-alkoxycarbonyl, chloro, bromo, fluoro, or (C₁–C₄)-alkyl, in which 1 to all hydrogen atoms are replaced by fluorine; or R(11) is R(12) or (C₁–C₄)-alkyl, which is unsubstituted or substituted by a residue R(12), heteroaryl, which is unsubstituted or substituted by N(R(9))₂ or (C₁–C₄)-alkyl;

R(12) is N(R(13))₂, COOR(9), CON(R(13))₂, cyano, NR(15)—C(=NR(14))—NHR(15), C(=NR(14))—R(35), —S(O)(NR(13))—N(R(13))₂ or C(=NR(14))—NHR(15);

R(13) is R(15) or (C₆–C₁₀)-aryl-(C₁–C₄)-alkyl;

R(14) is R(15), cyano, nitro, amino, hydroxy, (C₁–C₆)-alkoxy, or (C₆–C₁₄)-aryl-(C₁–C₆)-alkoxy, which is unsubstituted or substituted in the aryl moiety;

R(15) is hydrogen, (C₁–C₆)-alkyl, (C₁–C₆)-alkylcarbonyl, (C₁–C₆)-alkoxycarbonyl, (C₁–C₁₈)-alkylcarbonyloxy-(C₁–C₆)-alkoxycarbonyl, unsubstituted or substituted (C₆–C₁₄)-aryl-carbonyl, unsubstituted or substituted (C₆–C₁₄)-aryloxycarbonyl or (C₆–C₁₄)-aryl-(C₁–C₆)-alkoxycarbonyl which is unsubstituted or substituted in the aryl moiety;

R(16) is hydrogen, (C₁–C₄)-alkyl, (C₁–C₄)-alkoxy, fluoro, chloro, bromo, N(R(13))₂, nitro, hydroxy, or cyano;

R(17) is (C₁–C₈)-alkyl, which is substituted by a residue R(12), or heteroaryl-(C₁–C₄)-alkyl, where nitrogen, if present in the heteroaryl moiety, is unsubstituted or substituted by (C₁–C₄)-alkyl to give the N-alkyl heteroaryl moiety which has X⁻ as the counterion;

R(18) is OR(9) or NR(19)R(20);

R(18a) is NR(19a)R(20a);

R(19) and R(20) independently of one another are hydrogen, (C₁–C₁₂)-alkyl, (C₃–C₇)-cycloalkyl, ($C_3$–$C_7$)-cycloalkyl-($C_1$–$C_4$)-alkyl, where alkyl is unsubstituted or substituted by an aminocarbonyl residue, ($C_6$–$C_{10}$)-aryl, ($C_6$–$C_{10}$)-aryl-($C_1$–$C_4$)-alkyl, or heteroaryl-($C_1$–$C_4$)-alkyl; or R(19) and R(20) together with the nitrogen atom to which they are bound form a 5- or 6-membered, saturated or unsaturated, heterocyclic ring, which does not contain or does contain an additional nitrogen-, sulfur- or oxygen atom and which is unsubstituted or substituted by a substituent which is phenyl or naphthyl-sulfonyl which is substituted in the naphtyl-part with chloro;

R(19a) is hydrogen or R(20a);

R(20a) is ($C_1$–$C_4$)-alkyl, which is substituted by a residue R(27); ($C_3$–$C_7$)-cycloalkyl, ($C_3$–$C_{10}$)-cycloalkyl-($C_1$–$C_4$)-alkyl, heteroalkyl, heteroalkyl-($C_1$–$C_4$)-alkyl, ($C_6$–$C_{10}$)-aryl or ($C_6$–$C_{10}$)-aryl-($C_1$–$C_4$)-alkyl, where aryl is substituted by 1, 2, or 3 identical or different residues R(28); or R(19a) and R(20a) together with the nitrogen atom to which they are bound form a 5- or 6-membered heterocyclic ring, which does not contain or does contain an additional nitrogen-, sulfur-, or oxygen atom and which is unsubstituted or substituted by a substituent which is phenyl or $SO_2R(31)$;

R(21) is ($C_6$–$C_{10}$)-aryl, ($C_6$–$C_{10}$)-aryl-($C_1$–$C_4$)-alkyl, heteroaryl, or heteroaryl-($C_1$–$C_4$)-alkyl, where aryl and heteroaryl are unsubstituted or substituted independently of one another by a residue R(12) or by 1, 2, 3, 4 or 5 identical or different residues R(16), the substitution by these residues at a nitrogen atom of the heteroaryl residue leading to a positively charged nitrogen atom having $X^-$ as the counterion;

R(22) is OR(9), N(R(13))$_2$, or a 5- or 6 membered nitrogen containing heterocyclic ring which is bound at the nitrogen;

R(23) is hydrogen, heteroaryl, which is unsubstituted or substituted by a residue N(R(13))$_2$; —NH—S(O)(NR(13))—($C_1$–$C_4$)-alkyl, —S(O)(=NR(13))—N(R(13))$_2$, R(12), or R(14);

R(24) is amidino, acetimido, R(29), ($C_6$–$C_{10}$)-aryl, or 2-pyridyl, which is unsubstituted or substituted by a residue R(30);

R(25) is ($C_1$–$C_4$)-alkyl, which is unsubstituted or substituted with one, two, or three residues R(32); ($C_1$–$C_4$)-alkoxycarbonyl, cyano, chloro, CO—N(R(13))$_2$, hydroxycarbonyl, ($C_1$–$C_6$)-alkoxycarbonyl, N(R(13))$_2$, S(O)$_r$—($C_1$–$C_4$)-alkyl, S(O)$_r$—N(R(13))$_2$, OR(9), or R(12), or two residues R(25) form a —O—$CH_2$—O—O-bridge;

R(26) is hydrogen, ($C_1$–$C_6$)-alkyl, ($C_3$–$C_7$)-cycloalkyl, ($C_3$–$C_7$)-cycloalkyl-($C_1$–$C_4$)-alkyl, ($C_1$–$C_6$)-alkoxy, ($C_1$–$C_6$)-alkylthio, fluoro, chloro, bromo, nitro, N(R(13))$_2$, ($C_1$–$C_4$)-alkylcarbonyl which is unsubstituted or substituted in the alkyl part by a residue N(R(13))$_2$ or two residues R(26) form a —$(CH_2)_q$-bridge, where q is 3 or 4;

R(27) is ($C_1$–$C_4$)-alkoxy or phenoxy;

R(28) is ($C_1$–$C_4$)-alkyl, ($C_1$–$C_4$)-alkyl, in which 1 to all hydrogen atoms are replaced by fluorine or chlorine, ($C_1$–$C_4$)-alkoxy, hydroxy, $SO_2N(R(13))_2$, N(R(13))$_2$, nitro, fluoro, chloro, bromo, or cyano; or R(29) is hydrogen, ($C_1$–$C_4$)-alkoxycarbonyl, ($C_6$–$C_{10}$)-aryl-($C_1$–$C_4$)-alkylcarbonyl, ($C_1$–$C_4$)-alkylcarbonyl, or $SO_2R(31)$;

R(30) is nitro or N(R(13))$_2$;

R(31) is ($C_1$–$C_4$)-alkyl, or ($C_6$–$C_{10}$)-aryl, which is unsubstituted or substituted by 1, 2, or 3 identical or different substituents which are fluoro, chloro, bromo, or ($C_1$–$C_4$)-alkoxy;

R(32) is fluoro or NHR(29);

R(34) is ($C_1$–$C_8$)-alkyl, which is substituted by a residue R(12);

R(35) is hydrogen, ($C_6$–$C_{10}$)-aryl, heteroaryl, N(R(13))$_2$, or ($C_1$–$C_6$)-alkyl, which is unsubstituted or substituted by a residue N(R(13))$_2$ or cyano;

n is 0, 1, 2 or 3;

m is 0 or 1;

p is 2, 3, 4, or 5;

Q is N or CH;

r is 0, 1, or 2;

s is 0, 1, 2, 3, or 4; with the proviso that s is 2, 3, or 4 if V is oxygen or sulfur;

t is 0, 1, 2, 3, or 4;

V is oxygen, carbonyl, sulfur or a single bond;

$X^-$ is a physiologically acceptable anion; and

Y is CH or N;

with the exception of the compounds 2-[2-ethoxycarbonyl-3-(4-isopropyl-phenyl)-propionylamino]-4-methyl-pentanoic acid tert-butyl ester and 2-[2-carboxy-3-(4-isopropyl-phenyl)-propionylamino]-4-methyl-pentanoic acid tert-butyl ester, and with the proviso that R(6) is R(6a) if R(1) is NR(7a)R(8a).

2. A compound or mixture as claimed in claim 1, wherein

R(1) is NR(7)R(8), OR(9), or NR(7a)R(8a);

R(2) is hydrogen or ($C_1$–$C_4$)-alkyl;

R(3) is ($C_6$–$C_{10}$)-aryl-($C_1$–$C_4$)-alkyl, which is substituted in the aryl part by a residue R(11), heteroaryl-($C_1$–$C_4$)-alkyl, ($C_3$–$C_7$)-cycloalkyl-($C_1$–$C_4$)-alkyl, where heteroaryl, cycloalkyl, or alkyl are unsubstituted or substituted by one, two, or three residues R(11), or heteroalkyl-($C_1$–$C_4$)-alkyl, which is unsubstituted or substituted by a residue R(23);

R(4) is hydrogen or ($C_1$–$C_4$)-alkyl;

R(5) is ($C_1$–$C_{10}$)-alkyl, ($C_3$–$C_7$)-cycloalkyl, phenyl, ($C_3$–$C_7$)-cycloalkyl-($C_1$–$C_4$)-alkyl, or ($C_6$–$C_{10}$)-aryl-($C_1$–$C_4$)-alkyl; wherein alkyl and aryl are unsubstituted or substituted by a residue which is hydroxy, benzyloxy, carboxy, N(R(13))$_2$; or a residue of the —C-atom of a natural amino acid; or R(4) and R(5) together form a residue of the formula II

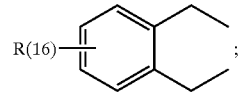

(II)

R(6) is OR(9), R(6a), NR(34)R(13), or

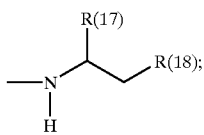

R(6a) is

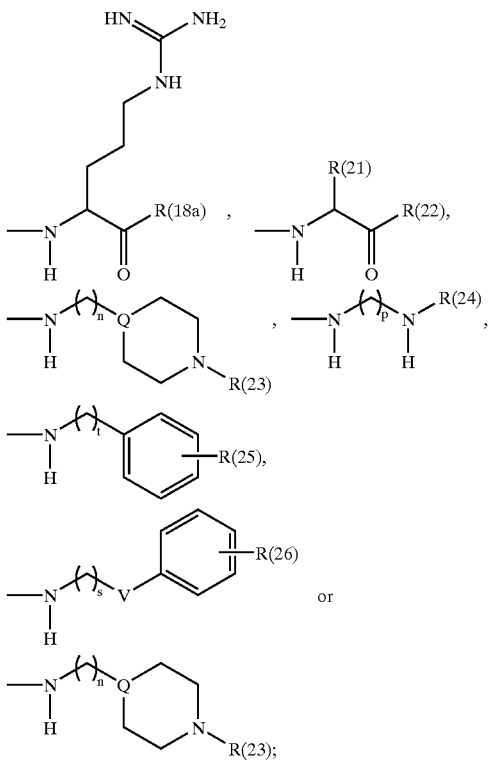

R(7) is $(C_1-C_4)$-alkyl or R(8);
R(8) is $(C_1-C_6)$-alkyl, where alkyl is substituted by 1, 2, or 3 identical or different residues R(10); or
R(7) and R(8) together with the nitrogen atom to which they are bound form a 5- or 6-membered, saturated or unsaturated, heterocyclic ring which does not or does contain an additional oxygen atom, and which is unsubstituted or substituted by a residue R(11);
R(7a) and R(8a) are, independently of one another, hydrogen, $(C_1-C_4)$-alkyl, or $(C_6-C_{10})$-aryl-$(C_1-C_4)$-alkyl;
R(9) is hydrogen or $(C_1-C_6)$-alkyl;
R(10) is $(C_1-C_4)$-alkoxy or hydroxycarbonyl;
R(11) is R(12) or heteroaryl, which is unsubstituted or substituted by $N(R(9))_2$ or $(C_1-C_4)$-alkyl;
R(12) is $N(R(13))_2$, COOR(9), $CON(R(13))_2$, cyano, NR(15)—C(=NR(14))—NHR(15), C(=NR(14))—R(35), —S(O)(NR(13))—N(R(13))$_2$ or C(=NR(14))—NHR(15);
R(13) is R(15);
R(14) is R(15) or hydroxy;
R(15) is hydrogen, $(C_1-C_4)$-alkyl, $(C_6-C_{14})$-aryl-$(C_1-C_6)$-alkoxycarbonyl, or $(C_1-C_6)$-alkoxycarbonyl;
R(16) is hydrogen or $(C_1-C_4)$-alkyl;
R(17) is $(C_1-C_8)$-alkyl, which is substituted by a residue R(12);

R(18) is NR(19)R(20);
R(18a) is NR(19a)R(20a);
R(19) and R(20) independently of one another are hydrogen or $(C_3-C_7)$-cycloalkyl-$(C_1-C_4)$-alkyl, where alkyl is substituted by an aminocarbonyl residue; or
R(19) and R(20) together with the nitrogen atom to which they are bound form a 6-membered, saturated heterocyclic ring, which does not contain or does contain an additional nitrogen atom and which is unsubstituted or substituted by a substituent which is naphthyl-sulfonyl substituted in the naphtyl-part with chloro;
R(19a) and R(20a) together with the nitrogen atom to which they are bound form a 6-membered heterocyclic ring, which does not contain or does contain an additional nitrogen atom and which is unsubstituted or substituted by a substituent which is phenyl or $SO_2R(31)$;
R(21) is $(C_6-C_{10})$-aryl, $(C_6-C_{10})$-aryl-$(C_1-C_4)$-alkyl or heteroaryl-$(C_1-C_4)$-alkyl, where and heteroaryl are unsubstituted or substituted independently of one another by a residue R(12) or 1, 2, 3, 4, or 5 residues R(16), the substitution by these residues at a nitrogen atom of the heteroaryl residue leading to a positively charged nitrogen atom having $X^-$ as the counterion;
R(22) is OR(9), $N(R(13))_2$, or a 5-membered nitrogen-containing heterocyclic ring, which is bound at the nitrogen;
R(23) is hydrogen, heteroaryl, which is unsubstituted or substituted by a residue $N(R(13))_2$; —NH—S(O)(NR(13))—$(C_1-C_4)$-alkyl, —S(O)(=NR(13))—N(R(13))$_2$, R(12), or R(14);
R(24) is amidino, R(29), phenyl or 2-pyridyl, which is unsubstituted or substituted by a residue R(30);
R(25) is $(C_1-C_4)$-alkyl, which is unsubstituted or substituted with one or two residues R(32); $(C_1-C_4)$-alkoxycarbonyl, cyano, chloro, CO—$N(R(13))_2$, $N(R(13))_2$, $S(O)_2$—$N(R(13))_2$ or R(12);
R(26) is hydrogen, $(C_1-C_6)$-alkyl, fluoro, chloro, $N(R(13))_2$ or $(C_1-C_4)$-alkylcarbonyl which is unsubstituted or substituted in the alkyl part by a residue N(R(13));
R(29) is hydrogen, $(C_1-C_4)$-alkoxycarbonyl, $(C_1-C_4)$-alkylcarbonyl or $SO_2R(31)$;
R(30) is nitro;
R(31) is $(C_1-C_4)$-alkyl, or $(C_6-C_{10})$-aryl, which is unsubstituted or substituted by 1 or 2 substituents which are chloro;
R(32) is NHR(29);
R(34) is $(C_1-C_8)$-alkyl, which is substituted by a residue R(12);
R(35) is hydrogen, $(C_6-C_{10})$-aryl, heteroaryl, $N(R(13))_2$, or $(C_1-C_6)$-alkyl, which is unsubstituted or substituted by a residue $N(R(13))_2$ or cyano;
n is 0, 1, or 2;
p is 2, 3, or 4;
Q is N or CH;
t is 0, 1, 2 or 3;
s is 0, 1 or 2; with the proviso that s is 2 if V is oxygen;
V is oxygen, carbonyl, or a single bond;
$X^-$ is a physiologically acceptable anion; and
Y is CH or N.
3. A compound or mixture as claimed in claim 1, wherein R(1) is NR(7)R(8) or NR(7a)R(8a).

4. A compound or mixture as claimed in claim 1, wherein

R(1) is NR(7)R(8) or NR(7a)R(8a),

R(2) is hydrogen;

R(3) is $(C_6-C_{10})$-aryl-$(C_1-C_4)$-alkyl, which is substituted in the aryl-moiety by a residue R(11);

R(4) is hydrogen;

R(5) is $(C_3-C_7)$-cycloalkyl, $(C_6-C_{10})$-aryl, or $(C_1-C_6)$-alkyl;

R(6) is R(6a), NR(34)R(13), or

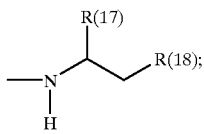

R(6a) is

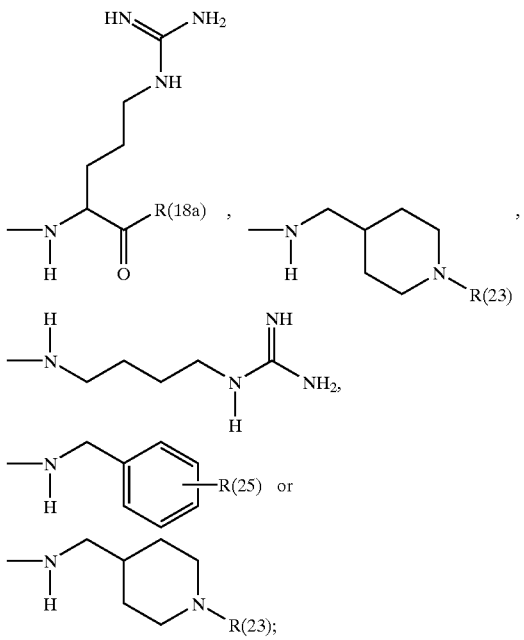

R(7) and R(8) together with the nitrogen atom to which they are bound form a 6-membered, saturated, heterocyclic ring which does not or does contain an additional oxygen atom;

R(7a) and R(8a) are independently of one another hydrogen, $(C_1-C_4)$-alkyl, or $(C_6-C_{10})$-aryl-$(C_1-C_4)$-alkyl;

R(11) is R(12);

R(12) is NR(15)—C(=NR(14))—NHR(15), C(=NR(14))—R(35) or C(=NR(14))—NHR(15);

R(13) is R(15);

R(14) is R(15);

R(15) is hydrogen or $(C_1-C_4)$-alkyl;

R(17) is $(C_1-C_8)$-alkyl, which is substituted by a residue R(12);

R(18) is NR(19)R(20);

R(18a) is NR(19a)R(20a);

R(19) and R(20) are hydrogen;

R(19a) and R(20a) together with the nitrogen atom to which they are bound form a 6-membered heterocyclic ring, which does contain an additional nitrogen atom and which is substituted by one substituent which is phenyl, or naphthyl-sulfonyl which is substituted in the naphtyl-part with chloro;

R(23) is R(12);

R(25) is R(12);

R(34) is $(C_1-C_6)$-alkyl, which is substituted by C(=N(R14))—NHR(15); and

R(35) is $N(R(13))_2$ or $(C_1-C_4)$-alkyl.

5. A compound or mixture as claimed in claim 1, wherein

R(6) is R(6a), NHR(34) or

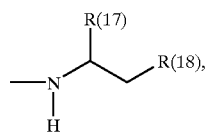

R(6a) is

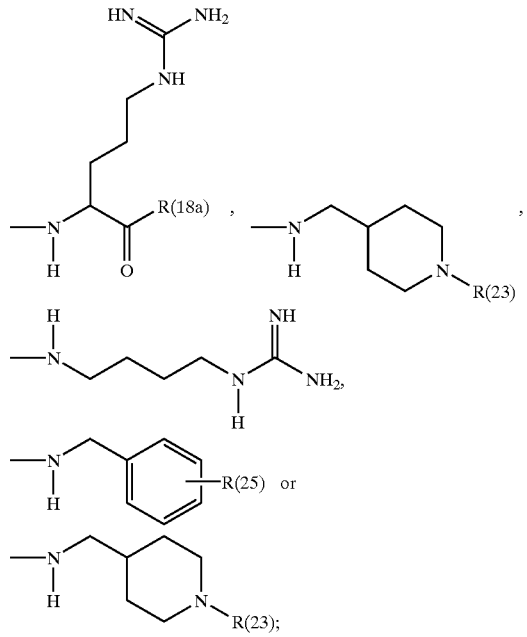

R(12) is NR(15)—C(=NR(14))—NHR(15), C(=NR(14))—R(35) or C(=NR(14))—NHR(15);

R(13) is R(15);

R(14) is R(15);

R(15) is hydrogen or $(C_1-C_4)$-alkyl;

R(17) is $(C_1-C_8)$-alkyl, which is substituted by a residue R(12);

R(18) is NR(19)R(20);

R(18a) is NR(19a)R(20a);

R(19) and R(20) are hydrogen;

R(19a) and R(20a) together with the nitrogen atom to which they are bound form a 6-membered heterocyclic ring, which does contain an additional nitrogen atom and which is substituted by one substituent which is phenyl, or naphthyl-sulfonyl which is substituted in the naphtyl-part with chloro;

R(23) is R(12);

R(25) is R(12);

R(34) is (C$_1$–C$_6$)-alkyl, which is substituted by C(=NR(14))—NHR(15); and

R(35) is N(R(13))$_2$, or (C$_1$–C$_4$)-alkyl.

6. A compound or mixture as claimed in claim 1, wherein R(1) is NR(7)R(8) or NR(7a)R(8a); R(7a) and R(8a) are both CH$_3$ or R(7a) is benzyl and R(8a) is hydrogen or CH$_3$; and R(7) and R(8) together with the nitrogen atom to which they are bound form a morpholine or piperidine.

7. A compound or mixture as claimed in claim 6, wherein R(2) and R(4) are hydrogen, R(3) is benzyl which is substituted in the aryl part with an amidine group, and R(5) is n-butyl, tert. butyl, cyclohexyl, phenyl or benzyl.

8. A compound or mixture as claimed in claim 1, wherein R(3) is benzyl which is substituted in the aryl part with an amidino group.

9. A compound as claimed in claim 1, which is

N-Benzyl-2-(4-carbamimidoyl-benzyl)-N'-{(S)-cyclohexyl-[4-guanidino-1-(S)-(4-phenyl-piperazine-1-carbonyl)-butylcarbamoyl]-methyl}-malonamide, less polar diastereomer;

2-(R,S)-(4-Carbamimidoyl-benzyl)-N-[(4-carbamimidoyl-benzylcarbamoyl)-(S)-cyclohexyl-methyl]-N',N'-dimethyl-malonamide;

2-(S)-[2-(R,S)-(4-Carbamimidoyl-benzyl)-3-morpholin-4-yl-3-oxo-propionylamino]-hexanoic acid (1-(S)-carbamoyl-4-guanidino-butyl)-amide;

2-(S)-{2-(S)-[2-(R,S)-(4-Carbamimidoyl-benzyl)-3-morpholin-4-yl-3-oxo-propionylamino]-2-phenyl-acetylamino}-5-guanidino-pentanoic acid amide;

2-(S)-{2-(S)-[2-(4-Carbamimidoyl-benzyl)-3-oxo-3-piperidin-1-yl-propionylamino]-2-cyclohexyl-acetylamino}-5-guanidino-pentanoic acid amide, less polar diastereomer;

2-(S)-{2-(S)-[2-(4-Carbamimidoyl-benzyl)-3-oxo-3-piperidin-1-yl-propionylamino]-2-phenyl-acetylamino}-5-guanidino-pentanoic acid amide, less polar diastereomer;

2-(R,S)-(4-Carbamimidoyl-benzyl)-N-({1-(S)-[4-(7-chloro-naphthalene-2-sulfonyl)-piperazine-1-carbonyl]-4-guanidino-butylcarbamoyl}-(S)-cyclohexyl-methyl)-N',N'-dimethyl-malonamide;

2-(R,S)-(4-Carbamimidoyl-benzyl)-N-[(S)-cyclohexyl-(4-guanidino-butyl-carbamoyl)-methyl]-N',N'-dimethyl-malonamide;

N-Benzyl-2-(R)-(4-carbamimidoyl-benzyl)-N'-[(S)-(4-carbamimidoyl-benzyl-carbamoyl)-cyclohexyl-methyl]-malonamide, less polar diastereomer;

N-Benzyl-2-(4-carbamimidoyl-benzyl)-N'-{(S)-[(1-carbamimidoyl-piperidin-4-ylmethyl)-carbamoyl]-cyclohexyl-methyl}-N-methyl-malonamide, less polar diastereomer;

2-(4-Carbamimidoyl-benzyl)-N-{(S)-[(1-carbamimidoyl-piperidin-4-ylmethyl)-carbamoyl]-cyclohexyl-methyl}-N',N'-dimethyl-malonamide, less polar diastereomer;

2-(4-Carbamimidoyl-benzyl)-N-{(S)-[(4-carbamimidoyl-cyclohexylmethyl)-carbamoyl]-cyclohexyl-methyl}-N',N'-dimethyl-malonamide;

N-Benzyl-2-(4-carbamimidoyl-benzyl)-N'-{(S)-[(4-carbamimidoyl-cyclohexylmethyl)-carbamoyl]-cyclohexyl-methyl}-N-methyl-malonamide, less polar diastereomer;

N-Benzyl-2-(4-carbamimidoyl-benzyl)-N'-(S)-(cyclohexyl-{[1-(1-imino-ethyl)-piperidin-4-ylmethyl]-carbamoyl}-methyl)-N-methyl-malonamide, less polar diastereomer; or N-Benzyl-2-(4-carbamimidoyl-benzyl)-N'-(S)-(cyclohexyl-{[1-(1-imino-propyl)-piperidin-4-ylmethyl]-carbamoyl}-methyl)-N-methyl-malonamide, less polar diastereomer;

or a physiologically acceptable salt thereof.

10. A process for the preparation of a compound as claimed in claim 1, which comprises i)

a1) alkylating a compound of the formula IV

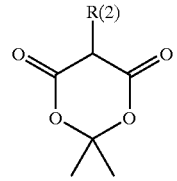

IV wherein R(2) is defined as in claim 1, with a compound of the formula V,

LG—R(3a)     (V)

wherein R(3a) is (C$_6$–C$_{10}$)-aryl-(C$_1$–C$_4$)-alkyl which is substituted in the aryl or alkyl moiety by a residue R(27); heteroaryl-(C$_1$–C$_4$)-alkyl, (C$_3$–C$_7$)-cycloalkyl-(C$_1$–C$_4$)-alkyl, where heteroaryl, cycloalkyl, or alkyl are unsubstituted or substituted by one, two, or three residues R(27), or heteroalkyl-(C$_1$–C$_4$)-alkyl, which is unsubstituted or substituted by a residue R(23); wherein R(23) is defined as in claim 1;

R(27) is R(28) or (C$_1$–C$_4$)-alkyl, which is unsubstituted or substituted by a residue R(28);

R(28) is N(R(29))$_2$, nitro, chloro or cyano, and where residues R(28), if present more than one time in the molecule, are independent of each other and can be identical or different;

R(29) is (C$_1$–C$_6$)-alkyl, (C$_6$–C$_{10}$)-aryl-(C$_1$–C$_4$)-alkyl, (C$_1$–C$_6$)-alkylcarbonyl, or (C$_1$–C$_6$)-alkoxycarbonyl, and wherein residues R(29), if present more than one time in the compound, are independent of each other and can be identical or different;

and wherein LG is a leaving group;

in the presence of a base to give a compound of the formula VI,

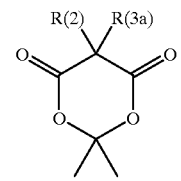

VI or reacting a compound of the formula IV with a compound of the formula Va,

Va

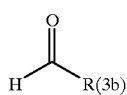

wherein R(3b) is (C₆–C₁₀)-aryl or (C₆–C₁₀)-aryl-(C₁–C₃)-alkyl which are substituted by R(27);

in the presence of a reducing agent to give a compound of the formula VI;

VI

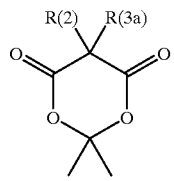

b1) reacting a compound of the formula VI with a compound of the formula VII or VIII,

VII

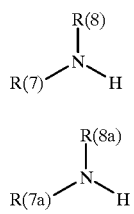

VIII wherein R(7), R(8), R(7a) and R(8a) are defined as in claim 1, to give a compound of the formula IX or X;

IX

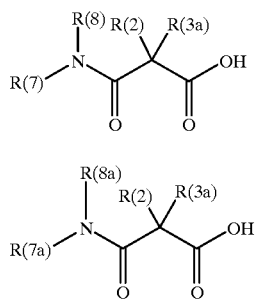

X or in case R(1) is OR(9), a2) alkylating a compound of the formula XI,

XI

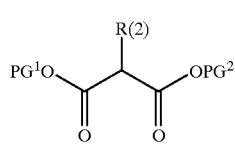

wherein R(2) is defined as in claim 1 and PG1 and PG2 are two protecting groups which can be cleaved inde pendently of each other in the presence of a base and a compound of the formula V according to step a1) to give a compound of the formula XII,

XII

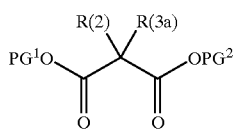

b2) deprotecting a compound of the formula XII and esterifying the deprotected compound with a compound of the formula XIII, R(9a)—OH  (XIII)

wherein R(9a) is $(C_1–C_6)$-alkyl, $(C_6–C_{10})$-aryl, $(C_6–C_{10})$-aryl-$(C_1–C_4)$-alkyl, heteroaryl, or heteroaryl-$(C_1–C_4)$-alkyl; to give a compound of the formula XIV and XV

XIV

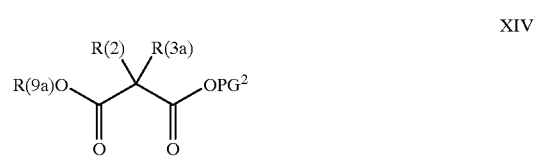

XV b3) subsequently deprotecting a compound of the formula XIV to yield a compound of the formula XV;

c1) coupling of a compound of the formula IX, X, or XV with a compound of the formula XVI,

XVI

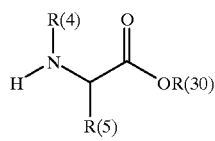

wherein R(4) and R(5) are defined as in claim 1 and R(30) is an easily cleavable ester to yield a compound of the formula XVII,

XVII

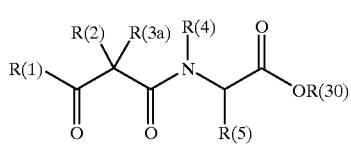

d1) optionally converting a compound of the formula XVII into a compound of the formula XVIII,

XVIII

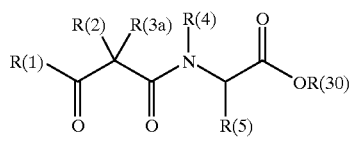

wherein R(3) is defined as in claim 1;

e1) saponification of the ester group R(30) in XVII or XVIII and coupling the resulting compound XXXII or XIX according to step c1) with a compound of the formula XX

HR(6)                                         (XX)

wherein R(6) is defined as in claim 1, to give a compound of the formula I; or c2) protecting the carboxylfunction in a compound of the formula IX, X or XV with an easily cleavable protecting group and optionally introducing an amidino or guanidino group according to step d1) to give a compound of the formula XXI, XXII, or XXIII; and

XXI

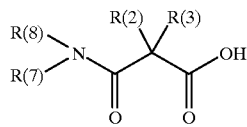

XXII

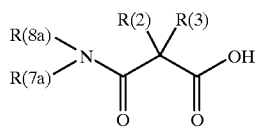

XXIII

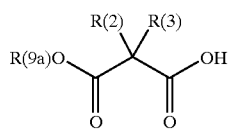

d2) coupling a compound of the formula XXI, XXII or XXIII according to step c1) with a compound of the formula XXVI;

XXVI

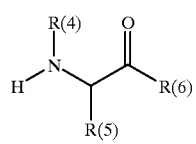

to give a compound of the formula I; or ii) a) coupling a compound of the formula XXVII,

XXVII

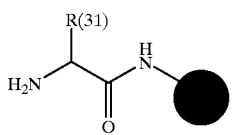

which is bound to a suitable carrier and wherein

R(31) is R(17), R(21), or (CH$_2$)$_3$—NR(33)—C(=N—R(32))—NH—R(33);

wherein R(17) and R(21) are defined as in claim 1;

R(32) is R(33), cyano, hydroxy, (C$_1$–C$_6$)-alkoxy, (C$_6$–C$_{14}$)-aryl-(C$_1$–C$_6$)-alkoxy, which is unsubstituted or substituted in the aryl moiety, or amino, and where residues R(32), if present more than one time in the molecule, are independent of each other and are identical or different;

R(33) is hydrogen, (C$_1$–C$_6$)-alkyl, or (C$_1$–C$_6$)-alkylcarbonyl;

with a compound of the formula XXIV

XXIV

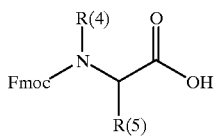

wherein R(4) and R(5) are defined as in claim 1 to give a compound of the formula XXVI

XXVI

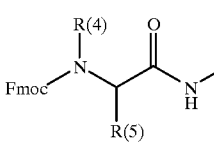

b) and after deprotecting a compound of the formula XXVI with a base coupling the deprotected compound to a compound of the formula IX, X, XV, XXI, XXII, or XXIII to give a compound of the formula XXX;

XXX

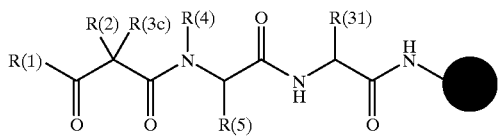

c) optionally converting a compound of the formula XXX to a compound of the formula XXXI

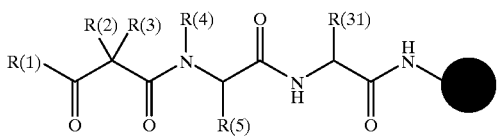

XXXI and d) cleaving a compound of the formula XXXI (or XXX) off the resin to give a compound as claimed in claim 1.

11. A pharmaceutical composition comprising one or more compounds as claimed in claim 1 togetherwith a pharmaceutically acceptable carrier or auxiliary substance.

12. A method for inhibiting factor Xa in an individual, which comprises administering to the individual an effective amount of a compound or mixture as claimed in claim 1.

13. A method for inhibiting blood clotting in an individual, which comprises administering to the individual an effective amount of a compound or mixture as claimed in claim 1.

14. A method for the treatment or prophylaxis of a cardiovascular disorder or thromboembolic condition in an individual, which comprises administering to the individual an effective amount of a compound or mixture as claimed in claim 1.

15. A method for the treatment or prevention of a complication in an individual associated with infection or surgery, which comprises administering to the individual an effective amount of a compound or mixture as claimed in claim 1.

16. A method as claimed in claim 14, wherein the cardiovascular disorder is restenosis, restenosis following angioplasty, reocclusion prophylaxis, a condition after a coronary bypass operation, an arterial, venous or microcirculatory disease state, cardiac infarction, angina pectoris, a thromboembolic disease, thrombosis, embolism, adult respiratory distress syndrome, multi-organ failure, stroke or a disseminated intravascular coagulation clotting disorder.

17. A method as claimed in claim 15, wherein the complication associated with surgery is a deep vein or proximal vein thrombosis.

* * * * *

UNITED STATES PATENT AND TRADEMARK OFFICE
CERTIFICATE OF CORRECTION

PATENT NO. : 6,395,737 B1
DATED : May 28, 2002
INVENTOR(S) : Defossa et al.

It is certified that error appears in the above-identified patent and that said Letters Patent is hereby corrected as shown below:

<u>Title page,</u>
Item [74], in the name of the firm, after "Finnegan," delete the period.

<u>Column 61,</u>
Line 7, after "natural" delete the line break.

<u>Column 63,</u>
Line 18, after "$(C_6-C_{10})$-aryl" insert a comma.
Line 54, before "bridge" delete "O-".

<u>Column 65,</u>
Structure on lines 3 through 8,

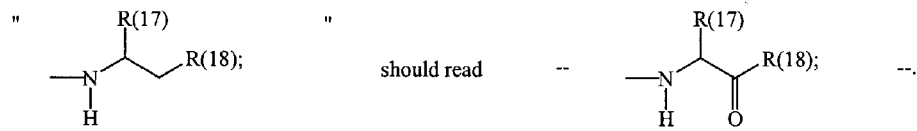

Structure on lines 30 through 35,

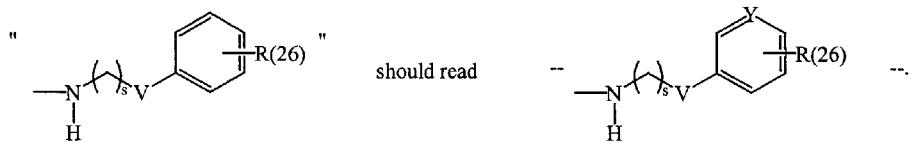

Structure on lines 36 through 40,

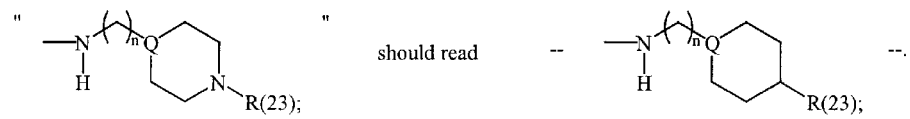

<u>Column 66,</u>
Line 20, after "where" insert -- aryl --.

UNITED STATES PATENT AND TRADEMARK OFFICE
CERTIFICATE OF CORRECTION

PATENT NO.   : 6,395,737 B1
DATED        : May 28, 2002
INVENTOR(S)  : Defossa et al.

It is certified that error appears in the above-identified patent and that said Letters Patent is Column 67,
Structure on lines 12 through 16,

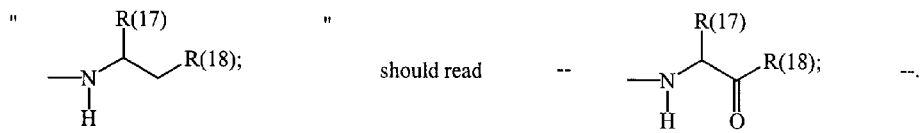

Structure on lines 40 through 44,

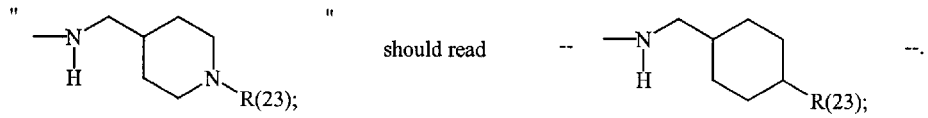

Column 68,
Structure on lines 14 through 18,

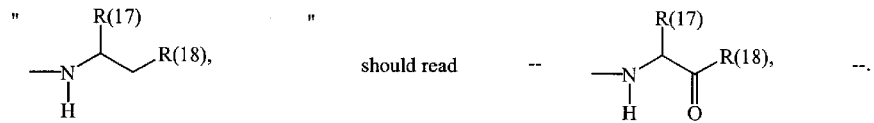

Structure on lines 42 through 46,

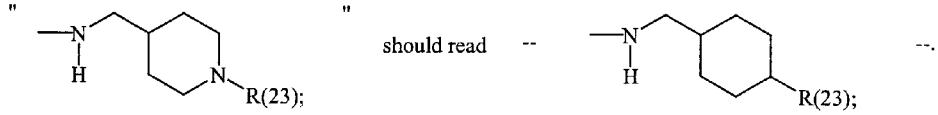

UNITED STATES PATENT AND TRADEMARK OFFICE
CERTIFICATE OF CORRECTION

PATENT NO. : 6,395,737 B1
DATED : May 28, 2002
INVENTOR(S) : Defossa et al.

It is certified that error appears in the above-identified patent and that said Letters Patent is hereby corrected as shown below:

Column 71, line 67 to Column 72, line 1,
"inde pendently" should read -- independently --.

Column 73,
Formula XVIII, lines 1 through 7,

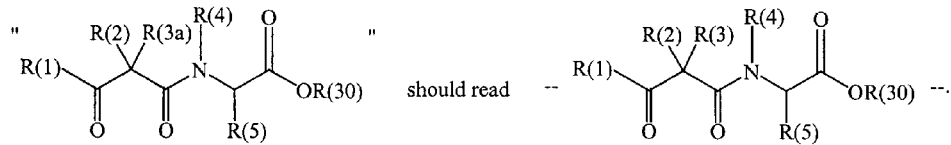 should read

Column 75,
Line 14, "togetherwith" should read -- together with --.

Signed and Sealed this

Twenty-second Day of October, 2002

Attest:

Attesting Officer

JAMES E. ROGAN
Director of the United States Patent and Trademark Office